US011701058B2

(12) United States Patent
Calcano et al.

(10) Patent No.: US 11,701,058 B2
(45) Date of Patent: Jul. 18, 2023

(54) PERSONAL IMPACT MONITORING SYSTEM

(71) Applicant: I1 SENSORTECH, INC., Kirkland, WA (US)

(72) Inventors: Lawrence V. Calcano, Kirkland, WA (US); David Thomas Brown, Kirkland, WA (US); Christopher C. Genau, Kirkland, WA (US); David Ernest Snyder, Kirkland, WA (US); James M. Stearns, Kirkland, WA (US); Brian Michael Ronald, Kirkland, WA (US); Jesse David Harper, Kirkland, WA (US); John F. Harris, Kirkland, WA (US)

(73) Assignee: i1 SENSORTECH, INC., Kirkland, WA (US)

( * ) Notice: Subject to any disclaimer, the term of this patent is extended or adjusted under 35 U.S.C. 154(b) by 870 days.

(21) Appl. No.: 16/576,678

(22) Filed: Sep. 19, 2019

(65) Prior Publication Data

US 2020/0205733 A1 Jul. 2, 2020

Related U.S. Application Data

(63) Continuation of application No. 15/023,306, filed as application No. PCT/US2014/057852 on Sep. 26, 2014, now Pat. No. 10,420,507.

(Continued)

(51) Int. Cl.
*A61B 5/00* (2006.01)
*G01L 5/00* (2006.01)
(Continued)

(52) U.S. Cl.
CPC ............ *A61B 5/682* (2013.01); *A61B 5/0002* (2013.01); *A61B 5/02055* (2013.01);
(Continued)

(58) Field of Classification Search
CPC ..... A61B 5/742; A61B 5/7282; A61B 5/7264; A61B 5/682; A61B 5/1118; A61B 5/02055; A61B 5/0002
See application file for complete search history.

(56) References Cited

U.S. PATENT DOCUMENTS 5,365,946 A 11/1994 McMillan
5,385,155 A 1/1995 Kittelsen et al.
(Continued)

FOREIGN PATENT DOCUMENTS

CA 2734479 A1 9/2012
WO 2006074411 A2 7/2006
(Continued)

OTHER PUBLICATIONS

"SAE J211-1 (1995): Instrumention for Impact Test, Part 1, Electronic Instrumentation," Society of Automotive Engineers, Inc., May 4, 2007, 22 pages.
(Continued)

*Primary Examiner* — Daniel L Cerioni
(74) *Attorney, Agent, or Firm* — Davis Wright Tremaine LLP

(57) ABSTRACT

A personal impact monitoring system is described herein comprising a monitoring station that receives impact events sent from personal impact monitors using a monitoring station receiver. The impact events which specify impact parameters associated with the impact events are stored in a data storage location associated with the monitoring station. Software operating on the operating station is configured to receive the impact events from the data storage location and to perform calculations based on the impact events to identify notable impact events.

6 Claims, 29 Drawing Sheets

Related U.S. Application Data

(60) Provisional application No. 62/035,298, filed on Aug. 8, 2014, provisional application No. 61/883,108, filed on Sep. 26, 2013.

(51) Int. Cl.

| | | |
|---|---|---|
| *A61B 5/11* | (2006.01) | |
| *G16H 15/00* | (2018.01) | |
| *G16H 50/70* | (2018.01) | |
| *A61B 5/0205* | (2006.01) | |
| *A61L 2/04* | (2006.01) | |
| *A61L 2/10* | (2006.01) | |
| *A61L 2/16* | (2006.01) | |
| *A63B 71/08* | (2006.01) | |
| *A61B 5/01* | (2006.01) | |
| *A61B 5/021* | (2006.01) | |
| *A61B 5/08* | (2006.01) | |
| *A61B 5/024* | (2006.01) | |

(52) U.S. Cl.
CPC ........... *A61B 5/1114* (2013.01); *A61B 5/1118* (2013.01); *A61B 5/1123* (2013.01); *A61B 5/7246* (2013.01); *A61B 5/7264* (2013.01); *A61B 5/7282* (2013.01); *A61B 5/742* (2013.01); *A61L 2/04* (2013.01); *A61L 2/10* (2013.01); *A61L 2/16* (2013.01); *A63B 71/085* (2013.01); *G01L 5/00* (2013.01); *G01L 5/0052* (2013.01); *G16H 15/00* (2018.01); *G16H 50/70* (2018.01); *A61B 5/01* (2013.01); *A61B 5/021* (2013.01); *A61B 5/024* (2013.01); *A61B 5/02438* (2013.01); *A61B 5/0816* (2013.01); *A61B 2503/10* (2013.01); *A61B 2560/0223* (2013.01); *A61B 2560/0456* (2013.01); *A61B 2562/0219* (2013.01); *A61L 2202/11* (2013.01)

(56) References Cited

U.S. PATENT DOCUMENTS

| | | |
|---|---|---|
| 5,584,687 A | 12/1996 | Sullivan et al. |
| 5,718,575 A | 2/1998 | Cross, III |
| 5,836,761 A | 11/1998 | Belvedere et al. |
| 5,865,619 A | 2/1999 | Cross, III et al. |
| 5,879,155 A | 3/1999 | Kittelsen |
| 6,012,919 A | 1/2000 | Cross, III et al. |
| 6,200,133 B1 | 3/2001 | Kittelsen |
| 6,237,601 B1 | 5/2001 | Kittelsen et al. |
| 6,257,239 B1 | 7/2001 | Kittelsen et al. |
| 6,371,758 B1 | 4/2002 | Kittelsen |
| 6,415,794 B1 | 7/2002 | Kittelsen et al. |
| 6,491,036 B2 | 12/2002 | Cook |
| 6,505,626 B2 | 1/2003 | Kittelsen et al. |
| 6,505,627 B2 | 1/2003 | Kittelsen et al. |
| 6,505,628 B2 | 1/2003 | Kittelsen et al. |
| 6,508,251 B2 | 1/2003 | Kittelsen et al. |
| 6,510,853 B1 | 1/2003 | Kittelsen et al. |
| 6,539,943 B1 | 4/2003 | Kittelsen et al. |
| 6,553,996 B2 | 4/2003 | Kittelsen et al. |
| 6,581,604 B2 | 6/2003 | Cook |
| 6,588,430 B2 | 7/2003 | Kittelsen et al. |
| 6,598,605 B1 | 7/2003 | Kittelsen et al. |
| 6,626,180 B1 | 9/2003 | Kittelsen et al. |
| 6,675,806 B2 | 1/2004 | Kittelsen et al. |
| 6,675,807 B2 | 1/2004 | Kittelsen et al. |
| 6,691,710 B2 | 2/2004 | Kittelsen et al. |
| 6,820,623 B2 | 11/2004 | Cook |
| 6,826,509 B2 | 11/2004 | Crisco, III et al. |
| 7,299,804 B2 | 11/2007 | Kittelsen et al. |
| 7,481,773 B1 | 1/2009 | Dorroh et al. |
| 8,113,206 B2 | 2/2012 | Roettger et al. |
| 8,481,970 B2 | 7/2013 | Cooper et al. |
| 8,689,797 B2 | 4/2014 | Elkin et al. |
| 9,007,217 B1 | 4/2015 | Anvari |
| 9,457,828 B1* | 10/2016 | Guirlinger ................ B62B 3/04 |
| 2002/0060633 A1* | 5/2002 | Crisco, III ........... A61B 5/6814 340/669 |
| 2004/0196374 A1 | 10/2004 | Billerbeck |
| 2004/0250817 A1 | 12/2004 | Kittelsen et al. |
| 2005/0134439 A1 | 6/2005 | Moore et al. |
| 2005/0266967 A1 | 12/2005 | Considine et al. |
| 2006/0074338 A1 | 4/2006 | Greenwald et al. |
| 2006/0189852 A1 | 8/2006 | Greenwald et al. |
| 2007/0271686 A1 | 11/2007 | Rast |
| 2010/0044582 A1 | 2/2010 | Cooper et al. |
| 2011/0179851 A1 | 7/2011 | Mack et al. |
| 2011/0181418 A1 | 7/2011 | Mack et al. |
| 2011/0181419 A1 | 7/2011 | Mack et al. |
| 2011/0181420 A1 | 7/2011 | Mack et al. |
| 2011/0184319 A1 | 7/2011 | Mack et al. |
| 2011/0184320 A1 | 7/2011 | Shipps et al. |
| 2011/0184663 A1 | 7/2011 | Mack et al. |
| 2011/0221590 A1 | 9/2011 | Baker et al. |
| 2011/0245633 A1 | 10/2011 | Goldberg et al. |
| 2012/0143526 A1 | 6/2012 | Benzel et al. |
| 2012/0172677 A1 | 7/2012 | Logan et al. |
| 2012/0188083 A1 | 7/2012 | Miller, II |
| 2012/0191379 A1 | 7/2012 | Li et al. |
| 2012/0210498 A1 | 8/2012 | Mack |
| 2012/0220893 A1 | 8/2012 | Benzel et al. |
| 2012/0223833 A1 | 9/2012 | Thomas et al. |
| 2012/0296601 A1 | 11/2012 | Eatwell |
| 2012/0304367 A1 | 12/2012 | Howard et al. |
| 2012/0304767 A1 | 12/2012 | Howard et al. |
| 2012/0309300 A1 | 12/2012 | Howard et al. |
| 2012/0325224 A1 | 12/2012 | Elkin et al. |
| 2013/0060168 A1 | 3/2013 | Chu et al. |
| 2013/0060489 A1 | 3/2013 | Crossman et al. |
| 2013/0074248 A1 | 3/2013 | Evans et al. |
| 2013/0110415 A1 | 5/2013 | Davis et al. |
| 2013/0282308 A1* | 10/2013 | Mack ..................... A42B 3/046 702/41 |
| 2013/0332286 A1 | 12/2013 | Medelius et al. |
| 2014/0052405 A1 | 2/2014 | Wackym |
| 2014/0081601 A1 | 3/2014 | Zhang et al. |
| 2014/0143940 A1 | 5/2014 | Iuliano et al. |
| 2015/0040685 A1 | 2/2015 | Nicholson et al. |
| 2015/0046116 A1 | 2/2015 | Eatwell |
| 2015/0097700 A1* | 4/2015 | Holthouse ................ H04Q 9/00 340/870.03 |
| 2015/0226621 A1 | 8/2015 | Zhu et al. |
| 2015/0375083 A1 | 12/2015 | Stelfox et al. |
| 2016/0058093 A1 | 3/2016 | Kennard et al. |

FOREIGN PATENT DOCUMENTS

| | | |
|---|---|---|
| WO | 2009012243 A2 | 1/2009 |
| WO | 2009155223 A1 | 12/2009 |
| WO | 2009155224 A1 | 12/2009 |

OTHER PUBLICATIONS

Extended European Search Report dated May 10, 2017, European Patent Application No. 14848170.8, filed Sep. 26, 2014, 10 pages.
International Search Report and Written Opinion dated Dec. 29, 2014, International Patent Application PCT/US2014/057852, filed Sep. 26, 2014, 11 pages.
Zhang et al., "Recent advances in brain injury research: a new human head model development and validation," Stapp Car Crash Journal 45(11):369-94, Nov. 1, 2001.
Chinese First Office Action dated Apr. 29, 2019, Patent Application No. 201480053131.4, filed Sep. 26, 2014, 7 pages.
Canadian Office Action dated Jul. 7, 2020, Patent Application No. 2922981, 4 pages.
Canadian Office Action dated Apr. 1, 2021, Patent Application No. 2922981, 4 pages.

(56) References Cited

OTHER PUBLICATIONS

Canadian Office Action dated Nov. 29, 2021, Patent Application No. 2922981, 3 pages.

* cited by examiner

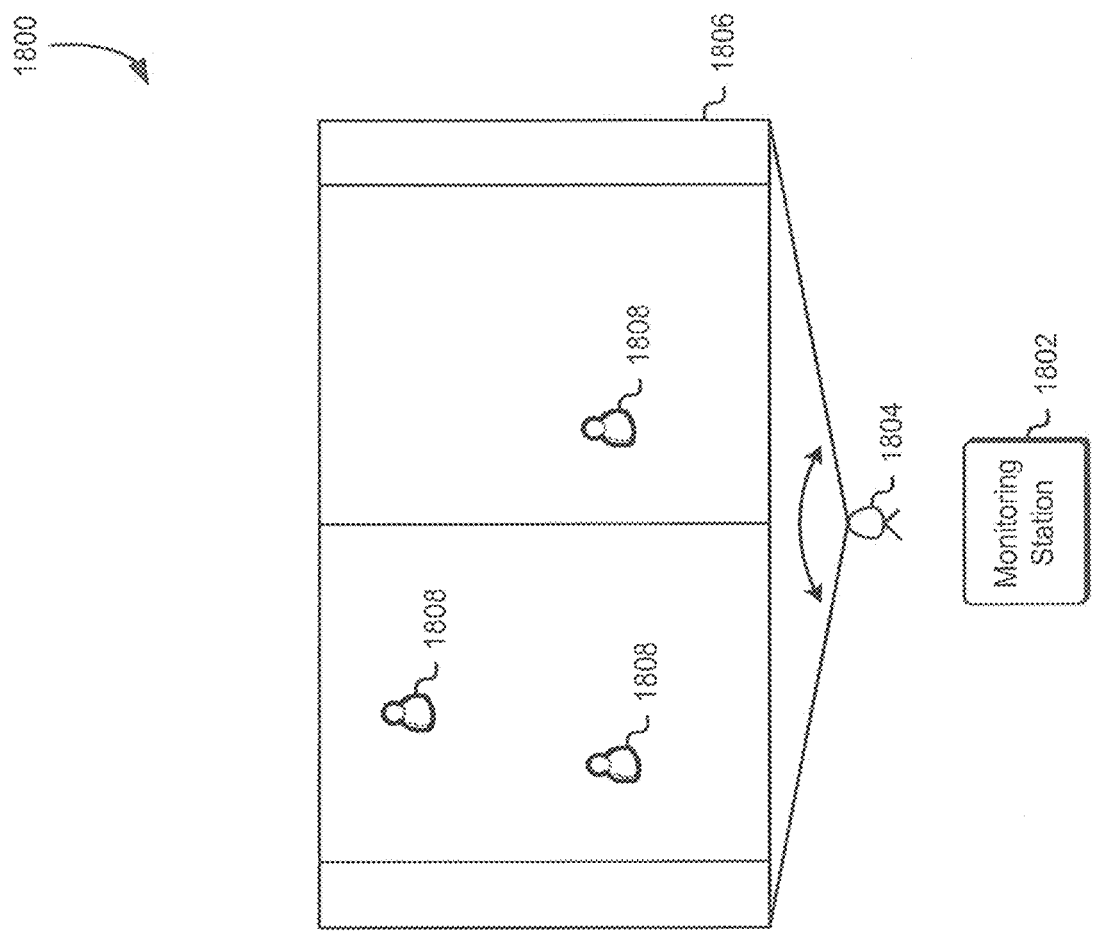
FIG. 18
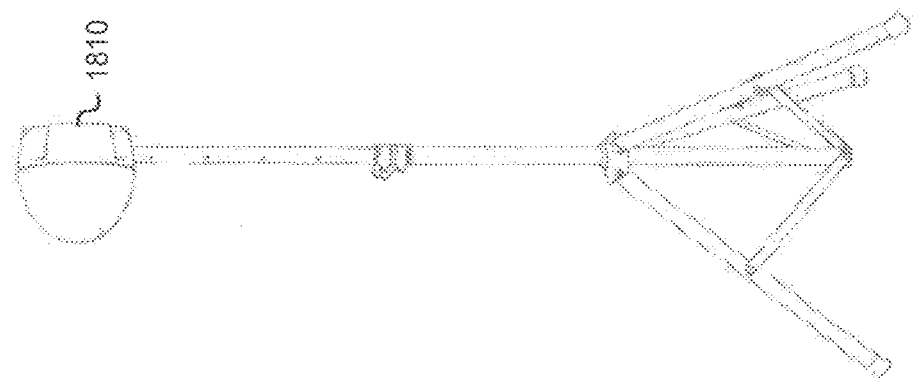

FIG. 23

| Roster | Impacts | Administration | | |
|---|---|---|---|---|
| User Name  Sign Out | | Menu | | ? Help |
| Player | | Custom Threshold | | Status |
| #21 ANDERSON, J | | 76 | 14g below team default | Active |
| #89 BRUNNER, D | | | | Active |
| #10 COLAIACOVO, C | | | | 13 Mins. |
| #12 CLEARY, D | | | | 1 Min. |
| #72 EMMERTON, C | | 80 | 10g below team default | Active |
| #23 ERICSSON, J | | | | Active |
| #74 FILIPPULA, W | | | | 2 Days |
| #65 FRANZEN, J | | | | Active |
| #36 KRONWALL, N | | | | 2 Weeks |
| #55 LASHOFF, B | | 65 | 25g below team default | 1 Hour |
| #29 SAMUELSSON, M | | | | 26 Mins. |
| #19 BOWBUCK, S | | | | Active |

FIG. 24

PERSONAL IMPACT MONITORING SYSTEM

CROSS-REFERENCE TO RELATED APPLICATIONS

This application is a continuation of U.S. patent application Ser. No. 15/023,306, filed on Mar. 18, 2016, entitled "PERSONAL IMPACT MONITORING SYSTEM," a National Stage Entry of PCT/US2014/057852, filed Sep. 26, 2014, which claims priority to and incorporates by reference for all purposes the full disclosure of U.S. Provisional Patent Application No. 61/883,108, filed on Sep. 26, 2013, entitled "IMPACT REVIEW SYSTEM" and U.S. Provisional Patent Application No. 62/035,298, filed on Aug. 8, 2014, entitled "BODY IMPACT ANALYSIS, SYSTEMS, AND METHODS OF USE."

BACKGROUND

Positive acceleration or negative acceleration (i.e., deceleration) of the human body occurs whenever its velocity undergoes a change, and is a consequence of human movement. Most acceleration of the human body is benign, but when the magnitude of acceleration becomes too large, as may occur with a direct blow or impact, it can be injurious, and can be especially injurious to fragile body parts such as the brain. Furthermore, different types of acceleration can lead to different types of brain injuries. High linear acceleration can cause focal injuries such as contusions and intra-cerebral or subdural hematomas. Concussions and diffuse axonal injury (DAI) are believed to result when there is a significant rotational acceleration component of the injury mechanism. Repetitive exposure to traumatic brain injury can also lead to chronic traumatic encephalopathy ("CTE"), a progressive, degenerative brain disease.

Injurious acceleration can be experienced in many situations (e.g., in an automobile accident or in a slip and fall), but some professions and activities expose their participants to a higher probability of injurious acceleration. For example, military combat personnel may be exposed to a heightened probability of blast injuries, which can cause CTE after as few as a single exposure. Athletes may also be exposed to an elevated probability of injurious acceleration caused by a direct impact to the head, face, neck, or elsewhere on the body during the athletic activity. Brain injury can result even when the impact is not delivered directly to the head since the acceleration can be transmitted through the body to the brain. Such impacts can occur as a result of accidental or intentional collisions between athletes, or between an athlete and an inanimate object (e.g., a ball, goal post, fence, or the ground). While the probability of an injurious impact is higher in contact sports, participants in non-contact sports are not immune from such injurious impact.

When sporting injuries are considered, an elevated probability of occurrence is combined with a large and growing number of participants. The United States Centers for Disease Control estimated that more than 3,800,000 sports brain injuries occur every year, and that as many as 80% of them may go undetected and/or unrecognized. It is further estimated that more than 300,000 sports brain injuries per year result in a loss of consciousness. Additionally, individuals exposed to an elevated probability of serious head impact are also frequently exposed to high environmental temperatures due to, for example, padding and helmets for athletes, body armor for military personnel, or protective clothing for emergency response personnel. Exertion under such circumstances can lead to hyperthermia, heat stroke, and death.

BRIEF DESCRIPTION OF THE FIGURES

Various embodiments in accordance with the present disclosure will be described with reference to the drawings, in which:

FIG. 18 illustrates an environment where a sideline receiver may be placed relative to a playing field in accordance with an embodiment;

FIGS. 23 to 27 illustrate aspects of a user interface for displaying impact events in accordance with an embodiment;

DETAILED DESCRIPTION

Figure 1:
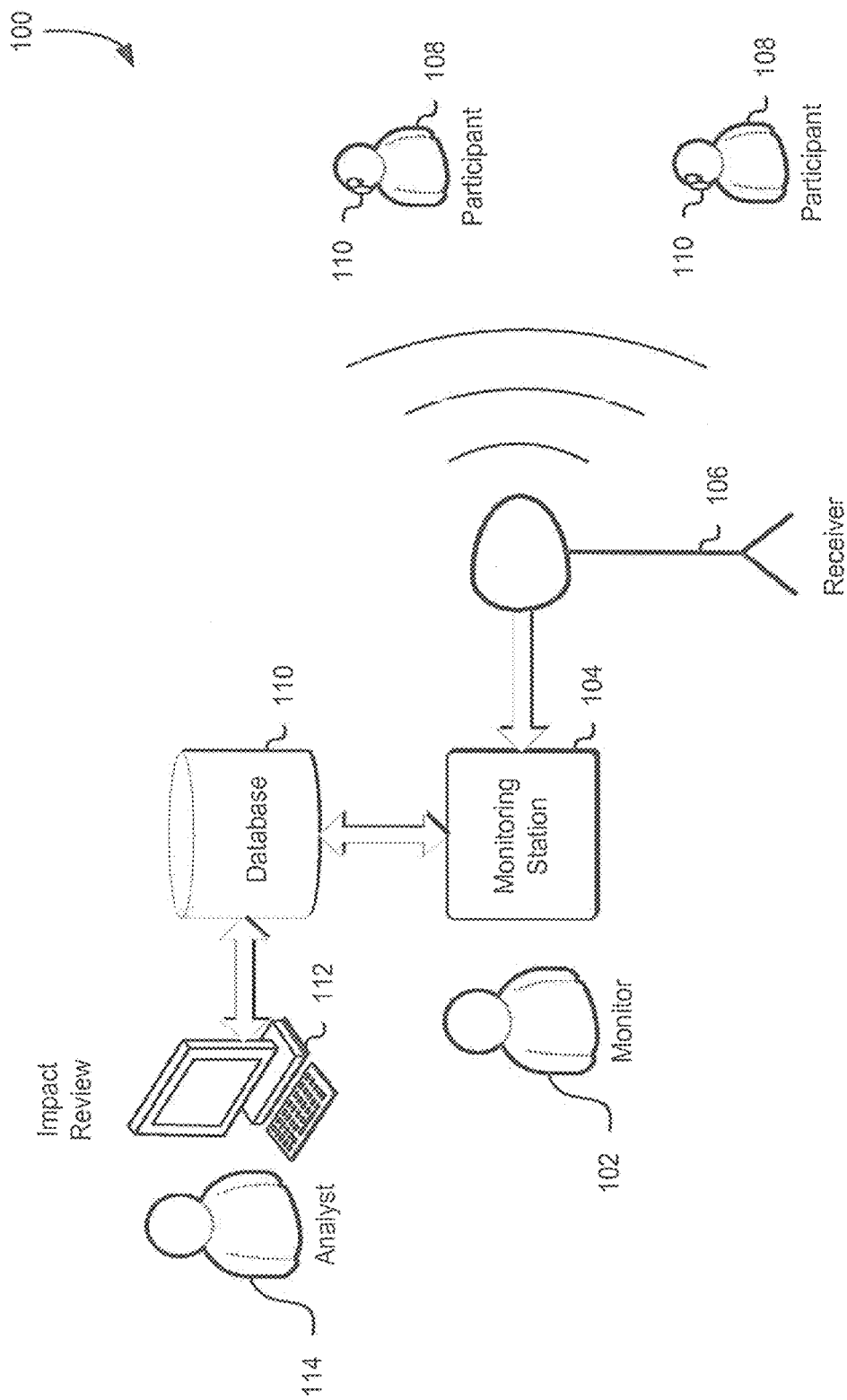
FIG. 1 illustrates an environment where impacts may be detected, recorded, analyzed, and reviewed in accordance with an embodiment.

In the following description, various embodiments will be described. For purposes of explanation, specific configurations and details are set forth in order to provide a thorough understanding of the embodiments. However, it will also be apparent to one skilled in the art that the embodiments may be practiced without the specific details. Furthermore, well-known features may be omitted or simplified in order not to obscure the embodiment being described.

Techniques described and suggested herein include methods, systems, and processes to provide personal impact monitoring (also referred to herein as "monitoring impacts") for individuals that engage in activities that may expose them to an elevated probability of injurious impacts. The methods, systems, and processes described herein provide timely information related to high-acceleration impacts received by an individual. The timely information related to the high-acceleration impacts may be for the entire body or may be limited to a certain region such as, for example, the head. The timely information can be used, for example, to reduce the number or percentage of unrecognized brain impacts, to provide coaches and trainers with data that may enable behavior modification for athletes receiving frequent and/or high-acceleration impacts, to provide military personnel or their commanders with information for risk assessment, or to provide emergency management personnel with such information. The efficacy of the timely information may be enhanced by additional biometric signals, such as oral temperature, to guard against separate but associated risks.

Personal impact monitoring may be performed using a personal impact monitor for a person such as, for example, an athlete, a soldier, or an emergency responder, who may be exposed to an elevated probability of injurious impacts. A personal impact monitor ("PIM") is a device such as an instrumented mouth guard, adhesive patch, or other personal impact-sensing device that is directly or indirectly attached to the person and that may relay impact and/or other biometric data to a personal impact monitoring system or service using the methods, systems, and processes described herein. Components of methods, systems, and processes for personal impact monitoring may include, but may not be limited to, personal impact monitors, bank chargers, bank charger enclosures, monitoring station radios or monitoring station antennas, monitoring stations, remote notification devices, near-field data display devices, initialization and test software, impact analysis software, data management software, event display software, asset management software, data reconciliation software, database software (also referred to herein as "data persistence software"), statistical analysis software, user interface software, or other such components. These components are described in more detail below. Components of methods, systems, and/or processes for personal impact monitoring may also include, but may also not be limited to, any of the systems, methods, or processes for personal impact monitoring as described in U.S. Pat. App. Pub. No. 2011/0179851; U.S. Pat. App. Pub. No. 2011/0181418; U.S. Pat. App. Pub. No. 2011/0181419; U.S. Pat. App. Pub. No. 2011/0181420; U.S. Pat. App. Pub. No. 2011/0184319; U.S. Pat. App. Pub. No. 2011/0184663; and U.S. Pat. App. Pub. No. 2012/0210498, the entire disclosures of which are incorporated by reference herein.

A personal impact monitoring system may be used in association with a number of different activities including a contact sport (i.e., a sport such as American football where players may impact each other), fire and rescue situations, military operations, or other such activities. For example, a personal impact monitoring system may be used in connection with an American football game with personal impact monitors incorporated into mouth guards worn by the players, one or more antennas located proximal to the field, and a monitoring station located near the field so that the system may receive and/or analyze the impact event data from the personal impact monitors and present analyses of the data to the coach. Each impact event may specify one or more impact event parameters such as, for example, the type of the impact, the severity of the impact, the location of the impact, and other such impact event parameters. In another example, a personal impact monitoring system may be used in connection with a fire and rescue situation with personal impact monitors incorporated into ear pieces worn by the fire and rescue workers. The personal impact monitoring station may be located near the site of the fire and rescue operations and an incident commander may use the personal impact monitoring station to monitor the safety of the workers.

FIG. 1 illustrates an example environment 100 where impacts may be detected, recorded, analyzed, and reviewed in accordance with an embodiment. One or more participants 10 may be fitted with personal impact monitors 110 as described herein. The participants 108 may be players in an athletic contest, or may be military personnel, or may be emergency personnel (e.g., fire and rescue personnel), or may be some other type of participants that may require impact monitoring. The personal impact monitors 110 may be mounted on a helmet, or mounted on other protective gear, or worn over the ear, or worn as a mouth guard, or may be attached to the participant 108 using some other mechanism. Each participant 108 may have one or more personal impact monitors 110 attached, providing monitoring of different types of data and/or data from different locations. Details about each of the components illustrated in FIG. 1 are described herein at least in connection with FIGS. 2 and 3.

Figure 2:
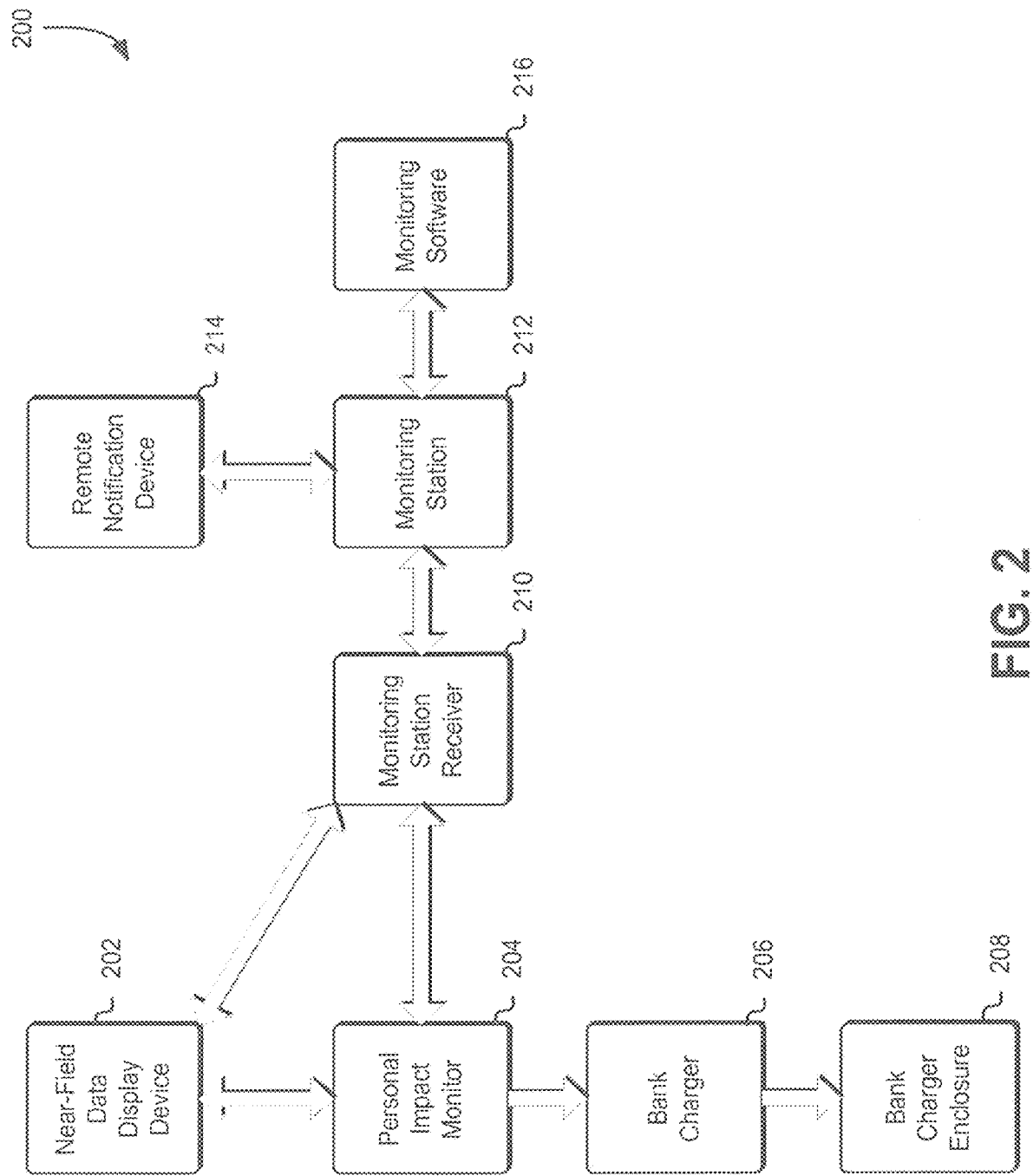
FIG. 2 illustrates an environment where components of a personal impact monitoring system may operate in accordance with an embodiment.

FIG. 2 illustrates an example environment 200 where components of a personal impact monitoring system may operate as described herein in connection with FIG. 1 and in accordance with an embodiment. The personal impact monitoring system illustrated in FIG. 2 includes a PIM 204, which may communicate with a near-field data display device 202 over short distances using a short-range communication channel.

As used herein, a short-range communication channel may be a communication channel that may be established between a pair of devices using various technologies, such as induction wireless, infrared wireless (including such technologies operating according to specifications and protocols provided by the Infrared Data Association, or "IrDA") or ultra wideband formats. In some embodiments, the pair of devices may utilize short-range, low-power, and high-frequency radio transmissions, such as Bluetooth®. In other embodiments, the pair of devices may support acoustic-based data transfer. For example, the second device of the pair of devices may include software components and a speaker that enables the second device to broadcast data to the first device using sound waves, while the first device of the pair of devices may include software components and microphone that enables the first device to receive the data embedded in the sound waves. Thus, one or more of radio signal-based data transfer (e.g., near field communication (NFC) or Bluetooth®), light-based data transfer (e.g., infrared data transfer), an acoustic-based data transfer (e.g., sound wave-embedded data), or magnetic field-based transfer (e.g., reading data from a magnetic stripe) may be used for short-range communication. Each short-range communication channel may have an associated communications range beyond which the short-range communication channel may not reliably operate. The protocols and components for enabling computing devices to perform short-range communication are well known to those skilled in the art of computer communications and thus, need not be described in more detail herein. Generally, embodiments described herein are not limited to those explicitly illustrated herein.

The PIM 204 may be connected to a bank charger 206 that may, in turn, be stored in a bank charger enclosure 208. The PIM 204, which may be one of a plurality of PIMs, may communicate with a monitoring station receiver 210 using a wireless communications protocol such as wireless internet. The near-field data display device 202 may also be configured to communicate with the monitoring station receiver 210 using a wireless communications protocol such as wireless internet. The monitoring station receiver 210 may be connected to a monitoring station 212 using wired, wireless, or a combination of wired and wireless communications. The monitoring station receiver 210 may be one of a plurality of such receivers.

The monitoring station may be comprised of one or more computer systems that may be running monitoring software 216, which may be configured to perform one or more operations in association with the personal impact monitoring system. One or more of the components of the personal impact monitoring system (including, but not limited to, the PIM 204, the near-field data display device 202, the bank charger 206, the monitoring station receiver 210, the monitoring station 212, or the monitoring software 216 may be configured to generate events that may be sent to a remote notification device 214 that may be worn by a user of the personal impact monitoring system or may be worn by a monitor observer such as the monitor observer 102 illustrated in connection with FIG. 1. Each of the components illustrated in FIG. 2 is described in more detail below. The monitoring software 216 is described in more detail in connection with FIG. 3.

The system illustrated in FIG. 2 may include a near-field data display device 202. A near-field data display device 202 is a system component which may include a display, application software, and a means to communicate with a PIM 204 using short-range communication or near-field communication ("NFC") technology as described herein. A near-field data display device 202 may be configured to request and/or receive impact event data (i.e., impact event parameters) from a PIM 204, and may also be configured to display at least a subset of such impact data. For example, a near-field data display device 202 may be configured to, when placed in proximity to a PIM 204, request and receive recent impact data from that PIM and display the number of recent impacts, the number of atypical impacts, details about recent impacts, or other such information. The near-field device may be a handheld device (e.g., a tablet, a smartphone, a laptop computer), and may be configured to display at least a subset of the content such as the content described herein below.

A PIM 204 as described herein may be an instrumented mouth guard, ear piece, adhesive patch, or other personal impact-sensing device that is directly or indirectly attached to a participant. A PIM 204 may include one or more sensors that are configured to sense one or more motions of the participant including, but not limited to, rotational velocity, linear velocity, rotational acceleration, linear acceleration, or other such motions. The motions and/or the changes in such motions may be in response to bodily impact. As used herein, the term "impact" may refer to a body contacting another object (including another body), a body experiencing sudden movement in response to, for example, a blast, an object contacting another object, and/or simulated impacts in which a body is moved to simulate contact with another object. A PIM 204 is described herein as attached to a participant (or person), but may also be attached to objects. For example, in a system where PIMs are attached to players in an American football game, PIMs may also be attached to the ball, the goalposts, blocking "dummies," and so on.

In some embodiments, a PIM 204 is configured such that it can communicate with a remote device. As used herein, the term "remote device" may refer to a device that is either in wired or wireless communication with the PIM 204, either directly or indirectly. The communication between the PIM 20'1 and the remote device may be made using one or more of the network communications protocols described herein. For example, the PIM 204 and one or more remote devices may be configured to communicate using wireless communication protocols (e.g., radio frequency ("RF"), wireless internet, or Bluetooth) or may be configured to communicate using wired communication protocols (e.g., wired internet, universal serial bus ("USB"), or direct connection). Data may be communicated both to and from the PIM and the one or more remote devices. For example, data from one or more sensors of the PIM may be communicated to the one or more remote devices and commands and/or responses from the one or more remote devices may be communicated to the PIM. In some embodiments, the PIM and/or the remote devices can also include storage media for storing data such as the storage media described herein.

The PIM 204 may be configured to sense body movement information in response to an impact, which may be indicative of one or more types of motion that may have occurred. The body movement information may be used to determine whether one or more types of impact may have occurred. The one or more types of impacts may include impacts that, for example, cause one or more types of undesirable motions to the brain such as those described herein. For example, the sensed information may be used to determine if an angular acceleration has exceeded a preset threshold, which could be indicative that a brain injury may have occurred. As a result of such an impact, the system may be configured to produce a recommendation that, for example, the individual that sustained the impact should cease participation in the activity until that individual has been examined for a potential brain injury.

The PIM 204 may include one or more sensors to sense the bodily information. The one or more sensors may be accelerometers, gyroscopes, or some other such sensors. In some embodiments, there may be a combination of different types of sensors in the PIM 204 that may be configured to detect body motions and/or impacts. The PIM may include one or more sensors adapted to sense rotational accelerations and may also include one or more sensors to detect linear accelerations. The sensors may be digital or analog sensors. In an example, the PIM 204 may include one sensor to measure 3-axis linear acceleration and one sensor to measure 3-axis rotational velocity. The linear acceleration sensor may be a multi-axis accelerometer, and the rotational acceleration sensor may be a multi-axis gyroscope. In such an example, the linear acceleration sensor and/or the rotational accelerations sensor may be integrated (i.e., configured to sense movement in all three axes) or the sensors may be configured with separate measurements for each of the three axes of movement. In some embodiments the sensors may be integrated for one type (e.g., rotational or linear) of measurement, and/or may be separate for another type of measurement.

In an embodiment, the PIM 204 may include an integral (or removable) printed circuit board with the one or more sensors located on the printed circuit board. Embedded firmware on the printed circuit board may be configured to control the function of the one or more sensors by, for example, reprogramming the firmware.

The PIM 204, using the one or more sensors, may be configured to sense data from the individual associated with the PIM. In some embodiments, the PIM may be configured to sense data associated with and/or related to the detection of one or more types of impact events. For example, the PIM 204 may be configured to sense data associated with head impacts and/or with potential brain injuries. The PIM 204 may also be configured to perform one or more processing operations onboard the PIM before the data is communicated to one or more remote devices for further processing. For example, the PIM 204 may be configured to perform one or more analysis operations. The one or more analysis operations may be configured to measure events of interest (e.g., peak linear accelerations and/or peak rotational accelerations) and select events of interest such as, for example, those whose peak accelerations are above a certain threshold.

The PIM 204 may also include one or more storage devices (e.g., a memory chip) adapted to store raw or processed data from the one or more sensors. The PIM may be adapted to store data that is relevant while not storing data deemed not relevant using, for example, the event selection operations described herein. In such an embodiment, peak accelerations above a threshold can be stored while other accelerations below the threshold are not stored. The stored data may be sent via a wired or wireless communication (e.g., via radio) to a remote device. The stored data may be retained for long-term storage, such as when trying to compile a repository of information and/or may be periodically deleted.

In an embodiment in which 3-axis linear acceleration and 3-axis rotational velocity are measured, six channels of data corresponding to the six axes may be stored for each impact event. In some embodiments the PIM may be configured with additional functionality to, for example, reduce computing requirements for the one or more remote devices that may receive the data. Such additional functionality may include, but may not be limited to, in-device calibration (e.g., offset and gain correction for sensors), rotation of three- and six-axis measurements to a more desirable coordinate system (e.g., the dummy coordinate system specified in standard J211-1 of the Society of Automotive Engineers (SAE)), filtering of waveforms to a desirable characteristic (Channel Frequency Class (CFC) of SAE J211-1), or combinations of these and/or other such functionality. In some embodiments, the described functionality may be performed entirely on the PIM, may be performed partially on the PIM, or may be performed on a device (e.g., a computing device) separate from the PIM.

In an embodiment, the PIM 204 may include an array of linear accelerometers configured to allow characterization of both linear and rotational kinematic variables. In such an embodiment, the PIM 204 may not include a gyroscope. In such an embodiment, the PIM 204 may be configured with an integral or removable printed circuit board with a plurality of linear accelerometers mounted on the printed circuit board. The linear accelerometers may be digital or may be analog. In such an embodiment, a plurality of linear accelerometers may be required, with a mathematical calculation applied to their outputs providing the functionality typically performed by a gyroscope. In such an embodiment, onboard firmware may be configured to calculate rotational motion values based at least in part on the linear accelerations. In such an embodiment, the placement and/or orientation of each of the plurality of linear accelerometers may be required to be known and accurate in order to perform the rotational motion calculations.

In some embodiments, the PIM 204 may be configured to measure both linear acceleration and oral temperature. U.S. Pat. No. 7,481,773, the disclosure of which is incorporated by reference herein. In an embodiment where the PIM is integrated into a mouth guard, the oral temperature may be obtained using an in-mouth sensor that is located in close proximity to the gum, the cheek, or the roof of mouth. The in-mouth sensor may measure the oral temperature due to contact with in-mouth tissue. As the oral temperature is known to typically be lower than core temperature, and because the oral temperature may be affected by breathing, saliva, drinking of fluids, ambient temperature, or other such conditions, processing of the sensor data may be required to determine an accurate core temperature.

In an embodiment, a plurality of temperature sensors may be used so that temperature data is taken from multiple locations, and the temperature readings can be combined to infer a core body temperature. One or more of the plurality of sensors may be configured to measure the ambient temperature by, for example, placing the sensor away from the body and/or in a central location. Additionally, one or more temperature sensors may be placed on, for example, the forehead, the chest, abdomen, etc. of the participant, to gather additional temperature data.

Other biometric measurements may be made using other sensors associated with the PIM 204. For example, the respiration rate of the participant can be measured to help improve the accuracy of the in-mouth (i.e., PIM) temperature measurement as well as to track the breathing of the participant. Other techniques for measuring temperature may include an embedded (on the printed circuit board and/or mounted on the PIM) thermistor, an infrared sensor, a dissimilar metals (bi-metallic) sensor, or other such sensors. In some embodiments the PIM includes a printed circuit board with both an integral accelerometer and a temperature sensor. The temperature sensor may also employ a flexible lead that is mounted in a location of close/intimate proximity to in-mouth tissue for purposes of good thermal coupling. As the accuracy of oral temperature can be affected by breathing, saliva, drinking of fluids, or other such factors, incorporating a secondary sensor to work with the in-mouth sensor may improve the accuracy of the temperature measurement.

In some embodiments, the PIM 204 may have a unique identifier (e.g., serial number) and may also have sensor calibration data associated with that identifier that may be communicated to a receiving remote device such as a host computer. In an embodiment, the PIM may be configured to communicate using wireless communication, wired communication, or a combination of wireless and wired communication. In some embodiments, a remote device may be configured to specify to the PIM the preferred type of communication.

As described herein, the PIM may be configured to identify impact events for communication to the remote device (e.g., to a host computer) such as when those impact events exceed a linear acceleration threshold. Impact events that exceed a threshold may also be referred to herein as "notable impact events" or "harmful impact events." For example, the PIM may be configured such that, when the PIM detects a threshold exceeding event, data indicative of the event is transmitted to the remote device. The data can be raw or processed data and may be stored on the PIM and/or may be communicated to the remote device. In some embodiments, the identified impact events for communication may be a subset of the identified impact events for storage (i.e., the PIM may store more data than it may typically communicate). For example, the PIM may store a history of data from an entire athletic event, retaining a record of all impacts, but may only communicate a subset of that information to the remote device. For each detected event, the PIM may be configured to associate, store, and/or communicate a time value (e.g., a time stamp) associated with the event. One or more impact events may be collected as a set of impact events based on shared impact event parameters such as, for example, impact events that exceed a threshold value. One or more sets of impact events may also be collected as based on shared impact event parameters. For example, a set of impact events may be collected for players playing in the same and/or similar positions on a team. A set of these sets of impact events may be collected to represent the full team, or over multiple games, or based on opponent, or based on some other impact event parameters.

In some embodiments, the PIM 204 may include one or more indicators to provide additional information to participants and/or monitors, such as one or more visual indicators, audio indicators, and/or tactile indicators. For example, a visual indicator may be configured to indicate to the monitor that some action is required. The visual indicator may be any suitable visual indicator, such as one or more LEDs on the PIM, a user interface on the remote device, or some other such indicator. For example, the PIM may activate an LED to indicate charging status and/or may also provide information usable to update an icon (e.g., bar icon) on a user interface indicating the same. The PIM may be configured to activate the visual indicators as instructed by a request received from a remote device such as, for example, a host computer.

The PIM 204 may be configured to allow custom fit of the PIM to the athlete for improved mechanical coupling to head movement. For example, in an embodiment where the PIM is incorporated into a mouth guard, the PIM may include a custom dental impression for a mouth guard PIM, which may be made in a prescribed time period. For example, the impression may be achieved in less than three minutes, less than two minutes, less than one minute, or less than some other such prescribed time limit. Examples of custom-fit mouth guards are described in U.S. Pat. App. Pub. No. 2012/0325224, filed May 27, 2011, which is incorporated by reference herein.

The PIM 204 may include an altimeter that may be configured to determine the height of the PIM above the ground. Such altimeter data may be used to determine the height of the impact above ground and/or to determine the participant height above ground over the course of use of the PIM. In an embodiment, the altimeter data may be used in conjunction with global positioning system ("GPS") data (as described herein) to determine the location of the participant. Location of the participant may be used to, for example, determine information about player position, which may be combined with impact data and used by coaches and players for performance and safety purposes.

In some embodiments, the PIM 204 may include a printed circuit board with an integral barometric sensor (such as, for example, a micro-electro-mechanical system ("MEMS"). The barometric sensor may be a non-sealed barometric sensor so that it has contact with ambient environmental pressure and because the printed circuit board and associated electronics of the PIM should be sealed, the PIM may be configured with a port, opening, or aperture for the sensor. In some embodiments, the port or opening for a barometric sensor may use a membrane that allows air pressure to be measured, but limits the passage of moisture into the electronics. The membrane may be made of Gore-Tex®, or may be made of some other such material that allows for air passage but that limits moisture passage. The port may be located outside of the mouth such that ambient pressure may be accurately measured.

The printed circuit board of the PIM 204 may configured with one or more embedded algorithms that uses the ambient temperature measurement such as the ambient temperature measurement described herein to improve the accuracy of the barometric data. For example, ambient temperature may be determined using a thermistor that is located in a position slightly away from the body. This ambient temperature information and/or the barometric pressure information may also be used to calibrate and/or verify correct altitude information. For example, one of the one or more algorithms may use GPS position to verify altitude location of user, which may be used to improve the accuracy of the barometric measurement, and thus may be used to improve the accuracy of the altitude measurement from the altitude sensor. As may be contemplated, the examples of how sensors may be used in concert to improve the accuracy of measurements described herein are merely illustrative and, as such, other methods for combining sensors to improve accuracy of measurements may be considered as within the scope of the present disclosure.

As described herein, the PIM 204 may include one or more means of data storage, which may be used to store and/or buffer the altitude data. The altitude data may be combined with GPS data and/or impact data and may be transmitted wirelessly to or from a remote device. The combined data may be viewed in conjunction with other data (e.g., video data, GPS data, impact event data) using an impact review system as described herein to analyze and/or improve participant safety, performance metrics, and/or other such factors.

In some embodiments, the data display device 202 associated with the PIM 204 may be a helmet mounted system component acting as an event repeater to a more distant remote device. In such an embodiment, the PIM may communicate with the NFC over a short distance and the NFC may, in turn, rebroadcast the communications received from the PIM to a remote receiver.

In an embodiment where the PIM is adapted to be used on an athletic field, there may be a plurality of pre-positioned antennas next to or adjacent to the field (e.g., one on each of the four corners of an American football field, or positioned around the top of a stadium, or mounted adjacent to goalposts). The plurality of antennas may be used to provide greater accuracy of GPS data for the PIM and may be used to improve performance of the GPS receiver integrated with the PIM. The field antennas may communicate with the PIM based on triangulation, and thus may improve positional accuracy data. In an embodiment, the PIM may be an inertial navigation system whose accuracy is improved by the accuracy of the GPS receivers. The participant positional data thus obtained may be a useful tool for analysis as described herein.

One use of such participant positional information is that it may be used, for example, to play back player actions during the game, and in an embodiment, the GPS-enhanced position data may be displayed in conjunction with video data from the game. The described system may incorporate data from multiple on-body sensors (e.g., multiple PIMs) to improve quality of player position on the field. Impact data may be tied together with player position, player position relative to other players, exact player location on the field during time of impact, the type of plays that are involved with impacts, and other such game-related data. Using GPS enhanced positioning (e.g., from the multiple antennas) may also minimize the time to subsequent fix (a measure of the length of time that it takes a GPS receiver to locate after the first fix) because in an embodiment, a sideline laptop may transmit almanac and ephemeris data over a fast local connection, mimicking the role of a cell tower in cell phone GPS. Such a minimization of time to subsequent fix may use an existing radio connection (e.g., provided by the described system) to provide low latency (and thus more accurate) GPS location determination.

In some embodiments, additional context for positioning may be achieved by adding a game object GPS. An example of this would be a GPS in a football or on another player's equipment. For example, in American football, a play may develop around the activities of a key player such as the quarterback. Impact data relative to the key player may provide additional useful information about an impact. In some embodiments, the PIM may be configured to transmit position of participants and of game objects during the course of an activity. It should be noted that, while the game-related terms "player," "game," and "coach" are used in the present disclosure, each should be understood to include any participant in any activity with any supervisor of such activity unless otherwise explicitly defined or made clear from context. For example, the term "player" may include players of sports, fire and rescue workers, military personnel and/or other such participants. The term "game" may include games, sports, contact sports, fire and rescue situations, military operations, or other such activities. The term "coach" may include coaches, other players, site commanders, incident commanders, officers, platoon leaders, or other such supervisors and/or users of the data.

In some embodiments, the PIM may include a detachable tether with multiple functions. The detachable tether may be made of a flexible, biocompatible material such as Santoprene™ or silicone, which provides a close fit with the mouth guard, and also provides sealing of any external contacts. Sealing of contacts may be beneficial both for user safety perspective (i.e., limiting any possible voltage to the tissue of the user in a non-conforming condition) and also from an environmental protection perspective whereby the tether feature keeps moisture from coming in contact with the conductive contacts.

A PIM may be configured with one or more algorithms providing logic (e.g., by way of a rules engine) for impact classification to reject inaccurate data. A PIM may utilize one or more on-body sensing methods to reject motion artifacts (false impacts) when the PIM is not in a proper position. For example, a PIM may be configured to avoid collection and/or transmission of data resulting from a PIM swinging from a tether as a player walks on or off the field such as when play is not active because the PIM is not properly located within the player's mouth. Such on-body sensing may be achieved by using one or more capacitive or resistive impedance sensors. For example, on-body sensing may be accomplished using a button or switch that is activated when a mouth guard is properly placed in a participant's mouth. As described herein, event selection of the impact data stream (based on user selected criteria) may also be performed by an impact classification algorithm and may also be used to decrease the amount of data collected, transmitted, and/or processed. For example, during a sporting event, a player may receive numerous impacts, the vast majority of which are not cause for concern due to their relatively low magnitude. Classification of movement recorded while the PIM is detected to be on-body may allow motion events to be discarded, devalued, or otherwise caused to become distinguishable from impacts of interest, thereby enabling users to more quickly obtain and analyze relevant data.

A bank charger 206 may be configured to charge one or more PIMs using a wired connection that is configured to provide battery charging of an attached PIM. The bank charger 206 may also be configured to communicate with each of the one or more PIMs using, for example, a USB connection. The bank charger 206 may be connected to a host computer and may be one of a plurality of bank chargers connected to one or more host computers. For example, in an athletic competition, a first bank charger for a first team may be connected to a host computer and a second bank charger for a second team may also be connected to the host computer. PIMs for the first team may be connected to the first bank charger and PIMs for the second team may be connected to the second bank charger. In an embodiment, the wired contacts of the bank charger may be sealed against moisture intrusion using, for example, a gasket, enclosure, or membrane. PIMs may be scoured in the bank charger using a retaining mechanism to prevent movement and/or disconnection of the PIMs during transport.

A bank charger enclosure 208 is an enclosure for one or more bank chargers such as the bank charger 206. A bank charger enclosure 208 may be configured to sanitize PIMs using, for example, ultraviolet light, sanitizing chemicals, heat, or some other such method of sanitization. A bank charger enclosure 208 may also be configured to minimize cross-contamination from sanitizing solutions which may be applied to other PIMs stored within the enclosure such as, for example, using an inverted "stair-case" configuration such that PIMs are stored in horizontally staggered rows. A bank charger enclosure may also be configured with ventilation (e.g., a fan and/or multiple openings) to facilitate long-term storage of the PIMs.

A monitoring station receiver 210 may be a radio frequency antenna, a wireless internet receiver, or some other such communications device configured to receive and/or retransmit data from one or more PIMs. In an example described herein in connection with FIG. 18, the monitoring station receiver is a directional antenna that may be placed in proximity to a location wherein one or more PIMs are in use. Data from the PIMs may be received by the directional antenna and may then be amplified and relayed to the monitoring station 212 for storage and/or processing. Data from the monitoring station receiver 210 may be relayed to the monitoring station 212 using wired communications, wireless communications, or a combination of wired and wireless communications.

A monitoring station 212 as described herein may be a laptop, tablet, workstation, or some other such device. The monitoring station may be portable such as, for example, by being incorporated into a case, table, or rack and may include handles, wheels, slides, or other such features to improve such portability. In an embodiment, the size of the monitoring station may be limited by portability factors. The monitoring station may include an integrated or separate communications device such as, for example, an optical communications receiver and/or transmitter or radio frequency communications antenna. The monitoring station may include a surface on which to place a computing device and may include a privacy screen configured to restrict and/or reduce the ability of others to view one or more displays associated with the computing device. The privacy screen may also be configured to shield the computing device and/or the computing device displays from sunlight, ultraviolet light, heat, rain, moisture, snow, or other such weather and/or environmental effects.

The monitoring station 212 may be configured to incorporate one or more of the system components described herein including, but not limited to, one or more bank chargers, one or more bank charger enclosures, one or more storage areas for personal impact monitors, bank chargers, bank charger enclosures, or near-field data display devices, or other such system components. The monitoring station 212 may be configured with mounting areas for antennas and/or receivers such as, for example, the monitoring station receiver 210. The monitoring station 212 may also be configured with power supplies, auxiliary power supplies, batteries, solar panels for charging devices, or other power supplying components.

A remote notification device 214 is a device that may be wearable by a coach, supervisor, commander, physician, player, or some other such person. The remote notification device 214 may be, for example, a wristband, a headset or earpiece, a device that clips to clothing, or a pendant that can be worn around the neck. The remote notification device 214 may be configured to provide one or more impact event notifications including, but not limited to, a visual notification, an audio notification, a tactile notification (e.g., vibratory), when the remote notification device is activated by a remote system device such as a monitoring station. The remote notification device may also include an input (e.g., a button that may be pushed) that is configured to at least provide an acknowledgement of the activation. The acknowledgement may be sent to the activating remote device using, for example, radio frequency, wireless, or optical communication. In some embodiments, the remote notification device may be configured to display impact event data (as translated from the monitoring station and/or computer) and/or other such data related to a notification event.

In addition to the capabilities described herein, each of the components illustrated in FIG. 2 may be configured with additional functionality to support asset management of those components. For example, a PIM 204 may be configured to enter a "Find Me" state that can be entered and/or exited using, for example, a remote device or a near-field data display device described herein. The "Find Me" state may be configured to provide an audio, visual, or tactile indication (e.g., a flashing light, a noise, or a mechanical motion) on the PIM. The "Find Me" state may also be configured to communicate an identifier, positional information, or other such information to a requesting system device. The "Find Me" state may be configured to communicate a unique device identifier (e.g., a serial device serial number) to the requesting system component. In an embodiment, the "Find Me" state may be configured to communicate data associated with the "Find Me" state to other system components instead of and/or in addition to the requesting system component. As may be contemplated, the example of asset management described herein is merely illustrative and other such asset management functions associated with the components illustrated in FIG. 2 may be considered as within the scope of the present disclosure.

Figure 3:
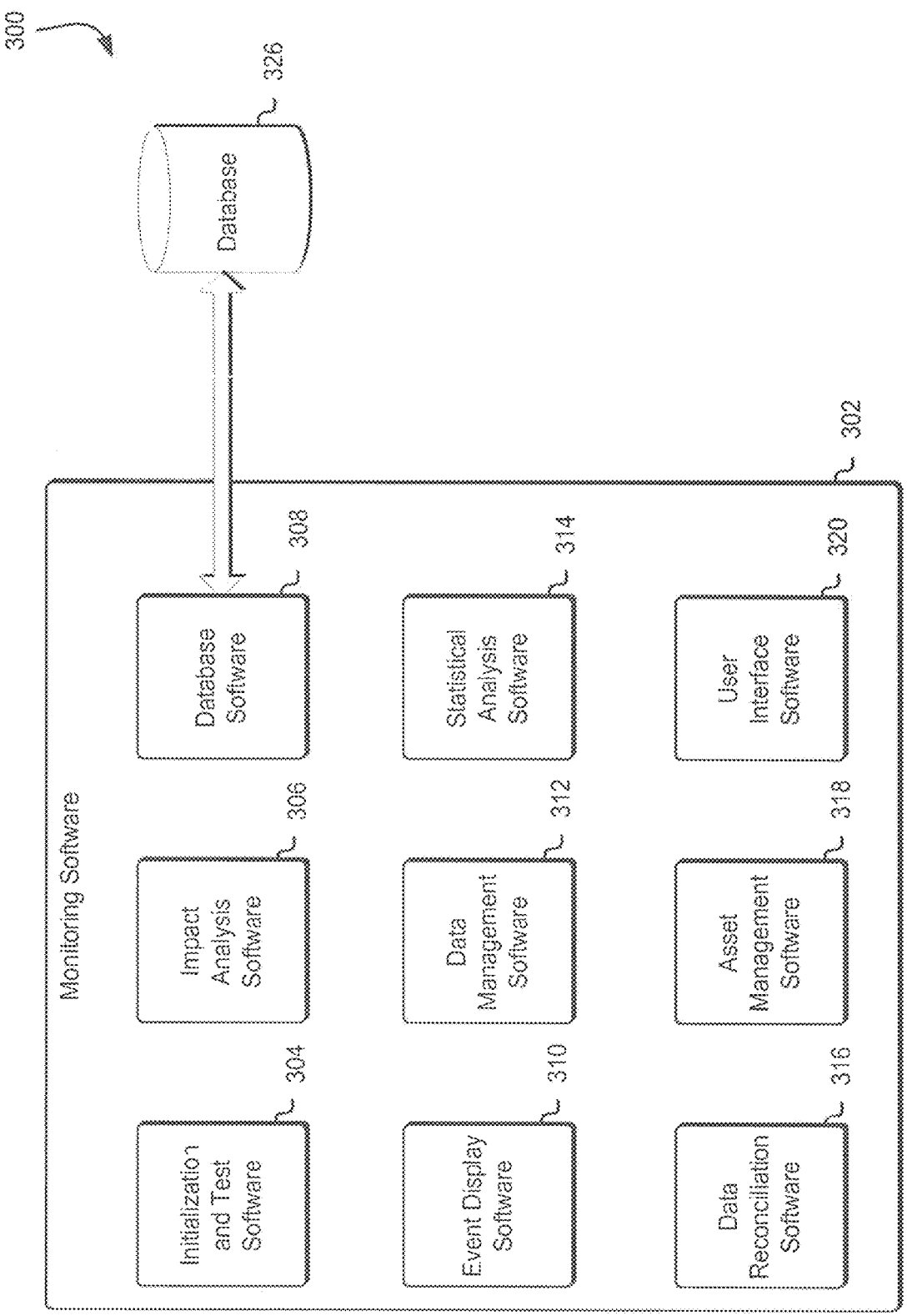
FIG. 3 illustrates an environment where software and applications associated with a personal impact monitoring system may operate in accordance with an embodiment.

FIG. 3 illustrates an example environment 300 where monitoring software and applications associated with a personal impact monitoring system may operate with a system as described herein in connection with FIGS. 1 and 2 and in accordance with an embodiment. The monitoring software 302 may be the same as the monitoring software 216 described herein in connection with FIG. 2. The monitoring software 302 may include one or more software components including, but not limited to, initialization and test software 304, impact analysis software 306, database software 308, event display software 310, data management software 312, statistical analysis software 314, data reconciliation software 316, asset management software 318, or user interface software 320. The various software components may connect or communicate with each other and/or may also connect or communicate with additional components such as, for example, one or more databases 326. Each of the monitoring software 302 components is described in more detail below.

The initialization and test software 304 may be application software residing on a host computer and/or on some other device. The initialization and test software 304 may be configured to communicate with at least one PIM using a first type of communication (e.g., wired), and may also be configured to communicate with the PIM device using a second type of communication (e.g., wireless). The initialization and test software 304 may test the functionality of the one or more communication types by, for example, making a communication request to the PIM via a first type of communication (e.g., wired communication) that must then be answered by a second type of communication (e.g., wireless communication).

The initialization and test software 304 may also instruct the PIM to activate visual indicators to indicate that active communication exists between the application and the PIM. The initialization and test software 304 may also be configured to provide an indication to the PIM that active communication does not exist for the one or more communication types. The initialization and test software 304 may request, receive, and store identifying information from a PIM (e.g., serial number). The initialization and test software 304 may be configured to request, receive, and store calibration information from the PIM such that it can be retrieved by its identifying information. The initialization and test software 304 may also be configured to request that the PIM perform functional testing of functionality associated with the PIM, receive the results, and store the results such that they can be retrieved by other system components using, for example, the identifying information of the PIM. The initialization and test software 304 may also be configured to perform additional initialization and/or testing steps associated with the personal impact monitoring system.

The impact analysis software 306 may be application software residing on (i.e., executed by) a host computer or other remote device. The impact analysis software 306 may be configured to perform (i.e., when executed causes the executing computer system to perform) one or more impact event analyses to analyze one or more aspects of an impact. The impact analysis software 306 may, for example, receive one or more types of data that may be sensed by the one or more sensors in a PIM. One or more aspects of the impact analysis software 306 may be configured to operate in one or more of the system components and/or other devices described herein. The one or more system components and/or other devices may include, but may not be limited to, a PIM, a remote device, a mouth guard, a helmet, a wristband, or a host computer. The impact analysis software 306 may be configured to operate on any device with any suitable type of processing component. The steps associated with the impact analysis software 306 may also be performed on a plurality of different system components.

To provide some background for the functionality associated with the impact analysis software 306, the recent discovery of Chronic Traumatic Encephalopathy ("CTE") and resulting increase of awareness regarding concussion injury have created a need for measurement systems capable of recording impact information during contact sports and other activities that expose individuals to a risk of traumatic brain injury. Current measurement and analysis of such impact may be limited to measurements taken at the location of motion sensors, with no ability to calculate motion at the likely points of injury. The impact analyses performed by the impact analysis software 306 may not be well related to the mechanisms of the associated injury. Such impact analysis also may not be specialized to people with different head and brain geometries. Such impact analyses may also be limited by the fact that the parameters presented as indicative of potential injury are dependent on the bandwidth of the measurement system and may not be compared from one measurement system to another. To address these issues, impact analyses performed by the impact analysis software 306 may be needed that can be customized to the physical properties of an individual, that can provide information relevant to injury mechanisms, that can provide information on the potential for traumatic brain injury throughout the extent of the head, not just at the point of measurement, and/or that can provide summary measurements that are largely independent of measurement system properties.

As an example of the fourth limitation described above, peak linear acceleration magnitude is often studied as a predictor of traumatic brain injury but this measurement is highly dependent on the frequency characteristics of the measurement system and cannot be compared between different products. To illustrate this frequency characteristic dependency, consider a Gaussian shaped impact with half-width (half duration) of 0.3 milliseconds and peak magnitude of 100 g. In a system with a bandwidth of, for example, 300 Hz, with a sampling frequency of 600 Hz, a sample would be taken every 1.667 milliseconds and thus, such a system is unlikely to correctly measure the peak amplitude, the onset, or the conclusion of the impact. Such a system may, for example, provide a Gaussian shaped impact of much lower magnitude than the actual peak value. Similarly, in a system with a bandwidth of, for example, 150 Hz, with a sampling frequency of 300 Hz, a sample would be taken every 3.333 milliseconds. In some systems, the peak amplitude measured by the 600 Hz system may be double that measured by the 300 Hz system, and both may be a fraction of the actual peak amplitude.

It is important to note that neither of the peak value measurements is incorrect, but rather that each value is a property of the associated measurement system. This is illustrated by the fact that generally, while the measured peak amplitudes of different systems vary widely, the area under each Gaussian curve for each may be nearly identical. However, because of this discrepancy in bandwidth, the peak acceleration measured with one system may not be directly compared to the peak acceleration measured by another with any accuracy. To understand the discrepancy it is necessary to have a thorough understanding of the measurement system bandwidth, but this is information that is rarely published by manufacturers or considered in the medical literature. Therefore, for the purpose of studying injury thresholds, it is important to adopt impact metrics such as the area under the acceleration curve (described herein) that consider the time-course of an impact and are largely independent of system bandwidth.

To further provide some background for the functionality associated with the impact analysis software 306, it may be necessary to have some understanding of the physiological structure of the brain. A brain (including the cerebral cortex) is surrounded by brain membranes (dura mater, arachnoid, and pia mater), vessels, and the skull. The membranes, which together are known as the meninges, are pliable but thin, providing minor cushioning for the brain in the event of an impact. The cerebral spinal fluid ("CSF") that fills the subarachnoid cavity provides some additional cushioning. The brain is loosely anchored within the skull by cerebral veins running through the dura mater and branching into both the skull and the cerebral cortex via the other layers of the meninges and subarachnoid space. Rotation of the brain within the skull is further constrained by bony structures on the inside surface of the skull that conform to the brain's shape, and by the brain stem's connection to the spinal cord.

When the human head sustains a direct impact normal (i.e., perpendicular) to the skull surface, the skull may be rapidly accelerated toward the cerebral cortex of the brain. The inertia of the brain may cause the membranes of the meninges to be compressed and CSF to be displaced. If the displacement of the skull caused by the acceleration is large enough and fast enough it will impact the cerebral cortex with a force sufficient to cause focal injuries such as contusions (bruising) and intra-cerebral hematomas.

When the human head experiences a tangential acceleration (e.g., caused by a glancing blow), the skull may rotate quickly. The cerebral attachments to the meninges and skull are stretched as they pull the brain along and sheer stresses are induced within the bulk of the brain matter. Concussion and diffuse axonal injury ("DAI") are believed to result when rotational acceleration is a significant component of the injury mechanism, while vascular stretching may contribute directly to perivascular injury such as that observed in cases of CTE.

While large linear and/or rotational acceleration may be contributing factors in traumatic brain injury by the mechanisms discussed, such acceleration may not be sufficient. A high acceleration maintained for a very short period of time may not generate enough displacement of the skull to cause collision with the cerebral cortex, or significant stretching of the cerebral attachments to the meninges. Therefore, both duration and magnitude of linear and rotational accelerations are important aspects of the injury mechanism.

The impact analysis software 306 may be configured to operate within and/or in conjunction with any of the system components, or modified version thereof, described herein and/or described in U.S. Pat. App. Pub. No. 2011/0179851; U.S. Pat. App. Pub. No. 2011/0181418; U.S. Pat. App. Pub. No. 2011/0181419; U.S. Pat. App. Pub. No. 2011/0181420; U.S. Pat. App. Pub. No. 2011/0184319; U.S. Pat. App. Pub. No. 2011/0184663; and U.S. Pat. App. Pub. No. 2012/0210498, the entire disclosures of which are incorporated by reference herein. For example, the impact analysis software can be configured to operate within and/or in conjunction with any of the mouth guards described in any of the aforementioned applications.

For example, the impact analysis software 306 may be configured to apply PIM specific calibration data to sensor measurements obtained from the particular PIM to obtain calibrated measurements. The impact analysis software 306 may also be configured to receive and/or analyze sensor data from one or more sensors associated with a PIM attached to a part of the body. In such an analysis, the combination of body part where the PIM is attached, other rigidly attached body parts between the body part and the brain, and the PIM may be modeled as, for example, a kinematic rigid body (e.g., mouth guard rigidly attached to skull by application to the upper jaw). The impact analysis software 306 may facilitate analysis by translating measurements made by the PIM to kinematic variables within the body part using the application of rigid body kinematics. The impact analysis software 306 may facilitate analysis based at least in part on measurements associated with one or more kinematic variables including, but not limited to, linear displacement, linear velocity, linear acceleration, rotational displacement, rotational velocity, or rotational acceleration.

The impact analysis software 306 may also facilitate analysis based at least in part on a mathematical model of the brain geometry wherein the locations within the body are mapped to the surface of the brain using the mathematical model of the brain geometry. The impact analysis software 306 may also facilitate analysis based at least in part on a mathematical model of the skull geometry wherein the locations within the body are mapped to the surface of the skull using the mathematical model of the skull geometry. In such analysis, the mathematical model of brain geometry and/or the mathematical model of the skull geometry may be individualized by measuring a specific participant's head geometry and applying corresponding mathematical transformations to the brain geometry model (e.g., by Talairach coordinate or Montreal Neurological Institute ("MNI") space transformations). In an embodiment, the region of interest of the mathematical model of the skull geometry may be limited by those points on the interior surface of the skull and/or are on the exterior surface of the brain.

The impact analysis software 306 may use kinematic variables, including kinematic variables translated by individualized geometries, to calculate one or more properties associated with an impact. For example, the impact analysis software 306 may calculate the maximum linear acceleration (e.g., magnitude and/or direction of the linear acceleration) over the inside surface of the skull. The impact analysis software 306 may also calculate the magnitude of linear acceleration normal (perpendicular) to the inside surface of the skull. The impact analysis software 306 may also calculate the magnitude of linear acceleration tangential (at a right angle) to the inside surface of the skull. The impact analysis software 306 may also calculate one or more strain values and/or one or more sheer values associated with the impact as applied to soft tissue within the brain. In an embodiment, the impact analysis software 306 may use kinematic variables, including kinematic variables translated by individualized geometries, to calculate derived properties of an impact over time (e.g., the normalized energy transferred to the rigid body by an impact, which may be determined by:

$$\frac{E}{m} = \int \overline{a} \circ \overline{v}\, dt,$$

where E/m is the normalized transferred energy, $\overline{a}$ is the linear acceleration vector, v is the linear velocity vector, and t is time. As may be contemplated, the calculations that may be performed by the impact analysis software 306 using kinematic variables, including kinematic variables translated by individualized geometries described herein, are merely illustrative examples and other such calculations may be considered as within the scope of the present disclosure.

The database software 308 may be configured to access a local or remote (e.g., network-attached, virtual, cloud-based, or hosted) storage device for impact data and/or personal information associated with the participants. The impact data and/or personal information associated with the participants may be stored in, for example, a database 326 that may be configured as described herein. The database software 308 may also be configured to access additional databases that may provide additional information required by the personal impact monitoring system. The database software 308 may provide data services to one or more of the monitoring software 302 components.

The event display software 310 may request and/or receive impact data and/or impact analysis data and may present that data on a display that may be associated with one or more of the personal impact monitoring system components. The presented data may include, for example, impact data from a PIM and/or impact analysis data from impact analysis software 306. The event display software 310 may be configured to display the direction and magnitude of maximum linear acceleration on a rendering of a human head as described herein. The event display software 310 may be configured to display the magnitude of maximum linear acceleration normal to the inside surface of the skull on a rendering of a human head as a contour plot, heat map, and/or other such means of displaying three-dimensional information on a two-dimensional surface. The event display software 310 may be configured to display the magnitude of maximum linear acceleration tangential to the inside surface of the skull on a rendering of a human head as a contour plot, heat map, and/or other such means of displaying three-dimensional information on a two-dimensional surface.

In an embodiment, an indicator of impact strength can be displayed on a time line. The indicator can be one or more of maximum linear acceleration, maximum linear acceleration normal to the inside surface of the skull, maximum linear acceleration tangential to the inside surface of the skull, and a measure of energy transferred to the head by the impact. The time line can span one portion of an activity (i.e., a play of a sporting event), a complete activity (i.e., one sporting event), or multiple activities (i.e., multiple sporting events).

The event display software 310 may be configured to allow the setting of impact alert thresholds. Impact alert thresholds may be applied to one or more impact measurements. For example, a lower threshold may be set such that an impact below the lower threshold may be recorded to the database but impact information may not be displayed; an impact above the lower threshold, but below a higher threshold may be recorded to the database and summary impact may be displayed; and an impact above the higher threshold may cause an alert to be activated and detailed impact information to be displayed. The alert may, for example, activate a remote notification device. The alert may also highlight the impact information and/or participant in an event display. Impact thresholds may be globally established and are applied to all participants unless overridden. Custom thresholds may also be set for individual participants and override the global thresholds for those participants.

In some embodiments, the software is configured to set compliance limits, which can be a maximum limit, a minimum limit, or a combination of maximum limits and minimum limits. Compliance limits may be set individually for each player and they may be set according to a variety of different compliance information such as, for example, concussion protocols established by a league. The event display software 310 may be configured to display compliance information (e.g., violation of previously configured impact limits). The compliance information may be based at least in part on time-in-play, number of impacts, frequency of impacts, a cumulative measure of impact strength received, or direction of impacts. The compliance information may also be based at least in part on, for example, whether or not a concussion assessment has been performed in response to impact information. The event display software 310 may also be configured to determine which compliance information to display. The software can also display real-time compliance information.

The event display software 310 may be configured to display athletic performance metrics. The metrics may be displayed as an observed value, or a relative value with respect to an established norm, e.g., team average, median, or other rank order statistic. The event display software 310 may be configured to show the number and strength of impacts in an activity, a single event, or over multiple events and activities. The event display software 310 may be configured to display metrics that encourage safety (e.g., number of impacts divided by maximum impact strength). The event display software 310 may be configured to display performance metric statistics for an entire group of participants (e.g., a team), or for a subset of the participants (e.g., defensive, offensive, special teams, etc.). The event display software 310 may be configured to display individual outliers compared to a norm (e.g., a player with multiple impacts of strength greater than the team's 90th percentile, or greater than two standard deviations above the mean, or based on some other metric).

The event display software 310 may be configured to display undesirable athletic behavior, such as, for example, a specified head orientation during impact, a direction of impact relative to the head, a strength of impact, a rate of impacts per time-in-play, or events that may be identified as outliers compared to a norm (e.g., a player with multiple impacts of strength greater than the team's 90th percentile, or the league's 90th percentile). The event display software 310 may be configured to provide a time stamp of occurrence for undesirable athletic behavior. The event display software 310 may also be configured to superimpose undesirable event information on a review video of game play.

The event display software 310 may be configured to receive impact data and/or impact analysis results from multiple PIM attached to a single athlete so as to identify mechanical body relationships that pose a health risk (e.g., spine compression or extension, head twisting, or joint hyper-extension). In some embodiments, the PIM device can be attached to either side of a joint so as to identify specific injuries. For example, a joint hyper-extension in the knee may be detected by excessive anterior translation and medial rotation of the tibia in relation to the femur that can cause tearing of the anterior cruciate ligament ("ACL").

The data management software 312 may be configured to receive information about impacts from a monitoring station receiver or from a PIM and may be configured to transfer such data to the impact analysis software 306, to the database software 308, or to some other software system of the monitoring software 302. The data management software 312 may also be configured to receive results from those and/or other software systems. The received data and/or the results may then be stored in a data storage medium (e.g., a persistent storage medium), retrieved from a data storage medium, communicated to a remote notification device, prepared for storage in a database, or managed in some other such manner.

In some embodiments, the data management software 312 may be configured to select data such that, for example, only data that meets configured criteria (e.g., an impact greater than a configured threshold) is transmitted or only the occurrence of an impact event is transmitted but the impact event data is not. Different data and/or different data paths (destinations and/or sources) may dictate how the data is selected. For example, in some embodiments, components of the monitoring software may be configured to record compliance information (e.g., athlete play time, administration of cognitive assessment following an impact, or the results of that cognitive assessment). In such embodiments the monitoring software may be configured to alter and/or adjust compliance requirements and the data management software 312 may be configured to select data based on these compliance requirements. As may be contemplated, the methods that data and/or results may be selected for data management by the data management software 312 described herein are illustrative examples and other methods that data and/or results may be selected may be considered as within the scope of the present disclosure.

The statistical analysis software 314 may be configured to perform statistical analysis of the impact data, either in real-time or near real-time or as part of a post-hoc analysis to enable discovery of long-term trends, analyze individual participant data over different time scales, or to inform the establishment of personalized thresholds for alerts. Such trends, also referred to herein as "statistical measurements" may be used to characterize one or more variables associated with the statistical analysis system. Additionally, the statistical analysis software 314 may be configured to identify problematic participants that would benefit from additional training or coaching, and small groups (e.g., teams) that are out of compliance with larger organization (e.g., conference or league) goals.

The statistical analysis functions described herein may be available using conventional statistical analysis software packages, but few of the users of this disclosure will have formal training in statistics or the use of such statistical analysis software. The statistical analysis software 314 may therefore be configured with pre-programmed analyses for specific tasks relevant to the management and analysis of impact information with statistical tests pre defined to present the analysis and to provide the results in a non-technical manner. The statistical analysis software 314 may also be configured to perform an outlier analysis on a small population, using large population statistics (e.g., from multiple activities) so that outlier events may be identified by, for example, comparing an impact measurement to personal measurements, team measurements, or league measurements. Outlier analysis may be useful, for example, in identifying risky behavior that might be corrected by additional training or coaching.

The types of statistical analyses that may be performed by the statistical analysis software 314 may include parametric impact statistical analyses (i.e., a parameter of a probability distribution representative of the observed data such as mean or variance for a normal distribution, non-parametric impact statistical analyses (e.g., a rank or order statistic), or computational statistical analyses (e.g., by bootstrap or permutation). The statistics may be used to characterize frequency of impact or magnitude of impact. The magnitude may be of the component normal to a rigid surface of impact (e.g., the skull interior) or tangential to a rigid surface of impact (e.g., the skull interior) The statistics may also be used to characterize linear acceleration magnitude, which can be the component normal to the interior surface of the skull, or the component tangential to the interior surface of the skull. The statistics may also be used to characterize rotational acceleration magnitude. The statistics may also be used to characterize derived properties of an impact over time (e.g., head injury criterion ("HIC"), or impact energy ("IE") as defined herein. The statistics may also be used to characterize sheer of brain tissue or strain of brain tissue.

The statistical analysis software 314 may be configured to compare one or more impact statistics for an individual or group of individuals to a population norm so as to identify unusual (outlier) impact incidence and/or severity. The population norm may be calculated across a small group (e.g., a team), across larger group (e.g., a conference or league), or across one or more individuals with a similar probability of impact (e.g., within the same team responsibility (position) in a sporting environment).

The statistical analysis software 314 may be configured to allow the selection of specialized analyses, such as an analysis that provides information on exposure to potentially injurious impacts, an analysis that provides information on performance improvement related to a defined task (e.g., sporting performance), or an analysis that provides information on behaviors that may expose the participant to unnecessary risk and that may be corrected by modifying the circumstances or behavior of the participant.

A specialized analysis may be performed that compares an individual or group to a larger group (e.g., a troop compared to platoon, an athlete compared to a league, an athlete compared to all league athletes having the same position of play). A comparison may be performed to check for differences according to well-established parametric statistical tests that are appropriate to the data type and populations (e.g., a student's t-test). A comparison may be performed to check for differences according to well-established non-parametric statistical tests that are appropriate to the data type and populations (e.g., a Wilcoxon-Mann-Whitney test). A comparison may be performed to check for differences according to well-established computational statistical tests that are appropriate to the data type and populations (e.g., a bootstrap test). A comparison may be performed to identify the number or percentage of outliers in a smaller group when compared to the distribution of a larger group. The populations and statistical tests may be automatically selected and executed by the analysis software according to its specialized purpose. The resulting analysis may be displayed in a context that is separate from other analyses, such as within a software window, in a software panel activated by selecting a tab icon, or in written report. The analysis may also be used to provide recommendations for action.

The data reconciliation software 316 may be configured to reconcile data used by the personal impact monitoring system by accessing event data stored on a PIM and by accessing event data stored by the data management software 312 and comparing the two. The data reconciliation software 316 may, as part of this analysis, store such data onto one or more persistent storage devices. The data reconciliation software 316 may be configured to compare data stored on a PIM to data stored by the data management software 312 in order to ensure data consistency and may flag inconsistent data and/or attempt to reconcile data inconsistencies by performing one or more operations on the inconsistent data.

The data reconciliation software 316 may also be configured to communicate data from a PIM to the data management software 312 for storage on the one or more persistent storage devices as part of the data reconciliation process. The communicated data from the PIM may be comprised of, for example, impact events that were not successfully communicated by wireless means. The data reconciliation software 316 may also be configured to access notifications received by the personal impact monitoring system regarding data stored on a remote notification device, as well as notifications of data sent to be stored by the data management software 312 on the one or more persistent storage medium devices. The data reconciliation software may compare data stored on a remote notification device to data stored by the data management software in order to assess notification success rate.

The asset management software 318 may be configured to request that a device (e.g., a PIM) enter a "Find Me" state as described herein. The "Find Me" state may cause the PIM to provide some indication such as, for example, a tactile indication that may then allow the PIM to be located. The asset management software 318 may be configured to activate any of the system components described herein and may also be configured to receive responses from any of those system components such as, for example, responses that may include data such as location information of those system components. The asset management software may also be configured to receive unique device identification information from the "Find Me" data and associate it with a known system component from a system component roster or inventory.

The user interface software 320 may include user interfaces showing one or more aspects of a personal impact monitoring system. One or more user interfaces are described herein in connection with FIGS. 23 to 27.

Figure 4:
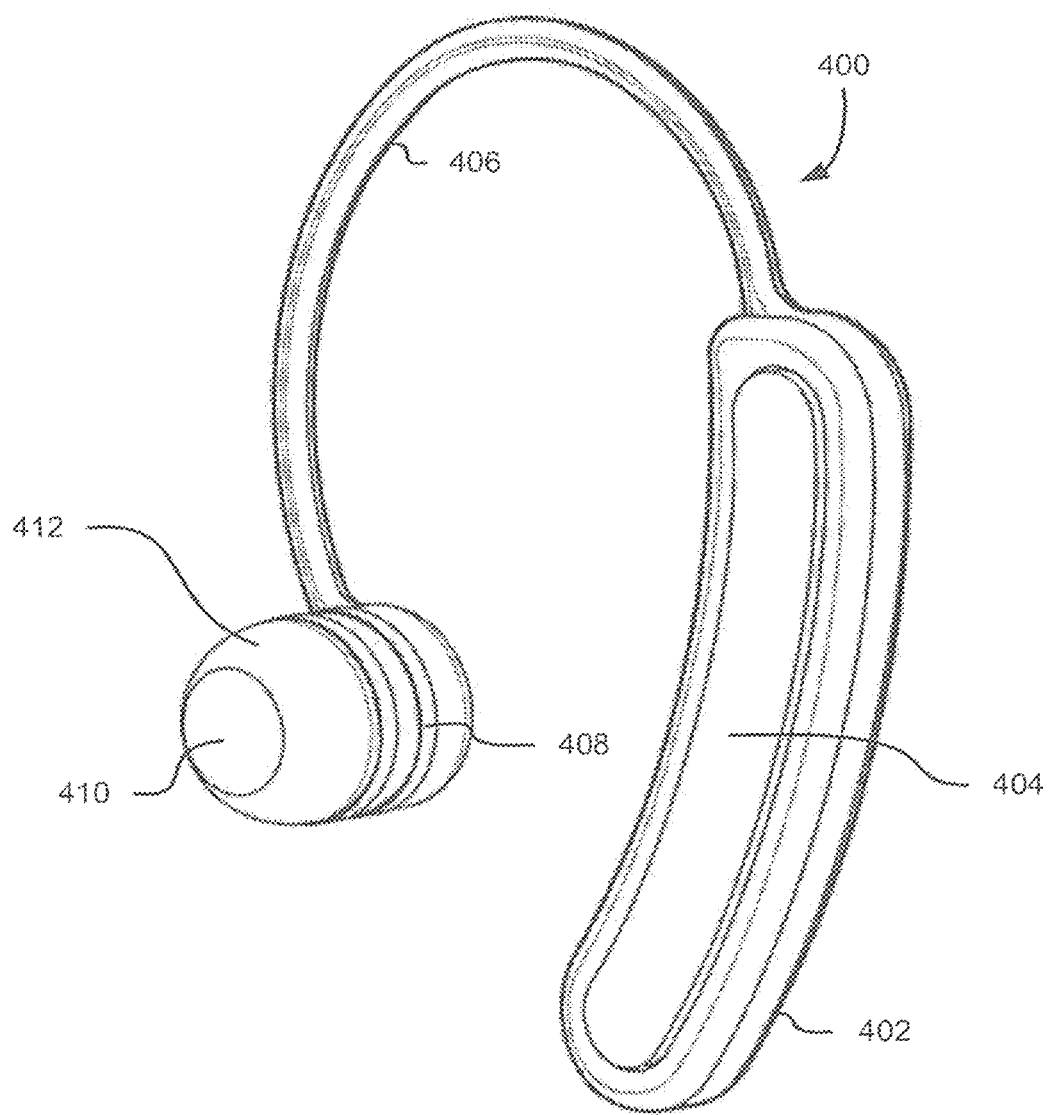
FIG. 4 illustrates a personal impact monitor in accordance with an embodiment.

FIG. 4 illustrates an example PIM 400 for use with a personal impact monitoring system as described herein in connection with FIG. 1 and in accordance with an embodiment. The example PIM 400 illustrated in FIG. 4 is an ear-mounted personal impact monitor with an electronics package 402, a pad 404 which may be an adhesive pad, a flexible connector 406, and an earpiece 412 which may include one or more sensors 408 around a hollow section 410 so that the hearing of the wearer is not impaired by the PIM.

Figure 5:
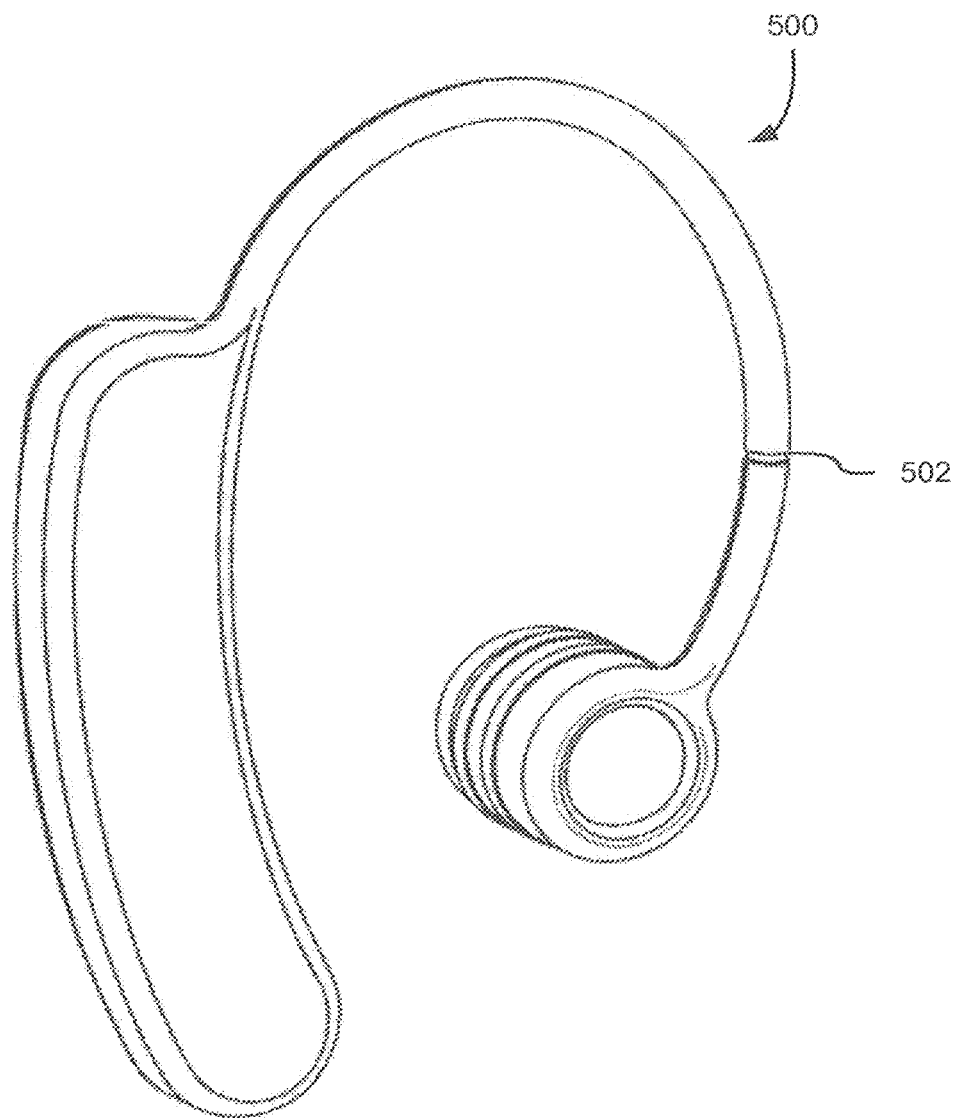
FIG. 5 illustrates a personal impact monitor in accordance with an embodiment.

FIG. 5 illustrates an alternative embodiment of a PIM 500 for use with a personal impact monitoring system as described herein in connection with FIG. 1 and in accordance with an embodiment. The example PIM 500 illustrated in FIG. 5 includes a pivot section 502 which may aid in the proper placement of the PIM 500 while still maintaining a connection with the electronics illustrated in connection with FIG. 4.

In some embodiments, the PIM 400 and/or the PIM 500 may be sized and configured to be a removable, wearable electronics package. The electronics in the electronics package may include components and features disclosed herein, including without limitation one or more of the following: a processor, radio, antenna, accelerometer, gyroscope, altimeter, magnetic compass, GPS sensor, and OPS radio. FIG. 4 and FIG. 5 illustrate an example of an earpiece PIM that is adapted to be secured to an individual's ear. The earpiece embodiment provides for a repeatable placement location on the head (i.e., in the ear), which may be difficult to accomplish with skin patch devices, for example, where an anchoring landmark or point of reference may not be available. The earpiece derives positional reference from the ear, both via the external auditory canal and the helix and lobule. Since it can be a stand-alone device, this PIM may also be used for non-helmeted applications, such as soccer. The repeatability of placement may provide the benefit of improved algorithm accuracy with respect to translation of linear velocity and acceleration to positions on and within the brain and skull. The earpiece may be sealed and easily cleaned. The antenna and radio electronics in the electronics package may also be placed high on the body and are in clear air (i.e., not in mouth or otherwise obstructed).

The earpiece of the PIM 400 and/or the PIM 500 may be adapted to be inserted into the car cavity via the generally cylindrical feature as shown. The earpiece may be adapted to be a left or right ear version according to the orientation of the insertable component. In some embodiments, the insertable component may be adapted to be rotated by approximately 180 degrees around the pivot section 502, thus allowing the earpiece to be inserted into either ear.

In an embodiment, the earpiece of the PIM 400 and/or the PIM 500 may incorporate a microphone external to the car and an audio reproduction transducer within the ear insert that is in acoustical communication with the ear. In this way the ear insert may seal the ear canal without adversely affecting hearing. In addition, audio information may be received remotely (e.g., by radio communication from a sideline coach) and this audio information may also be communicated to the wearer via the audio reproduction transducer.

In the examples illustrated in FIGS. 4 and 5, the car insert may be a pliable, contoured exterior feature for comfort. It may be, for example, made of silicone, which is both biocompatible and cleanable. It may also include one or more radially deployed conductive sensors, capable of one or more body measurements (e.g., heart rate, body temperature) via contact with the external auditory canal. The earpiece may also include conductive sensors that are made of a conductive, metallic, biocompatible material suitable for measurement/sensing (e.g., stainless steel, platinum, or titanium). Additionally, the earpiece PIM may include one or more non-conductive sensors capable of body measurement via non-contact means, such as pulse measurement by tympanic pulse oximetry, or body temperature by infrared thermometry.

The earpiece of the PIM 400 and/or the PIM 500 may be secured against the head with a flexible connector 406 that can be fitted and easily customized to the wearer's ear. Additionally, the PIM may include an optional adhesive patch located on the inside of the electronics module that makes contact and adhesion with the skin of the wearer. The adhesive patch may be removable and replaceable such that new adhesive may be installed on a periodic basis as required by the wearer. Examples of adhesive suitable for this application may include, but may not be limited to, Mactac® TM6563, Mactac® TM-5300, and 3M® 9926.

In some embodiments, the earpiece may include an electronics module that may include one or more printed circuit board assemblies ("PCBAs"). The PCBAs may include the core electronics and/or the antenna for the PIM 400 and/or the PIM 500. A micro cable assembly may be located within the flexible section and may extend through the flexible section. The micro cable may connect the electronics module to the in-ear sensors and transducers. One or more PCBAs may be mounted in the insert or in the external portion of the PIM 400 and/or the PIM 500.

The PIMs described herein may be adapted to sense and/or monitor one or more physiological indications of the participants, including but not limited to, body temperature, blood pressure, heart rate, and/or respiration rate. Additionally, the personal impact monitoring system may be configured to receive alerts from any of these or from other physiological monitors if, for example, the sensed indication is above and/or below a threshold. In some embodiments, the PIM may also include a piezo tube configured to monitor respiration.

Figure 6:
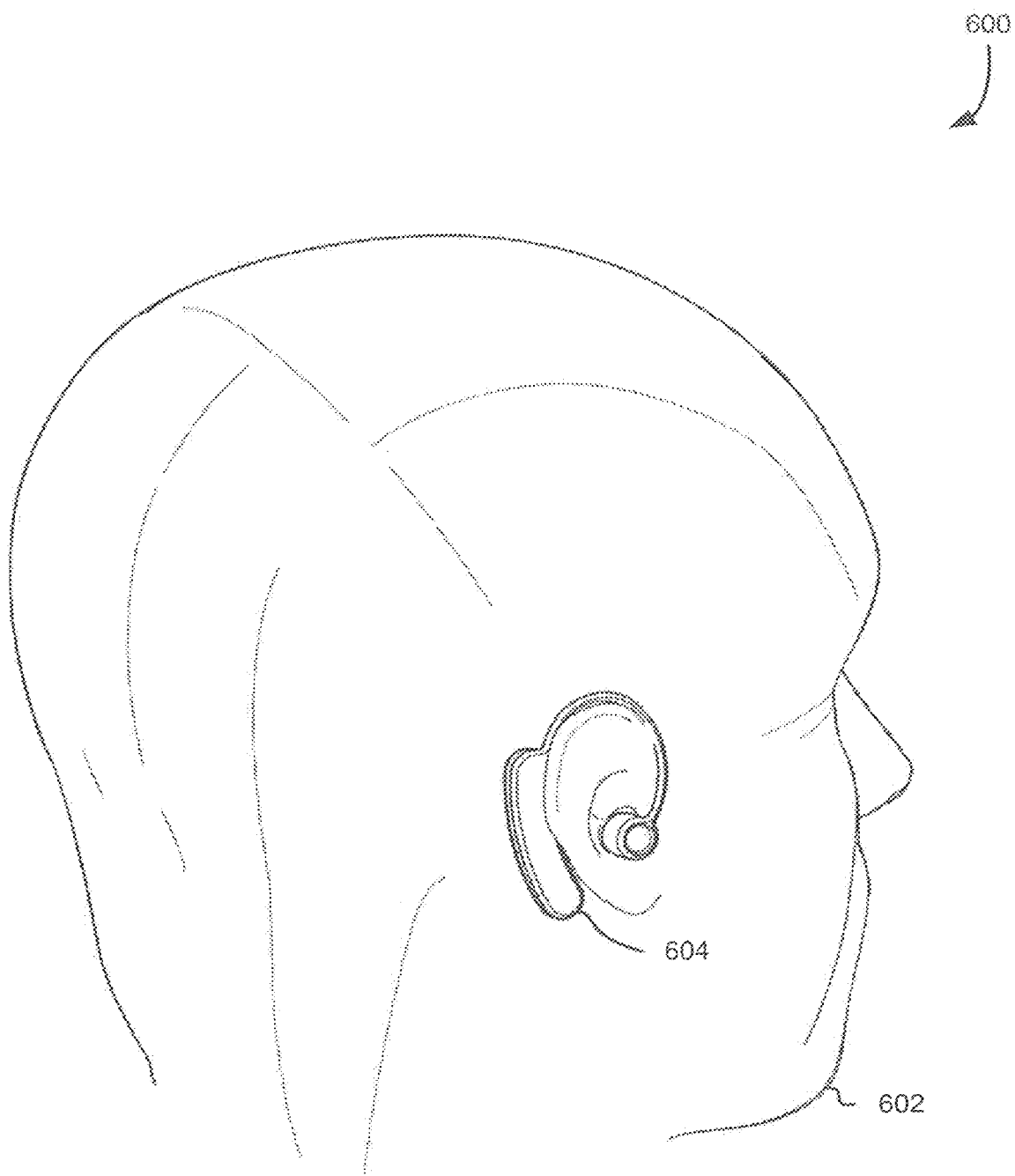
FIG. 6 illustrates an environment where a personal impact monitor is worn in accordance with an embodiment.

FIG. 6 illustrates an example environment 600 showing how a personal impact monitor (i.e., the personal impact monitor described in connection with FIGS. 4 and 5) may be worn when used with a personal impact monitoring system as described herein in connection with FIG. 1 and in accordance with an embodiment. In the example illustrated in FIG. 6, a personal impact monitor 604 such as the PIM 400 is shown as being worn behind the ear of the user 602.

Figure 7:
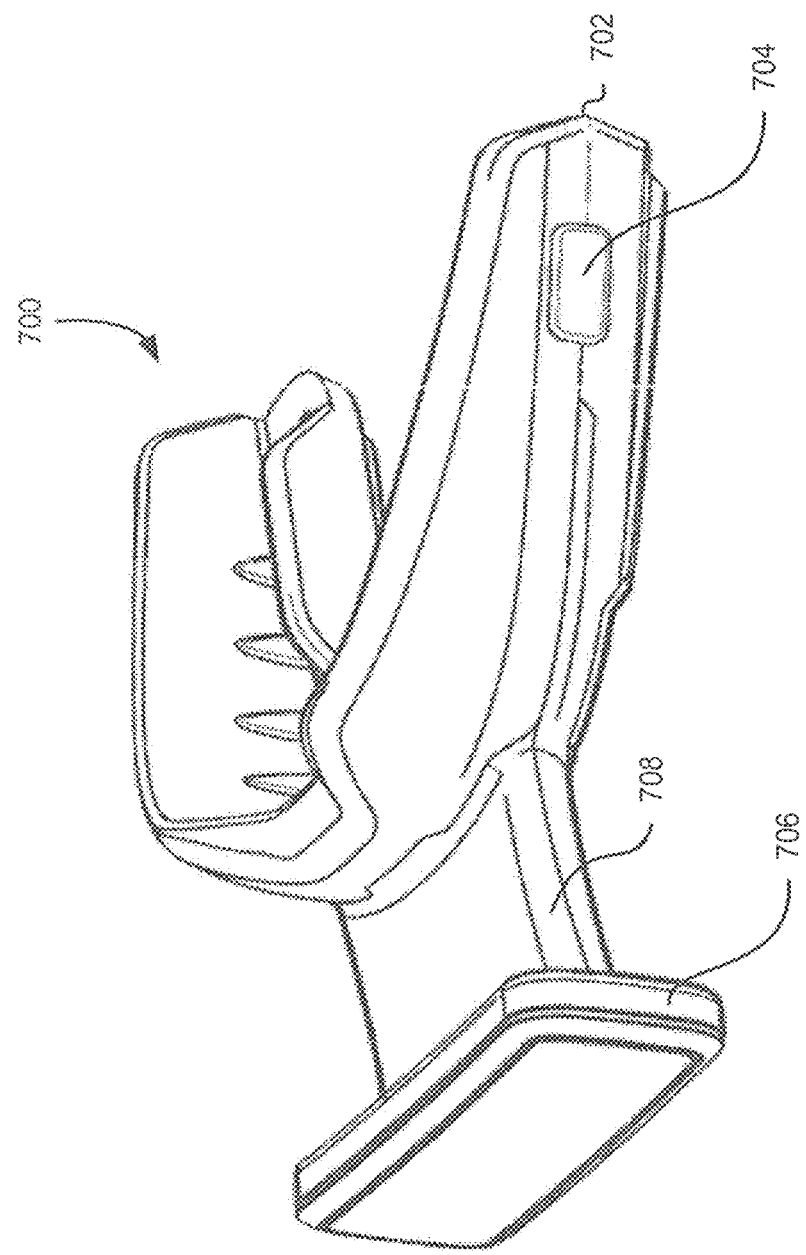
FIG. 7 illustrates a personal impact monitor in accordance with an embodiment.

FIG. 7 illustrates an example personal impact monitor 700 for use with a personal impact monitoring system as described herein in connection with FIG. 1 and in accordance with an embodiment. The example personal impact monitor 700 illustrated in FIG. 7 may be worn within the mouth of a participant and may also incorporate mouth guard 702 protections as described herein. The personal impact monitor 700 may include one or more sensors 704 configured to be in proximity to the mouth tissue (i.e., to measure oral temperature), one or more impact sensors 706, and/or an electronics package 708. Details of a mouth guard embodiment of a PIM are described herein in connection with FIGS. 1 and 2.

Figure 8:
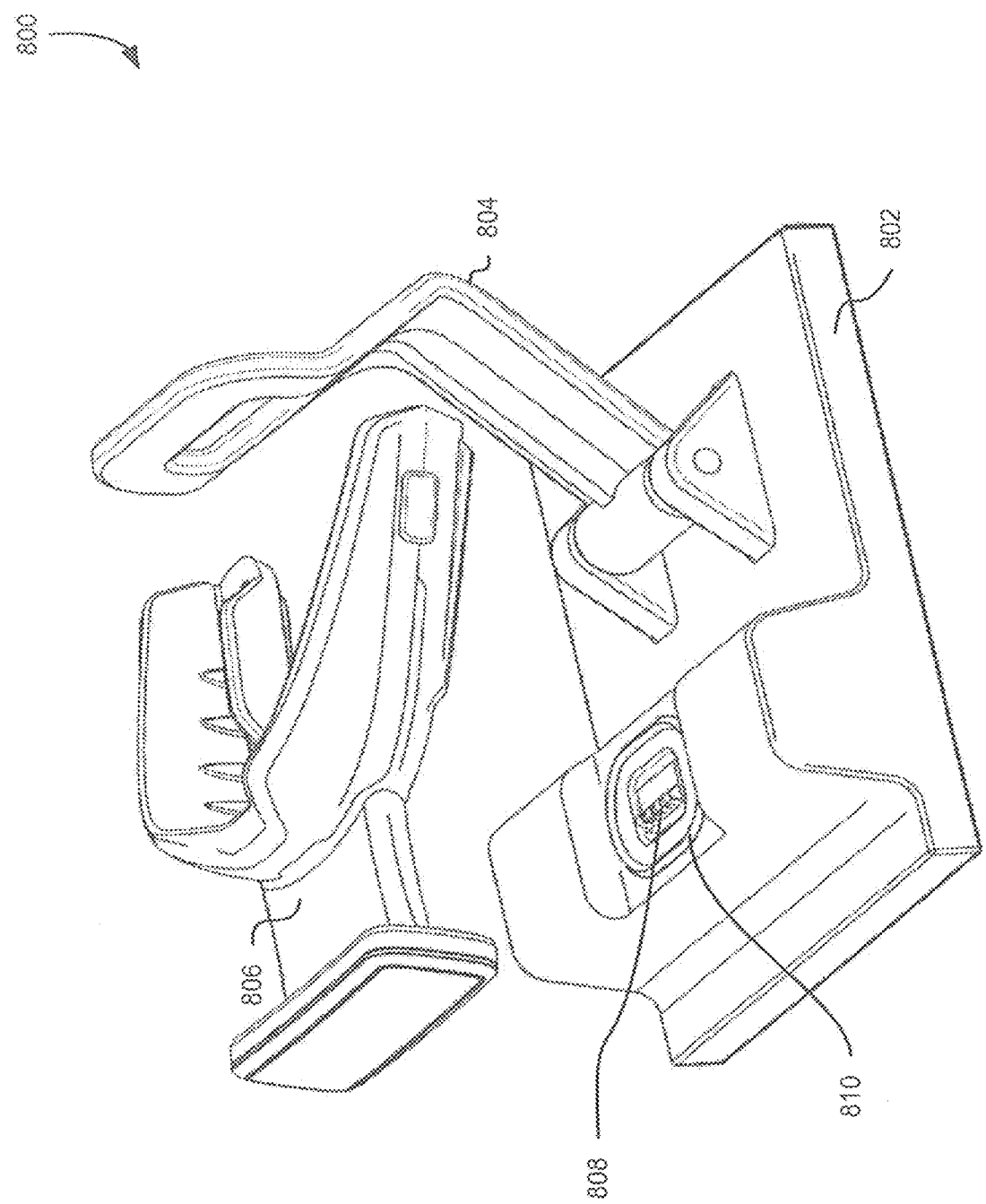
FIG. 8 illustrates an environment where a personal impact monitor is placed within an associated docking station in accordance with an embodiment.

FIG. 8 illustrates an example environment 800 showing a personal impact monitor with an associated docking station for use with a personal impact monitoring system as described herein in connection with FIG. 1 and in accordance with an embodiment. The mouth guard personal impact monitor 806, which may be the same as the personal impact monitor 700 described herein, may be placed in a docking station 802 which may include a retaining lever 804 to secure the personal impact monitor 806 during transport, may include electronics contacts 808 to charge the personal impact monitor 806 and/or to gather data from the personal impact monitor 806, and may also include a gasket 810 to protect the electronics from environmental conditions and/or from moisture.

Figure 9:
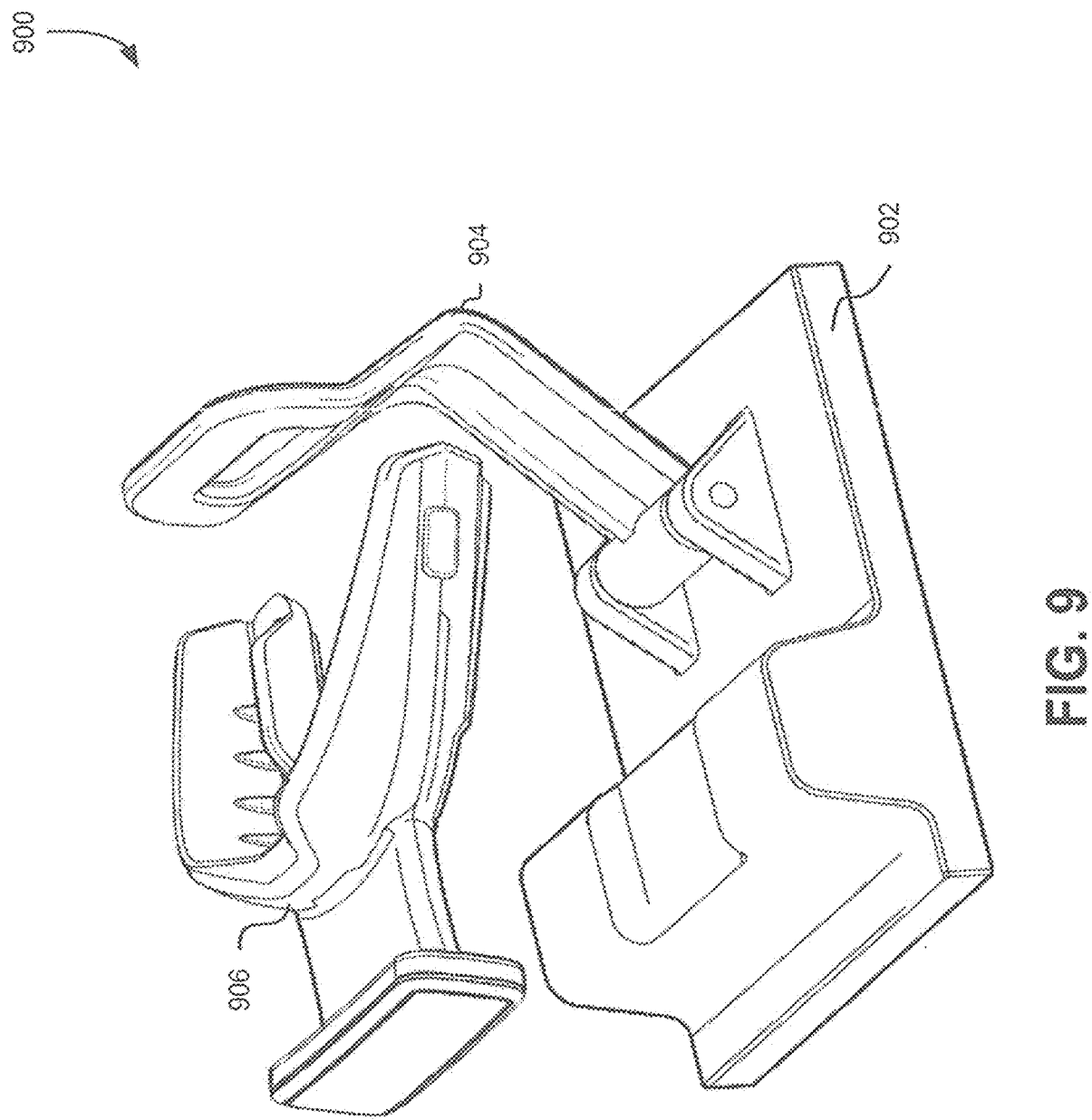
FIGS. 9 to 13 illustrate environments where a personal impact monitor is placed within an associated docking station in accordance with an embodiment.

FIG. 9 illustrates an example environment 900 showing a personal impact monitor and an associated docking station for use with a personal impact monitoring system as described herein in connection with FIG. 1 and in accordance with an embodiment. In the embodiment illustrated in FIG. 9, the mouth guard personal impact monitor 906, which may be the same as the personal impact monitor 700 described herein, may be placed in a docking station 902 which may include a retaining lever 904 to secure the personal impact monitor 906 during transport. The example illustrated in FIG. 9 does not include the electrical contacts. In this embodiment, the personal impact monitor 906 may communicate with a host computer using, for example, wireless communication which may be charged by magnetic induction in the docking station. This type of docking station may also be used when, for example, charging and/or data communication is not needed, or may be used to sanitize a plurality of PIMS.

Figure 10:
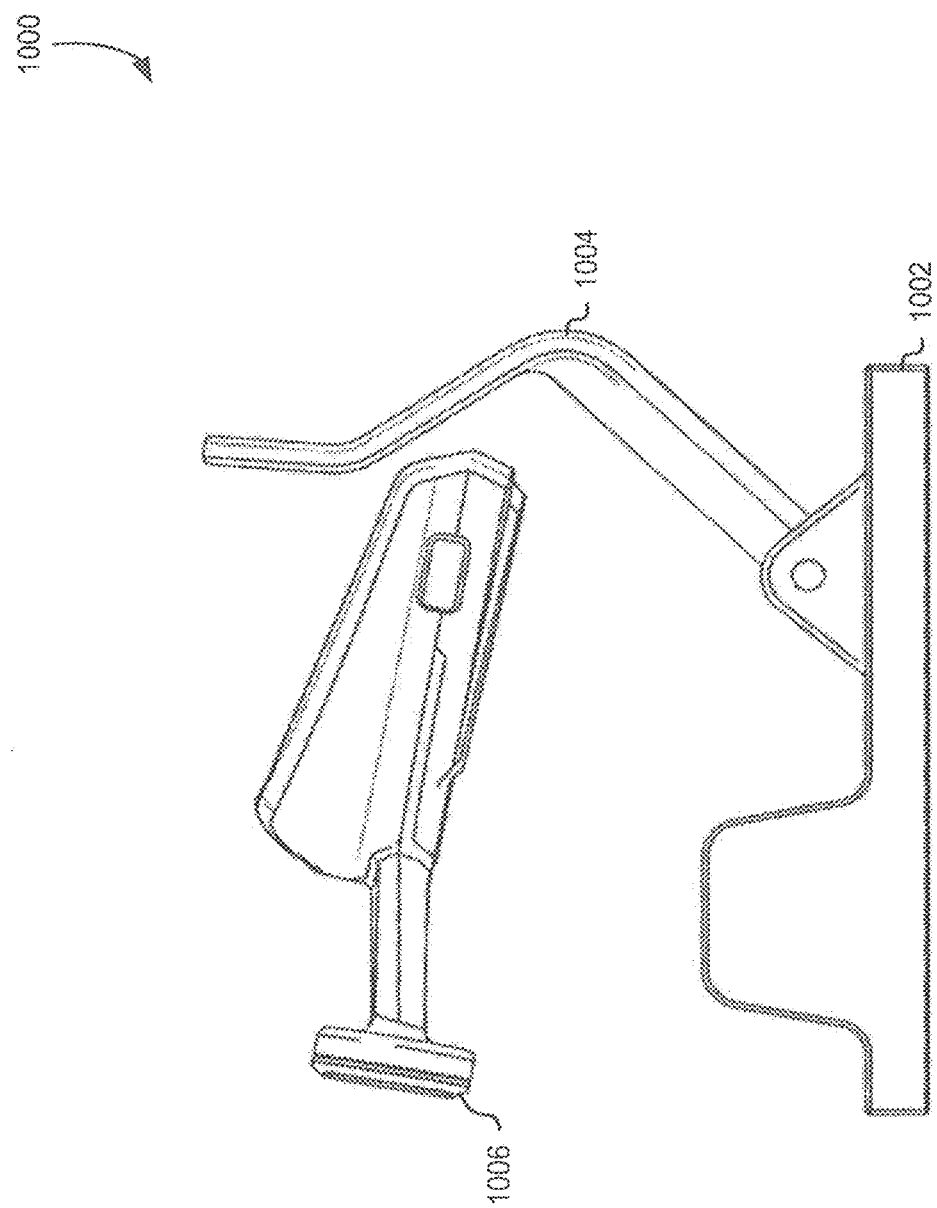

FIG. 10 illustrates an example environment 1000 showing a side view of a personal impact monitor with respect to an associated docking station for use with a personal impact monitoring system as described herein in connection with FIG. 1 and in accordance with an embodiment. FIG. 10 illustrates a PIM 1006 prior to insertion into a docking station 1002 with the retaining lever 1004 in an open or unlocked position. FIG. 10 illustrates the stabilization of the docking station in an open configuration, with the PIM out of contact with the docking station.

Figure 11:
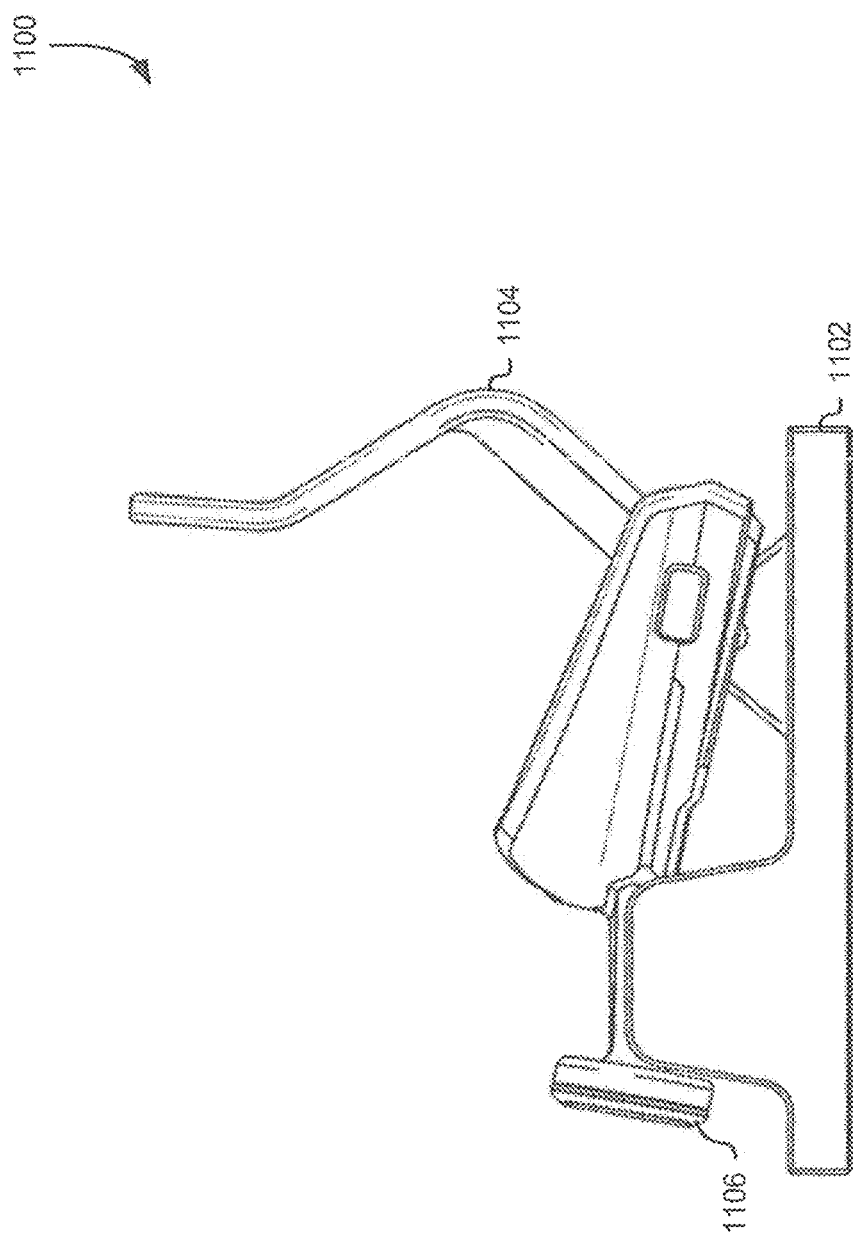

FIG. 11 illustrates an example environment 1100 showing the placement of a personal impact monitor within an associated docking station for use with a personal impact monitoring system as described herein in connection with FIG. 1 and in accordance with an embodiment. FIG. 11 illustrates the PIM 1106 after insertion into the docking station 1102 with the retaining lever 1104 still in an open or unlocked position. FIG. 11 illustrates the PIM positioned in contact (mechanical and/or electrical) with the docking station.

Figure 12:
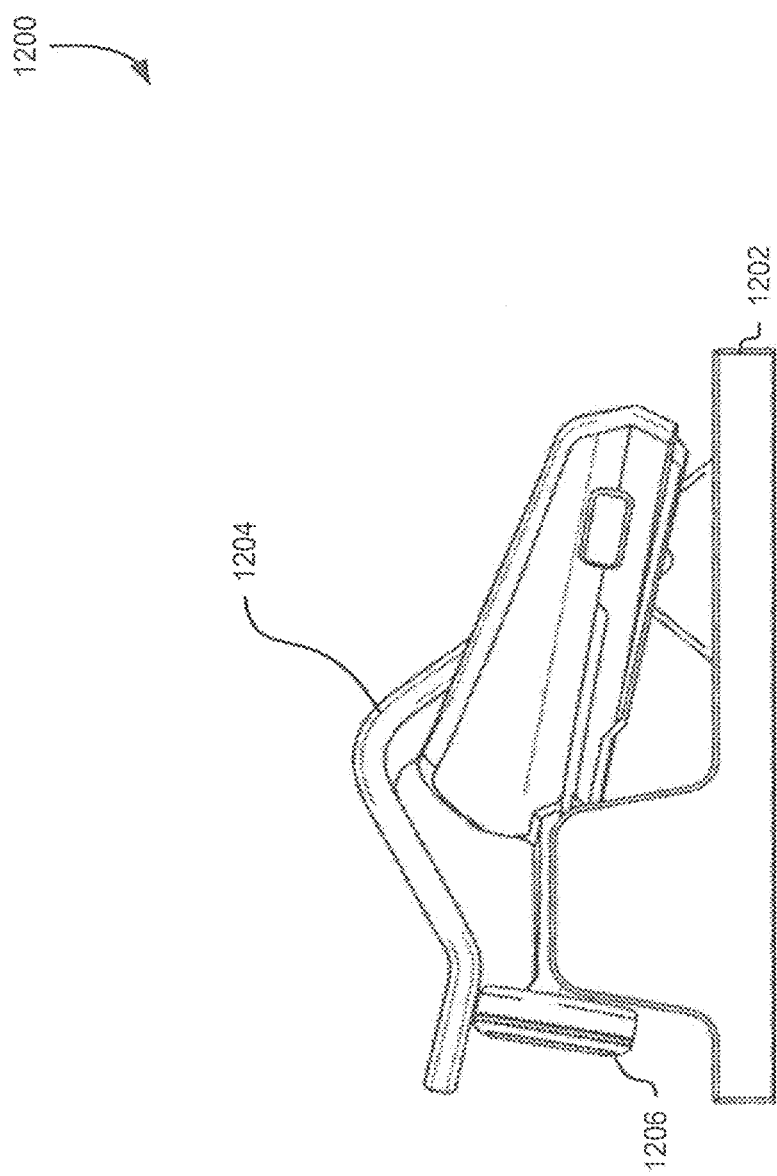

FIG. 12 illustrates an example environment 1200 showing the securing of the placement of a personal impact monitor within an associated docking station for use with a personal impact monitoring system as described herein in connection with FIG. 1 and in accordance with an embodiment. FIG. 12 illustrates the PIM 1206 after insertion into the docking station 1202 with the retaining lever 1204 in a closed or locked position. FIG. 12 illustrates the stabilizing element in a closed configuration, securing the PIM to the docking station.

Figure 13:
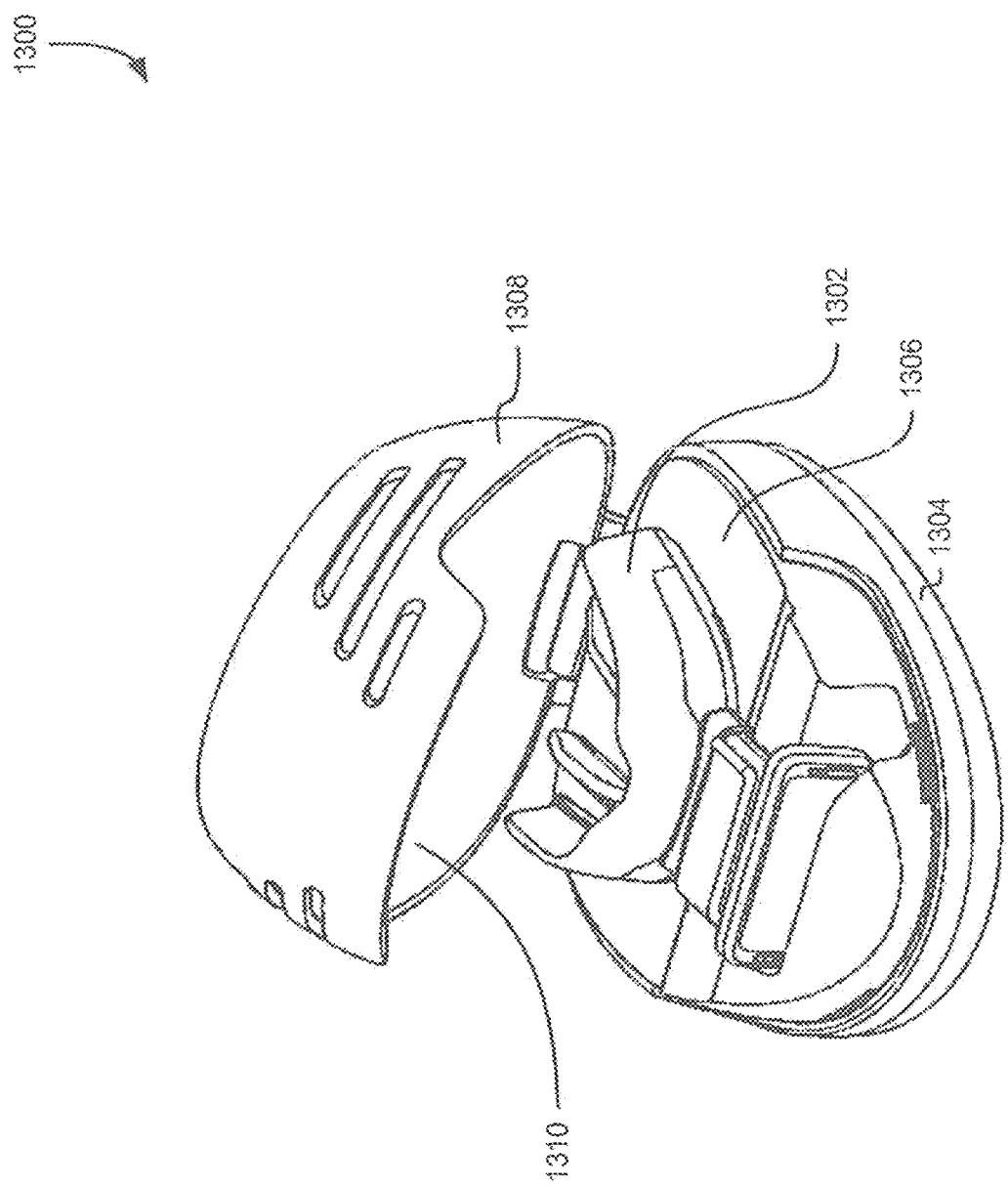

FIG. 13 illustrates an example environment 1300 showing the placement of a personal impact monitor within an associated personal docking station for use with a personal impact monitoring system as described herein in connection with FIG. 1 and in accordance with an embodiment. FIG. 13 illustrates additional features of a docking station that may be implemented in accordance with various embodiments. FIG. 13 illustrates a personal mouth guard charger and docking station for a mouth guard personal impact monitor 1302. The personal mouth guard charger and docking station comprises a molded case 1304 with embedded electronics 1306 configured to connect to a power source. The power source may be a battery, alternating current, a universal serial bus (USB) power source, a solar power source, other power source, or combination of power sources. The electronics may be configured to charge a battery or set of batteries of the mouth guard.

The electronics may also be configured to power an ultra violet ("UV") light 1310 for sanitizing the mouth guard. The personal mouth guard charger may have a clamshell configuration 1308 and may include the UV light source in the top portion of the clamshell. The interior of the personal mouth guard charger may be reflective such that the UV light from the clamshell is sufficient to sanitize the entire portion of the mouth guard that fits within the player's mouth. Additional UV light sources may also be included in the top portion of the clamshell, the bottom portion, and/or otherwise within the charger and/or docking station so as to sanitize the mouth guard while it is stored. It should be noted that other mechanisms may be utilized for sanitation of the mouth guard inside of the charger in addition to, or as an alternative to, UV light. Such alternatives include, but are not limited to thermal sanitation (with the mouth guard adapted to be made from materials to withstand the heat required for sanitization), chemical sanitation, or some other such method of sanitation.

Figure 14:
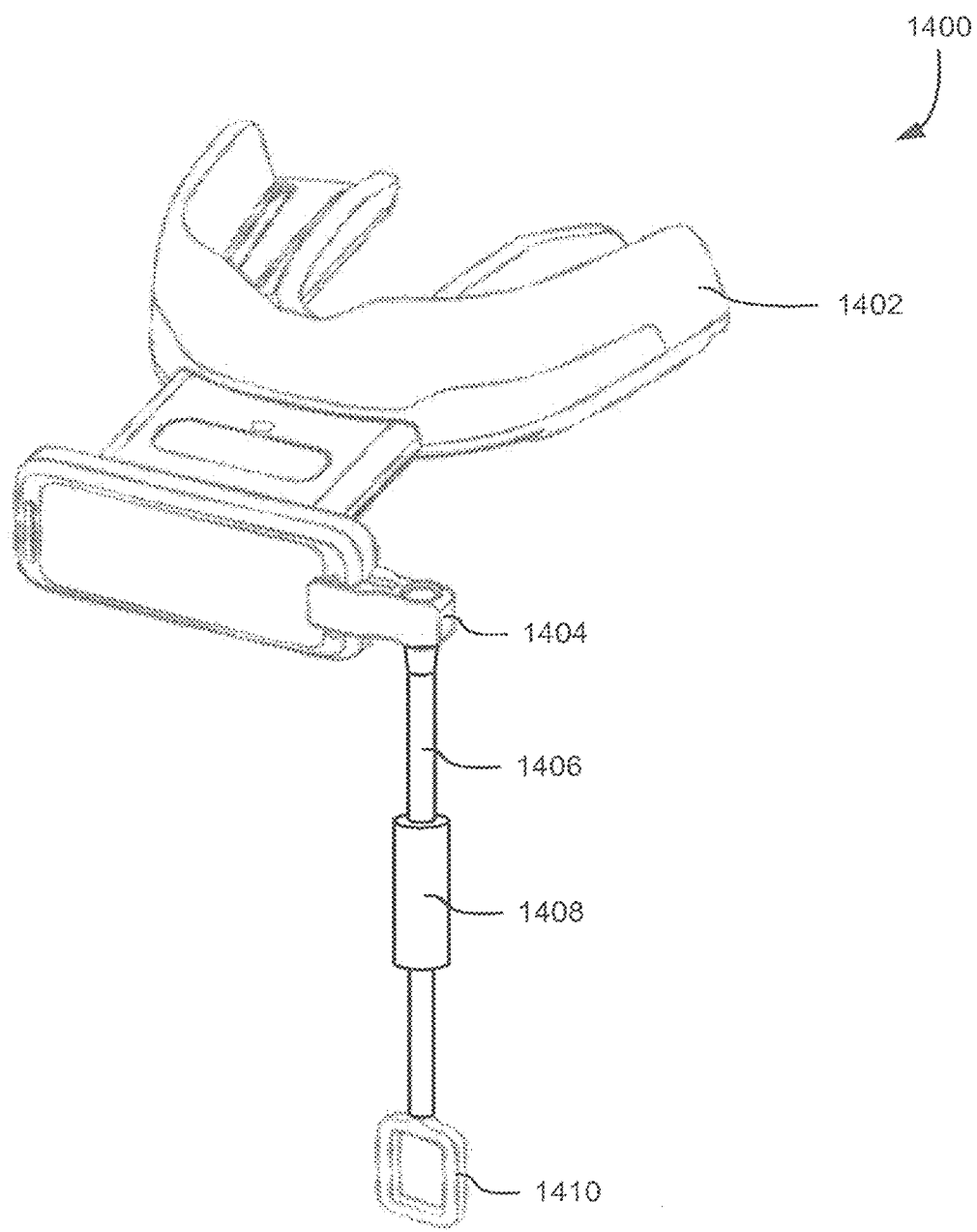
FIG. 14 illustrates a personal impact monitor with a tether in accordance with an embodiment.

FIG. 14 illustrates an example environment 1400 showing a personal impact monitor with a tether for use with a personal impact monitoring system as described herein in connection with FIG. 1 and in accordance with an embodiment. A mouth guard tether 1406 may be connected to a mouth guard personal impact monitor 1402 to secure the mouth guard to another structure, such as a helmet (e.g., by connecting to a facemask of the helmet). As illustrated in FIG. 14, the mouth guard tether connection 1404 may be mechanical and may be detachable. Detachment of the tether from the mouth guard may allow the mouth guard to be removed from the tether and placed inside of the charger. In some embodiments, a charger and/or docking station may be configured to allow for inclusion of the tether inside of the charger and/or the docking station or may be configured to allow the tether to pass from the interior of the charger to the exterior while the charger is closed (e.g., by way of a channel formed by the top and/or bottom portion). Use of a tether may allow a participant to maintain possession of the mouth guard when the mouth guard falls out of the player's mouth and/or to allow the player to communicate verbally without requiring the player to hold the mouth guard in his/her hand.

The connector of the tether 1406 may connect to a portion of the PIM that protrudes from the player's mouth. In the illustrated example, this portion of the PIM may be configured with slots on opposing sides of a flange where the slots adapted to receive pinchers of the connector. In this manner, the tether may be easily detached from the PIM by pulling the connector from the PIM. Other mechanical or other connections (including permanent, non-detachable connections) may be considered as being within the scope of the present disclosure. Generally, connection between the tether and PIM may be mechanical, electrical, both mechanical and electrical, or otherwise. Further, the connection between tether and PIM may provide robust connection for normal use and breakaway features for situations where excessive forces are applied to mouth guard, tether, or facemask.

In an embodiment, a flexible tether cord may extend from the connector of the tether to a loop 1410 that terminates an opposing end of the tether cord. The loop my enable the tether to attach to a facemask or other structure by encircling a bar of the facemask (or other structure) with the tether cord by running the connector through the loop. In this manner, when the PIM is detached from the tether, the tether remains connected to the facemask (or other structure), allowing the PIM to be reattached when appropriate. Other mechanisms for attaching the tether to the facemask or other structure include, but are not limited to, snaps, a hook and loop connector, adhesive, magnetic, and other mechanical mechanisms may also be considered as being within the scope of the present disclosure. Further, the tether connection to the facemask (or other structure) may also include a robust connection for normal use and breakaway features for situations where excessive forces are applies to the PIM, tether, or facemask.

In some embodiments, the tether may include electronics 1408 including, but not limited to, a battery, memory, microprocessor, radio, or other electronics components (e.g., one or more sensors). The electronics 1408 in the tether may be configured to perform functions involving data from sensors in the PIM, such as described above as being performed by the PIM. Functionality described herein associated with the PIM may also be performed by the electronics in the tether.

In an embodiment, a mouth guard may be configured with break-away electronics and/or break-away mechanical features to protect the teeth and/or jaw in the event of an impact directly to the mouth guard. The mouth guard may include both electronics and a breakaway tether feature as described herein such that the tether may disconnect from either a helmet and/or from the mouth guard during application of high force (e.g., during an extreme impact where the helmet may be dislodged from an athlete's head). The mouth guard may also include a user removable electronics assembly such that the electronics system may be removed and inserted into a different mouth guard.

Figure 15:
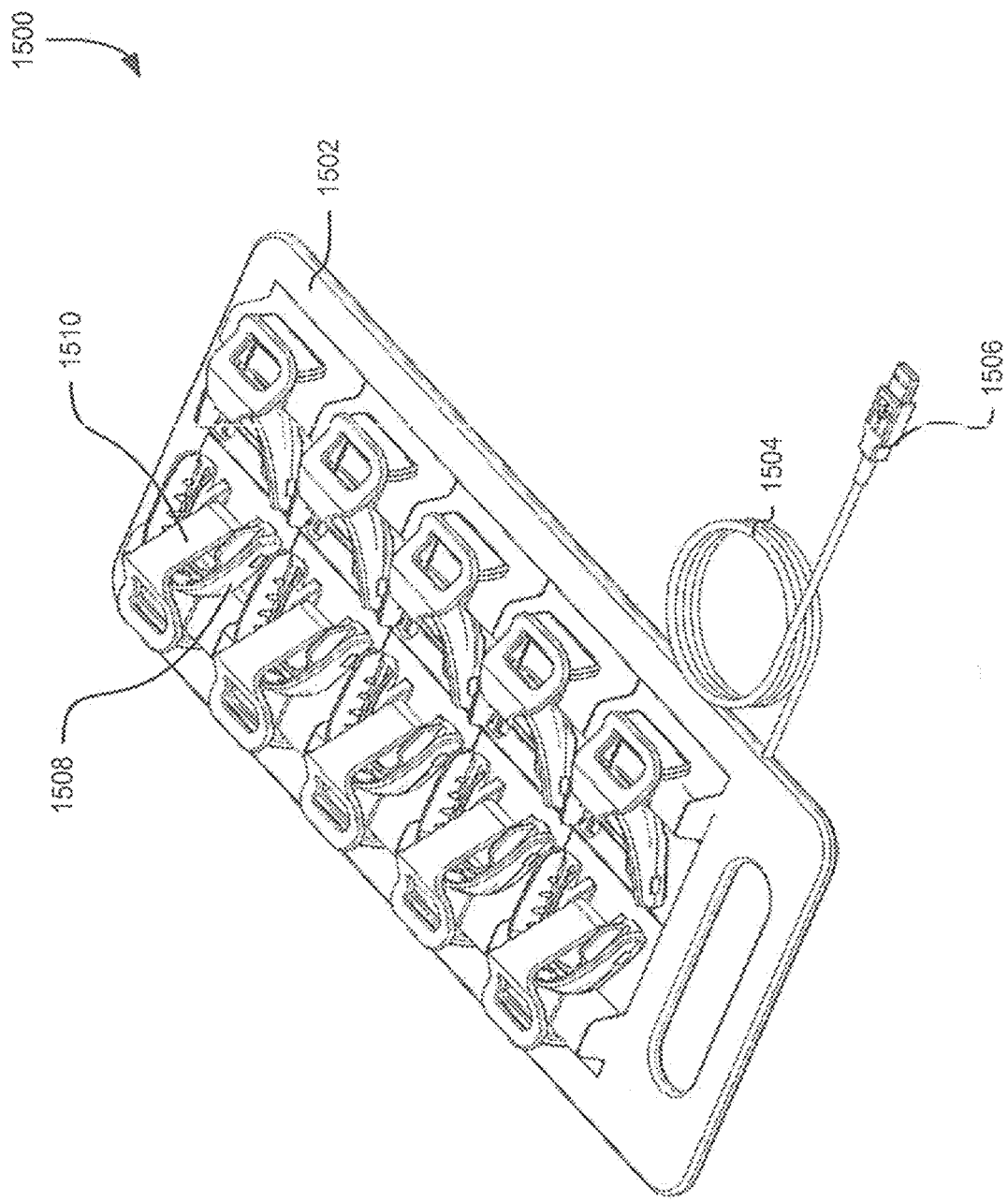
FIG. 15 illustrates an environment where a plurality of personal impact monitors may be secured within an associated docking station in accordance with an embodiment.

FIG. 15 illustrates an example environment 1500 where a plurality of personal impact monitors may be secured within an associated docking station for use with a personal impact monitoring system as described herein in connection with FIG. 1 and in accordance with an embodiment. In the docking station illustrated in FIG. 15, a plurality of PIMs may be docked. The docking station 1502 illustrated in FIG. 15 may also be referred to as a bank charger. FIG. 15 illustrates a docking station (or bank charger) for a plurality of mouth guard PIMs 1508. The mouth guard PIMs may each have a sensing element secured to the general "U" shape of the mouth guard that may include the sensors and dedicated circuitry, storage, etc., as described herein. The PIMs 1508 may be secured within the docking station using a stabilizing element 1510 (also referred to herein as a retaining element) as described herein. The docking station may also include an integral wired connection 1504 with a connector 1506 (e.g., USB connector) that allows the docking station to be in communication with one or more remote devices such as a computer.

The docking station may be configured to dock different types of PIMs. For example, if the PIM is a component adapted to be detachably secured to a helmet, the component may be removed from the helmet and docked to a dedicated docking station. Alternatively, the PIM could be part of a helmet, and the entire helmet may need to be attached to the docking station. The docking station may be adapted to charge batteries in the PIMs when the PIMs are docked on the docking station. The wired connection may also allow each PIM to communicate data unique to each PIM to a remote device. In some embodiments, the bank charger may be connected to a host computer using the connector 1506.

The docking station may also allow multiple PIMs to be addressed for post-activity data download. In some embodiments, a personal impact monitoring system may not employ wireless/real time data reporting functionality that allows real-time data transfer from the PIM. In such embodiments, a post-activity docking station may be configured to receive data from the PIMs after the activity.

When attached to a docking station, each PIM (e.g., mouth guard) may be individually addressed for communication with a host computer. The docking station may control the positional location of the PIM (e.g., the physical slot location information on the docking station). When docked, the bank-charging device may be configured to query the PIM and/or provide a method for the host computer to query the PIM. An integral USB microcontroller may be employed to provide physical slot identification, control signals, provide device communication, and/or provide other functionality.

The docking station may also have one or more memory devices adapted to store PIM data locally. For example, data may be received from PIM and stored in onboard memory, on an integral printed circuit board, or on some other memory device within the docking station. The stored data on the docking station may then be communicated to a host computer at a later time. The data may remain on the docking station, and thus the docking station may be configured to perform as an intermediate data repository for safety reasons or for activities occurring at a travel/away location. The intermediate data repository may provide backup data storage when a host computer is not present at the activity location.

In some embodiments, the docking station may be scaled against moisture intrusion. In such an embodiment, the PIMs (e.g., mouth guards), while docked, may be cleaned while they are being charged and/or while data is being downloaded. For example, the PIMs may be sprayed with a disinfectant and/or cleaning solution such that the electronics in the docking station are protected during contact with the fluid and/or spray. The underside of the PIM may employ a non-ferrous (i.e., anti-corrosive) contact material (e.g., made from stainless steel or titanium, or platinum) such that performance may be retained in the wet environment. In an embodiment, the docking station may employ a gasket and or sealing member such that fluid ingress is limited to outside the area protected by the gasket, keeping internal electronics protected. The docking station may employ drainage elements that allow moisture to easily pass away from both the PIMs and the docking station itself.

As illustrated in FIG. 15, the docking station may include a stabilizing element 1510 to retain the PIM in the electrically coupled position (i.e., docked). The stabilizing element 1510 may be configured to mechanically retain the PIM while docked. This provides for added stabilization during movement, including transport, etc. In an embodiment, the docking station may employ a spring type or otherwise mechanically retained lever to keep the PIMs in position, and to allow for physical retention as well as to maintain contact between the electrical contacts of both bank charger and PIM. In an embodiment, the docking station 1502 may have the same number of slots as the number of people playing at a certain position. For example, when used in association with American football, the charger may have a number of slots corresponding to the number of quarterbacks, or a number of slots corresponding to the number of wide receivers.

Figure 16:
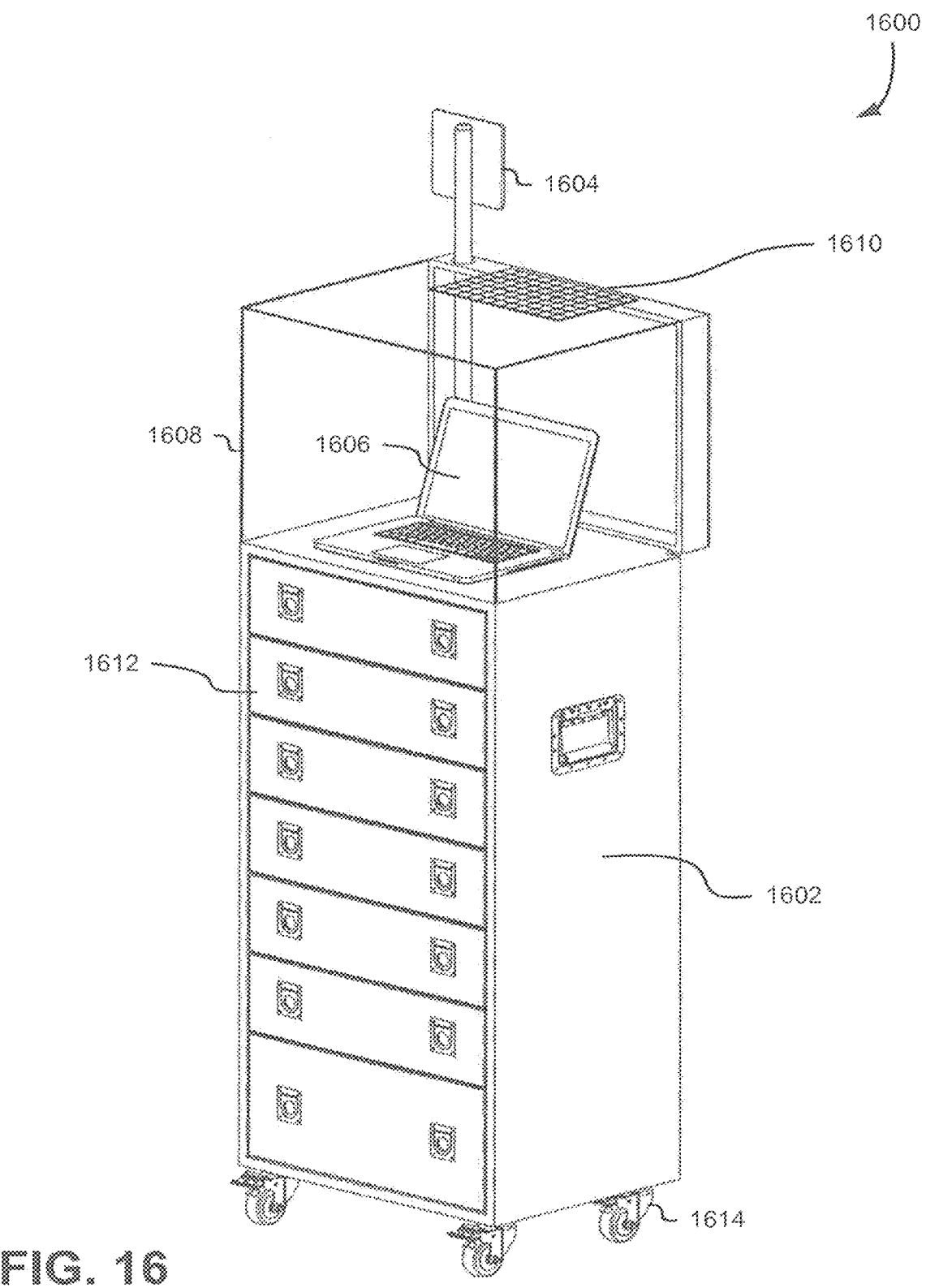
FIGS. 16 and 17 illustrates environments where a monitoring station may be operated in accordance with an embodiment.

FIG. 16 illustrates an example environment 1600 where a monitoring station for use with a personal impact monitoring system may be used as described herein in connection with FIG. 1 and in accordance with an embodiment. The monitoring station 1602 may include an antenna 1604, a host computer 1606, a shield 1608, a solar panel 1610, and/or one or more storage locations 1612 as described herein. The monitoring station 1602 may be made portable by, for example, being incorporated into a wheeled case as illustrated in FIG. 16.

In some embodiments, the system includes an enclosure for one or more docking stations that may provide for PIM sanitation. In some embodiments, the enclosure includes ultraviolet lights for sanitization. The enclosure may be constructed so as to minimize cross-contamination from sanitizing solutions applied to other PIMs stored within the enclosure. For example, in an embodiment, an inverted stair-case design with the PIMs attached so as to hang in horizontally staggered rows may be used. The enclosure of the monitoring station may have ventilation (e.g., one or more fans or vents) to allow for long-term storage. In some embodiments, the enclosure rows (to which a plurality of PIMs may be secured) are adapted to be expanded and contracted (e.g., by rolling).

The monitoring station may be configured as a sideline cart. The monitoring station may be deployed on the sidelines during an athletic activity and may be viewed and accessed by, for example, physicians, coaches, and players. The monitoring station may be a portable unit with wheels, including one or more shelves or drawers. In the example illustrated in FIG. 16, a computer may be placed on a shelf, but any kind of remote device may be placed thereon (e.g., a tablet computer). The monitoring station may include an optical communications receiver/transmitter and/or may include a radio frequency communications antenna. The monitoring station may also include a privacy screen to restrict the view of the contents of the table surface (e.g., from television camera or fans in attendance) and/or to shield the computer screen from sunlight and weather elements.

Figure 17:
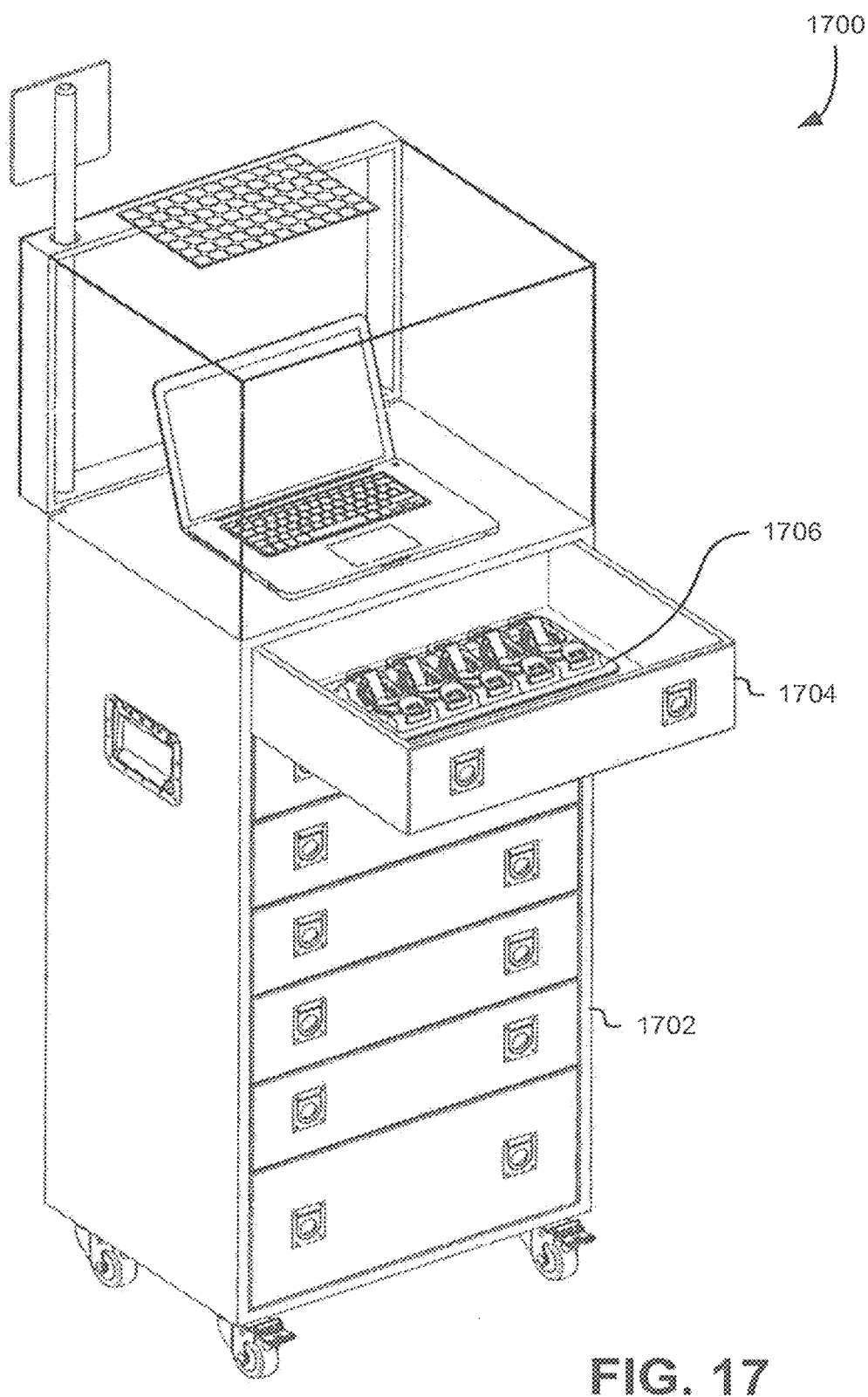

FIG. 17 illustrates an example environment 1700 where a monitoring station for use with a personal impact monitoring system may be operated as described herein in connection with FIG. 1 and in accordance with an embodiment. The monitoring station 1702 illustrated in FIG. 17 may include a bank charger enclosure 1706 as described herein, which may be stored within a drawer 1704 of the monitoring station. For example, one or more of the drawers described herein may house therein an enclosure adapted to retain a plurality of PIMs in horizontally staggered rows.

In some embodiments, the monitoring station may be configured to occupy a volume less than a certain number of cubic meters and/or according to one or more ergonomic considerations. For example, a monitoring station may be sized such that the upper horizontal surface is of a height above the ground that offers easy viewing (e.g., 48" off the ground). In some embodiments, the monitoring station may have a width ranging from 12" to 48" or more (should additional storage volume be required for a large team). In some embodiments, the depth of the monitoring station can range from 12" to 48". Monitoring stations may generally be sized such that they can occupy a space on the sideline area of a football or athletic field while still offering room for foot traffic (e.g., typically placed 10 feet or more beyond the out-of-bounds line of the football field).

The monitoring station may also include an antenna mounting such that the antenna may be placed in a position ideal for RF communication. As illustrated in FIG. 17, the antenna is facing away from the computer screen such that a user can view the field and have the antenna facing toward the field. The monitoring station may offer features that help align the antenna such that it is oriented in a position ideal for RF communication with on-field PIMs. The antenna may be, for example, a bullet shape, or a planar shape, a multi-planar shape, or housed within a cylindrical shape.

FIG. 18 illustrates an example environment 1800 where a sideline receiver may be placed relative to a playing field for use with a personal impact monitoring system as described herein in connection with FIG. 1 and in accordance with an embodiment. A directional dual-polarized antenna 1810 (also referred to as a sideline receiver) is shown placed 1804 in proximity to a field 1806 with a plurality of participants 1808 and also shown placed 1804 in proximity to a monitoring station 1802. In an embodiment, the directional dual-polarized antenna is placed in proximity to the field such that it is configured for the reception of signals from PIMs, regardless of their physical orientation. The directional dual-polarized antenna may be configured to favor receipt of signals from devices on the playing field, rather than from devices off the playing field, such as PIMs of players on the sideline.

In an embodiment, a system may have a multiplicity of PIMs each having a single (that is, markedly or detectibly dominant) polarization and/or dual polarization in each of three orientations. A sideline receiver antenna with directional dual-polarized characteristics may improve reception range and may also minimize network congestion (due to a reduced number of failed packets). Dual polarization may allow reception of signals from PIMs regardless of their physical orientation. Directionality in the form of an approximately 180 degree beam width may provide signal gain for PIMs on the field of play, and may provide signal attenuation for potential noise sources behind the sideline and field of play.

FIG. 18 illustrates a directional dual-polarized antenna configured with directionality of approximately 180 degrees to cover an entire playing field. Other directionalities may be used, which may depend on the sensitivity and location of the antenna. Further, multiple antennas with directionalities that individually do not receive signals from the entire field of play but that collectively receive signals from the entire field of play may be used. For example, two antennas on opposite corners on the wide side of the field may be used to cover the entire field. As another example, four antennas, one in each corner of a rectangular field may be used. Further, the number of antennas may vary as appropriate, such as for use of PIMs in activities that involve areas that are not necessarily rectangular.

Other variations considered as being within the scope of the present disclosure may include a sideline notification system. In an embodiment, a sideline notification system is a computer system configured to allow configuration/selection of which PIMs should generate notifications and/or present impact data to an observer. For example, the system may allow for a user to select collections of players and/or PIMs for notification, reporting, or presentation of real-time impact data to an observer. Collections may be defined based at least in part on user-defined attributes (such as a team, position, or otherwise) and/or based at least in part on machine-inferred collections (e.g., based on algorithmic analysis of current or historical data). In an embodiment, the system is configured to disconnect (or request disconnection) of PIMs from the wireless communication network based on the sideline users' selected collections.

Moreover, the sideline notification system may allow for prioritized real-time delivery of information from PIMs. For example, data transmission from PIMs may be optionally configured to prioritize data transmission based on factors such as impact severity, number of recent impacts, time since impact was originally recorded and/or other factors, some of which may be user-defined using available data. In some examples, data transmission from PIMs may be configured to operate in a "bulk transfer" mode for post-event transfer of data not transmitted previously in a real-time session as described herein. In addition, PIMS may be configured to provide indications to the sideline notification system of an amount of data not yet transmitted or may be configured to provide other information, such as indications of traumatic events that enable the sideline notification system to prioritize receipt and/or display of information regarding the events.

In an embodiment, sideline notification is configured to generate reports based at least in part on PIM statistics such as time in mouth, time on charger, time battery is dead, and/or time since last usage. Such reports may provide actionable data to improve player compliance with PIM use. Low battery alerts provided by the sideline notification system may enable action to prevent a player from using a PIM that may become non-functional during play as a result of a battery drain.

Figure 19:
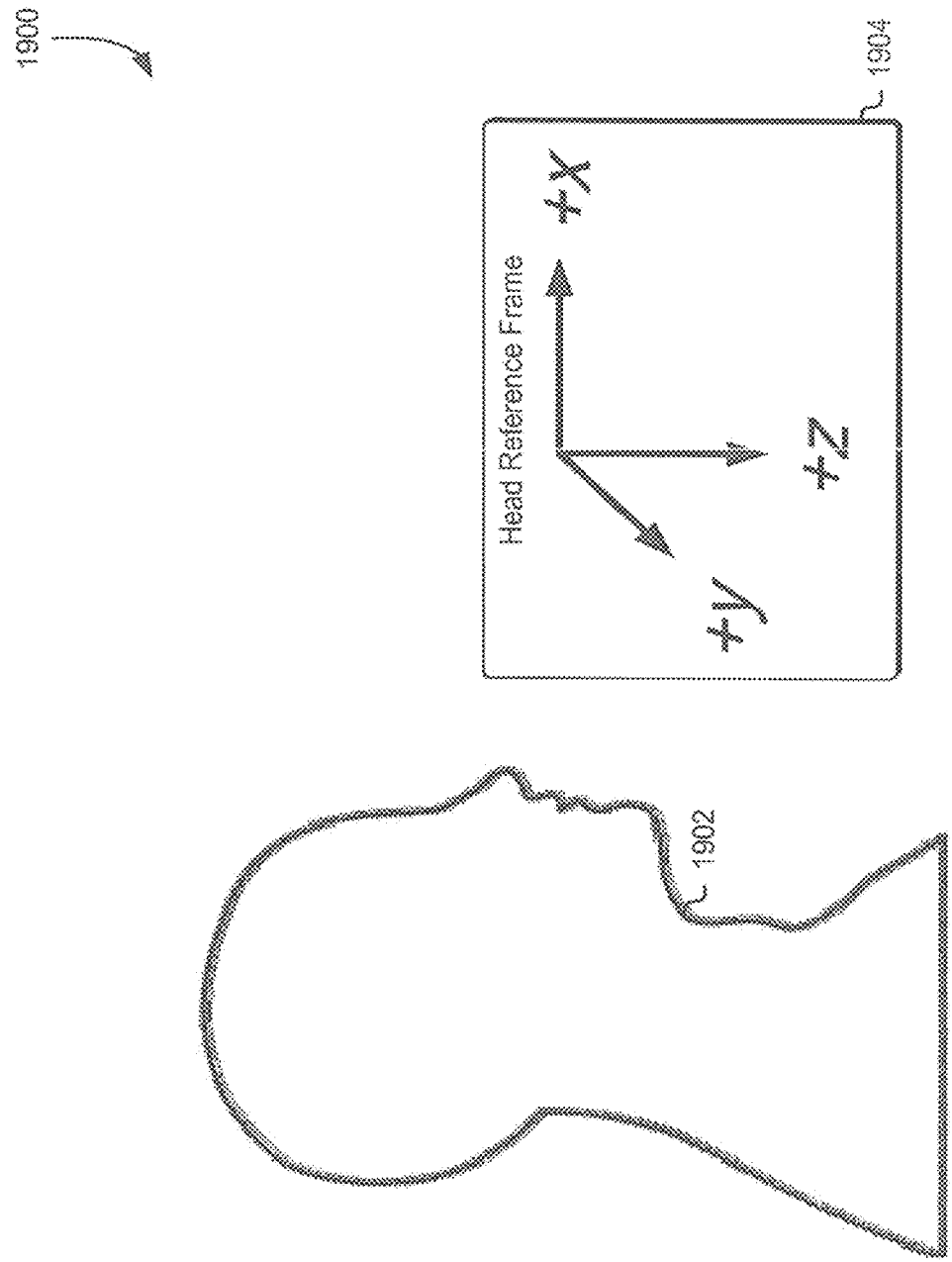
FIG. 19 illustrates an environment indicating a head reference frame in accordance with an embodiment.

FIG. 19 illustrates an example environment 1900 indicating a head reference associated with a human skull for use with a personal impact monitoring system as described herein in connection with FIG. 1 and in accordance with an embodiment. Within the present disclosure, a 3-axis value refers to the Cartesian components of a vector value as expressed in a particular coordinate reference frame ("CRF"). A 3-axis gyroscope is a sensor that measures the rotational velocity vector, decomposed into Cartesian coordinates of a known CRF. A 3-axis accelerometer is a sensor that measures the linear acceleration vector, decomposed into Cartesian coordinates of a known CRF that is not necessarily the same as the gyroscope CRF. For purposes of illustration, we define a head reference frame (IIRF) that conforms to the SAE standard J211-1 for test dummy coordinate systems, positive x-axis ("+x") pointed forward from the test dummy's point of view, positive y-axis ("+y") from left to right, and the positive z-axis ("+z") from superior to inferior (i.e., pointing downward). This corresponds to a "right hand" coordinate system.

Figure 20:
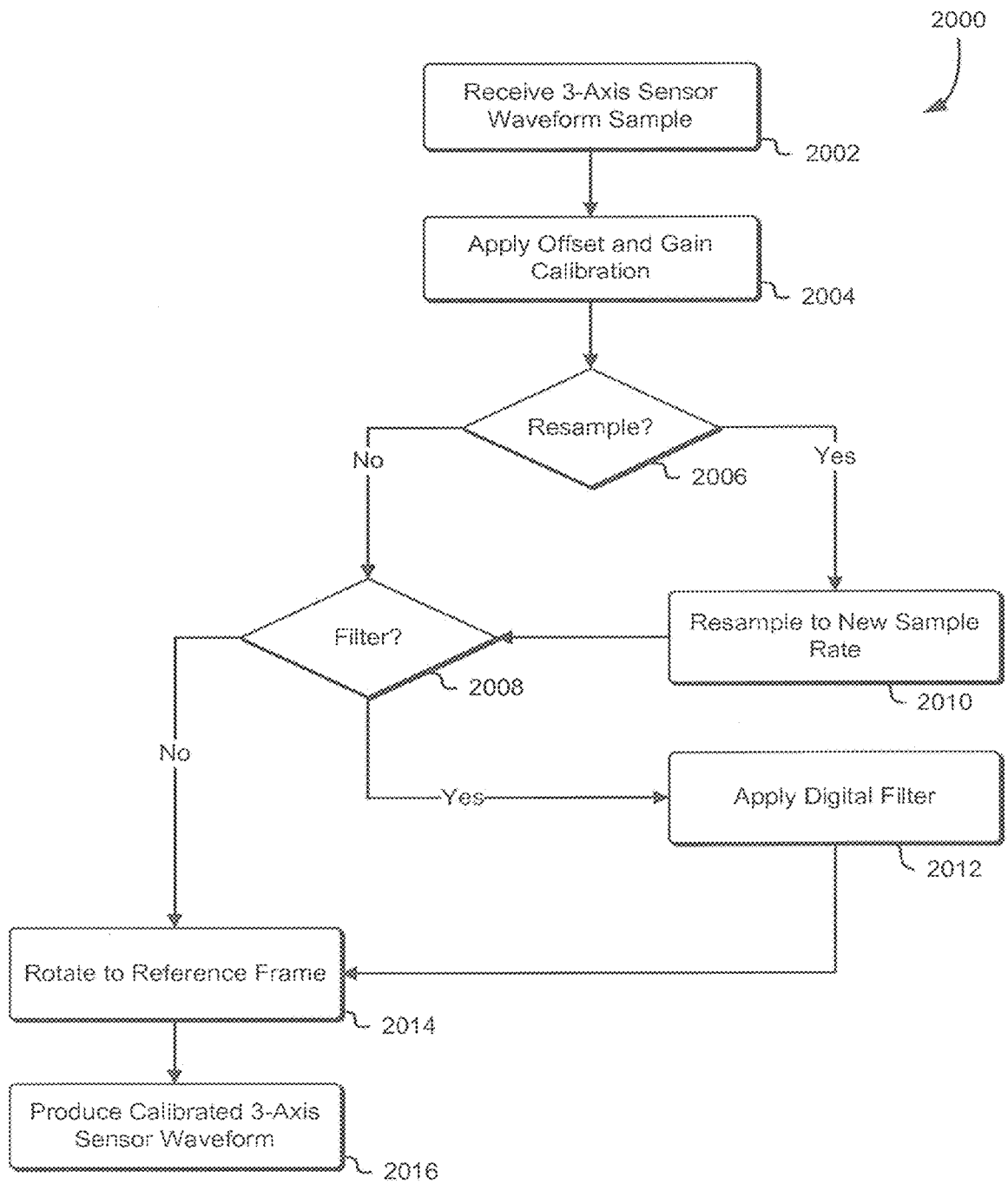
FIG. 20 illustrates a first part of a process for kinematically analyzing impact data in accordance with an embodiment.

FIG. 20 illustrates a portion 2000 of an example process for kinematically analyzing impact data using components of a personal impact monitoring system as described herein in connection with FIG. 1 and in accordance with an embodiment. The impact analysis software described herein may perform such kinematic analysis using a combination of kinematic and mathematical techniques to analyze 3-axis linear acceleration data and 3-axis rotational velocity data captured in a PIM that is rigidly fixed in physical relationship to the skull of the person experiencing the impact. The analysis calculates the 3-axis linear acceleration and rotational acceleration at any point of interest, but especially at likely points of injury due to collision between skull and cerebral cortex. Methods to decompose the linear acceleration vector at likely points of injury into normal and tangential components with respect to the interior surface of the skull are described that represent the mechanisms of traumatic brain injury. Finally, methods that individualize the analysis to the unique brain and skull geometry of an individual person are described.

Figure 21:
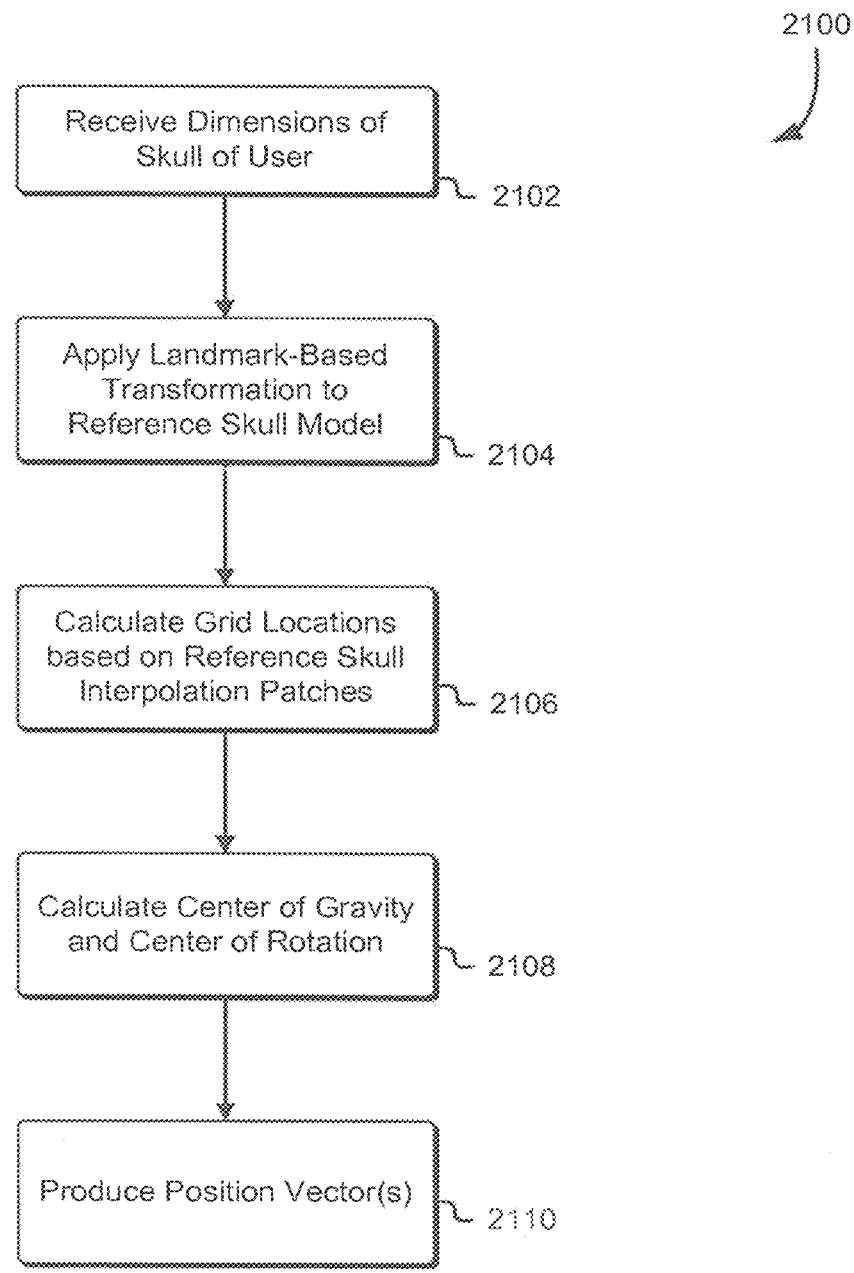
FIG. 21 illustrates a second part of a process for kinematically analyzing impact data in accordance with an embodiment.
Figure 22:
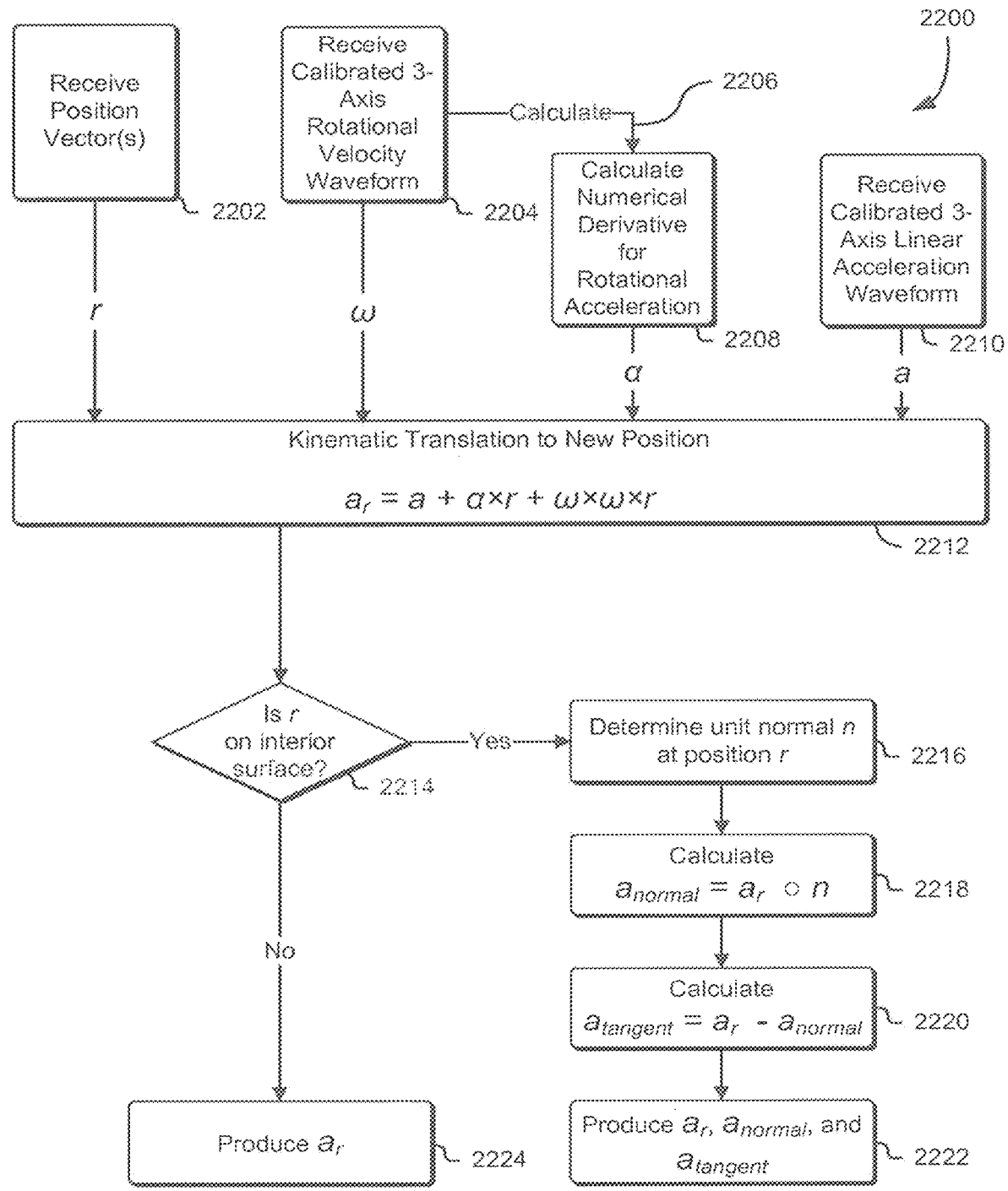
FIG. 22 illustrates a third part of a process for kinematically analyzing impact data in accordance with an embodiment.

The analysis process begins by modeling the head as a mechanically rigid body, which may be performed prior to the execution of the process. The process then proceeds as illustrated in FIGS. 20 to 22 and may comprise a calibration of data from the PIM, the identification of points of interest, a kinematic translation, and an impact analysis. The embodiment described is for illustration purposes only. It may be understood that other embodiments may exist that remain within the scope of the present disclosure. One or more of the system components illustrated in connection with FIGS. 1 to 3 may perform at least a portion of the processes illustrated in FIGS. 20 to 22.

The calibration portion of the analysis, illustrated in FIG. 20, first receives 2002 a periodically sampled 3-axis representation of a time-varying vector quantity. Then the process corrects for sensor offset and gain variations 2004. If it is determined that a new sample rate is needed 2006, the process resamples to a desired sample rate 2010. Then if it is determined whether filtering 2008 is required, the data is filtered according to a desired spectral characteristic using a digital filter 2012. Finally, the vector representation is rotated 2014 so that the Cartesian coordinates are expressed relative to the desired reference frame to produce a calibrated 3-axis sensor waveform 2016. In the embodiment illustrated in FIG. 20, it may be understood that the order of any two consecutively applied linear processes may be reversed without adverse effect and such reversal may be considered as within the scope of the present disclosure.

In an embodiment, the offset and gain correction may be performed on a per-axis basis by linear transformation (subtract offset, multiply by gain), or may be extended to perform non-linear gain correction (e.g., by polynomial or other suitable nonlinear function). As illustrated, the resampling step is optional, but may be employed when, for example, data is collected at different sample rates from an accelerometer (linear acceleration) and gyroscope (rotational velocity) sensors in a PIM. Digital filters may be used to modify the spectral characteristics of the sampled waveform (e.g., for a particular purpose or to a particular standard such as the SAE J211-1 channel frequency class). When the vector components are rotated to the desired reference frame, the desired reference frame may be the HRF as described herein. The processes of calibration may be applied separately for linear acceleration and rotational velocity according to the properties and orientation of the sensors.

FIG. 21 illustrates a second portion 2100 of an example process for kinematically analyzing impact data using components of a personal impact monitoring system as described herein in connection with FIG. 1 and in accordance with an embodiment. In the second part of the process for kinematically analyzing impact data, points of interest within or relative to the head are identified for further analysis. One commonly used point of interest is the center of gravity (CG) of the head. The present disclosure also uses the center of rotation (CR) of the head and the origin of a brain atlas as described herein. Points of interest may also include locations on the interior of the skull that are known to be associated with traumatic brain injury, or that by their geometry may collide with the cerebral cortex under either linear or rotational acceleration. Points of interest may be based at least in part on a grid covering the extent of the inside surface of the skull that encloses the brain, so that all points may be evaluated for their injury potential. Locations on the interior surface of the skull may be located by using a geometrical model of the interior skull surface by using centroids of interpolation patches.

The geometrical model of the skull may be adapted to the unique skull geometry of a particular individual as illustrated in FIG. 21 so as to improve the accuracy of injury criteria associated with linear and rotational skull acceleration. For example, the adaptation may be performed by landmark-based geometric morphometrics using, for example, cephalometric dimensions as landmarks. e.g., Euryon-Euryon, Zygion-Zygion, and Opisthocranion-Glabella. In the example adaptation illustrated in FIG. 21, the process first receives morphological measurements of the skull of a user 2102 and then applies one or more landmark-based transformations from the skull of a user to a reference skull model 2104. The process then performs operations to calculate grid locations based on the reference skull model 2106, calculates a center of gravity and/or a center of rotation 2108, and finally produces one or more position vectors 2110.

FIG. 22 illustrates a third portion 2200 of an example process for kinematically analyzing impact data using components of a personal impact monitoring system as described herein in connection with FIG. 1 and in accordance with an embodiment. The third portion of the example process utilizes a kinematic transform to translate the calibrated waveforms measured by the PIM to the linear acceleration waveform at locations of interest. The method for translation of the measurements to a point of interest accepts one or more position vectors 2202 (from the second portion 2100 of the process), and the calibrated linear acceleration 2210 and rotational velocity waveforms 2204 measured by the PIM. The rotational acceleration 2208 is first calculated 2206 as the numerical derivative (e.g., first difference or first centered difference) of the rotational velocity. A kinematic translation 2212 is then applied to the waveforms to derive the waveform of the linear acceleration vector at the point(s) of interest, the waveform comprised of the calibrated linear acceleration as measured by the PIM, plus tangential and centripetal accelerations due to rotation of the point(s) of interest with respect to the PIM. The calibrated waveforms are then produced 2224.

If the location of interest may be at the interior surface of the skull 2214, the acceleration waveform is further decomposed (using the unit normal 2216 to the skull at the location of interest) into the component of linear acceleration normal

2218 to the interior surface of the skull, and the component tangential 2220 to the interior surface of the skull. In this manner, the analysis provides 2222 the acceleration components that are directly related to the previously described injury mechanisms.

The first step in decomposing the linear acceleration is to find the unit normal 2216 (perpendicular) vector to the inside surface of the skull, which may be calculated using the mathematics of the geometric skull model. For example, if the skull is modeled as the union of planar triangular patches, then the unit normal may be calculated as the normalized cross-product of vectors defining any two sides of the relevant triangular patch.

The component of linear acceleration normal 2218 to the inside surface of the skull may be calculated as the vector dot product of the linear acceleration with the unit normal. Having found the normal component of the linear acceleration, the component tangential 2220 may be calculated as the vector difference of the total linear acceleration and the normal (perpendicular) linear acceleration.

The locations of interest may be determined so as to provide inputs necessary for a finite element analysis of human head motion using, for example, the Strasbourg University Finite Element Head Model ("SUFEHM"). The finite element model may then be used to calculate stresses related to physically distributed injury within the brain.

The third portion of the example process for kinematically analyzing impact data analyzes the waveforms computed by the third portion (kinematic transform) to derive measurements relevant to the assessment of potential injury. These measurements may include maximum magnitude of linear acceleration and maximum magnitude of rotational acceleration. One method of calculation is to use a Head Injury Criterion ("HIC") calculated as:

$$HIC = \max_{t_1, t_2} \left\{ \left[ \frac{1}{t_2 - t_1} \int_{t_1}^{t_2} a(t) \, dt \right]^{2.5} (t_2 - t_1) \right\}$$

In the HIC, a(t) is the linear acceleration waveform measured in g (standard gravity acceleration), and t2-t1 is time (limited to a maximum of 15 milliseconds). An HIC characterizes the area under the curve of the linear acceleration waveform, which, as previously described herein, is largely independent of measurement system bandwidth.

An additional impact measure is the Impact Energy ("IE") defined as:

$$IE = \max_{t_1, t_2} \left\{ \left[ \frac{1}{t_2 - t_1} \int_{t_1}^{t_2} a(t) \circ v(t) \, dt \right]^{\beta} (t_2 - t_1) \right\}$$

In the IE, a(t) is the linear acceleration vector waveform, v(t) is the linear velocity vector waveform derived as the numerical integral of a(t). The parameter β is an exponential weighting factor greater than or equal to 1, determined so as to best correlate IE with an injury tolerance curve (curve of injury threshold on a scatter plot of average impulse power versus impulse duration). The IE calculates the impact energy over the period of peak power. Equivalent calculations of IE may be considered as within the scope of the present disclosure. For example, the velocity vector is identical to the time derivative of the position vector r, therefore the integral portion the IE equation can be calculated as the line integral of $a(r) \circ dr$.

Figure 23:
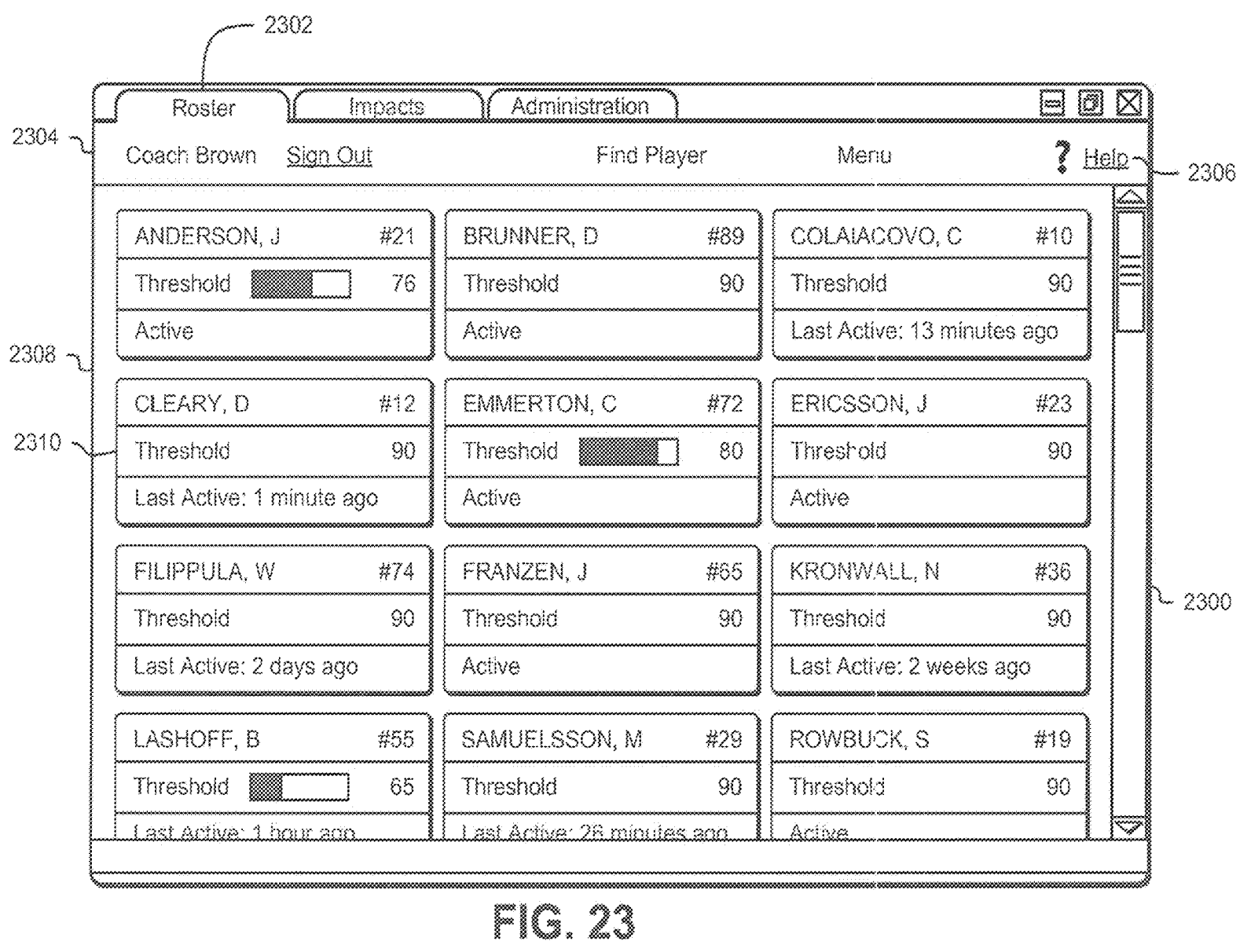

FIG. 23 illustrates an example user interface 2300 for displaying a tiled view of a roster of players associated with a personal impact monitoring system as described herein in connection with FIG. 1 and in accordance with an embodiment. The example user interface 2300 includes a tab area 2302 for displaying different views of the data and an informational area 2304 showing the identity of the current user, and providing one or more areas of interaction with the system such as, for example, a "Help" menu 2306. The user interface may provide a roster-viewing function with one or more views. A tiled-view of the roster 2308 may display a tile 2310 for each participant that may include the name of each participant equipped with a PIM device as well as alert threshold and PIM status (e.g., active, or last time used).

FIG. 24 illustrates an example user interface 2400 for displaying a list view of a roster of users of a personal impact monitoring system as described herein in connection with FIG. 1 and in accordance with an embodiment. In addition to the common elements described in connection with FIG. 23, the example user interface 2400 may display a list view of the roster 2402 with each element in the list view displaying information about the most recent impact of each player.

Figure 25:
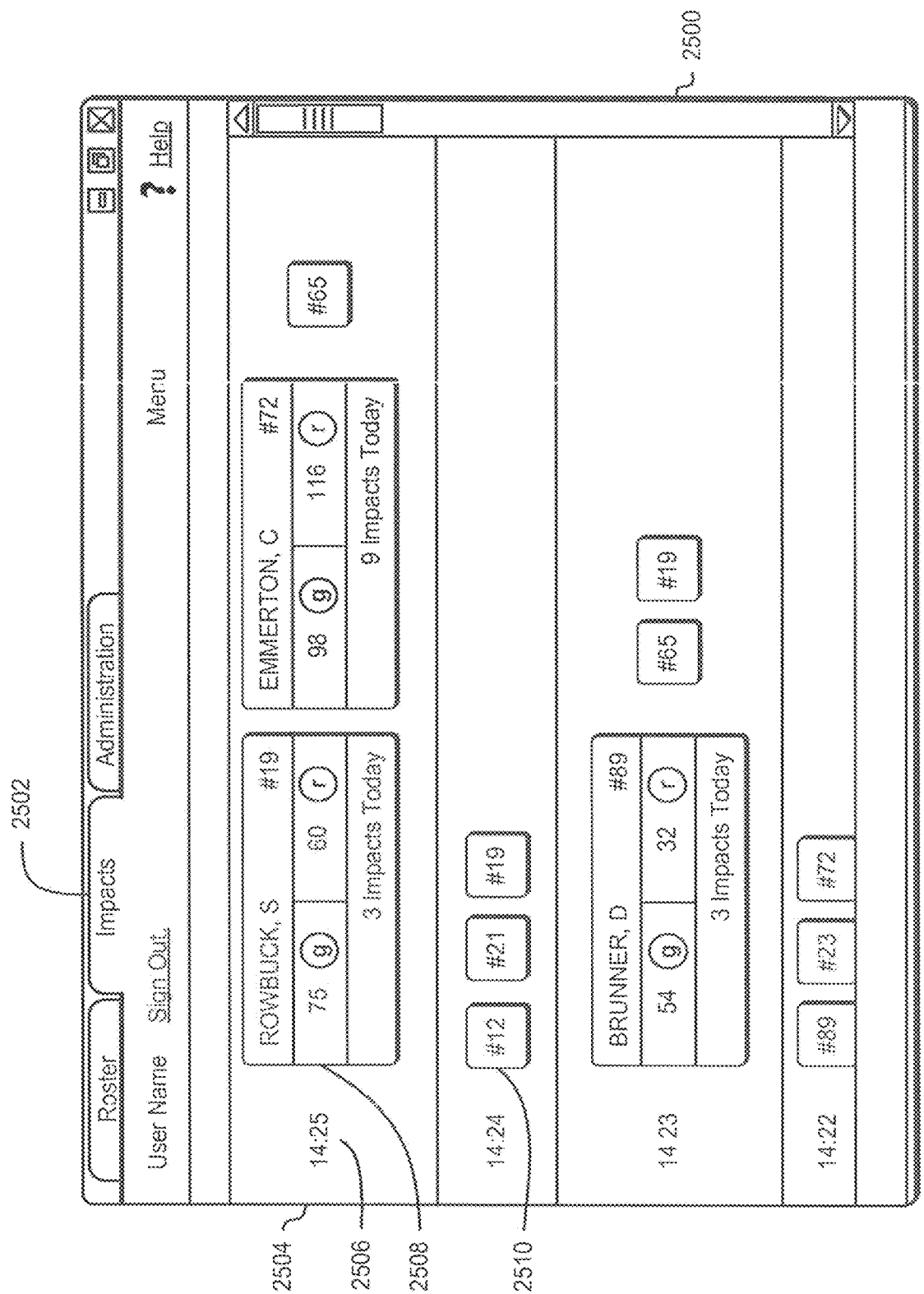

FIG. 25 illustrates an example user interface 2500 for displaying an impact view of a personal impact monitoring system as described herein in connection with FIG. 1 and in accordance with an embodiment. The impact view tab 2502 is selected in FIG. 25 and, in addition to the common elements described in connection with FIG. 23, the example user interface 2500 may display impact information from the impact analysis software as described herein. In the example user interface 2500, the impact information (also referred to herein as impact events) is displayed in a time sorted list 2504. In the time sorted list 2504, if multiple participants receive approximately simultaneous impacts, their names may be displayed together in the time line and may be sorted in order of decreasing hit severity. For example, at a first time 2506, a notable impact 2508 is displayed with basic impact information (i.e., a subset of the impact parameters associated with the impact event). At a second time 2510, no notable impacts may have occurred, but non-notable impacts that may have occurred may be displayed with lesser details.

Figure 26:
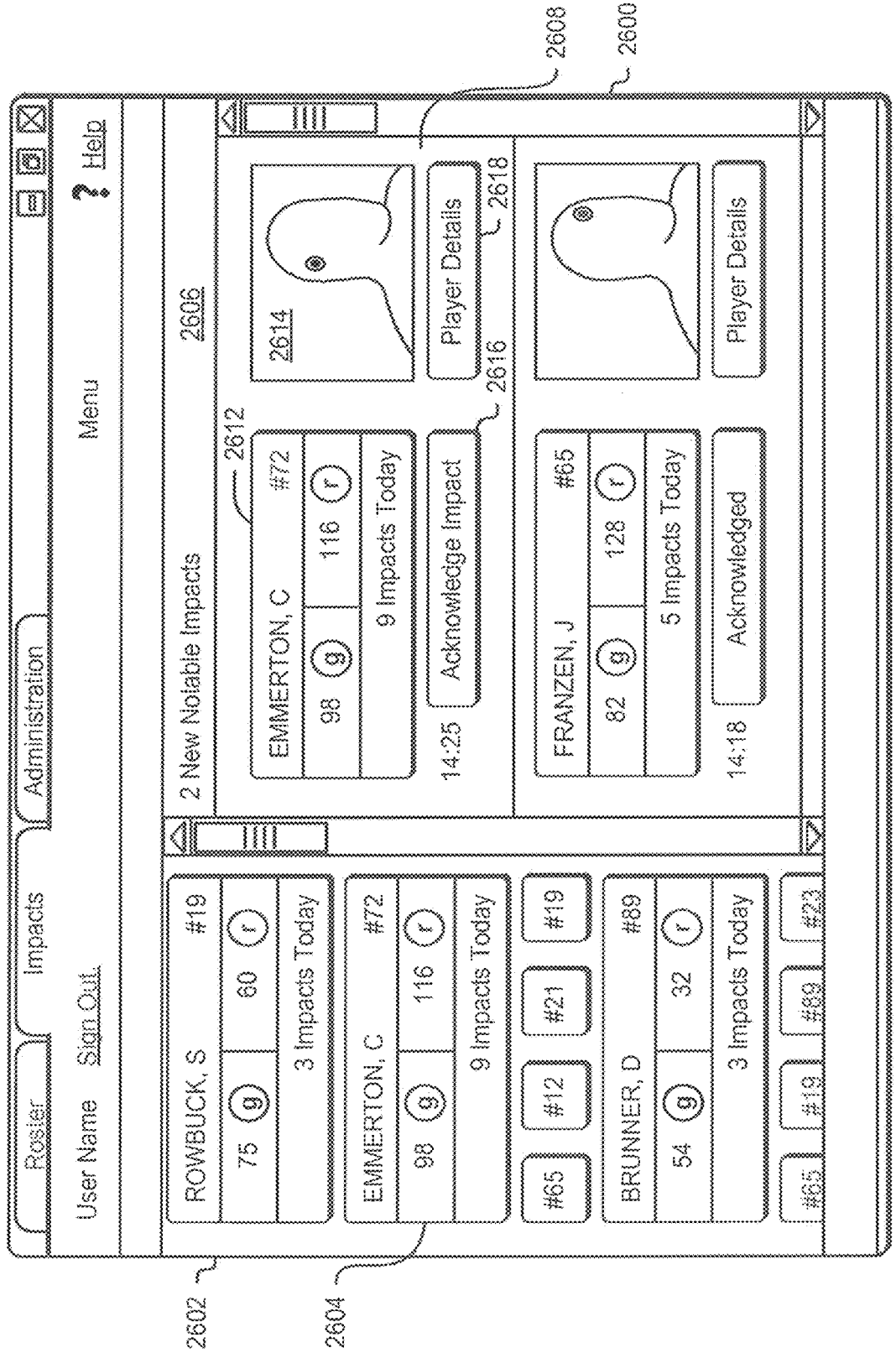

FIG. 26 illustrates an example user interface 2600 for displaying greater impact details for impacts associated with a personal impact monitoring system as described herein in connection with FIG. 1 and in accordance with an embodiment. A time-sorted list 2602 of notable impacts 2604 and/or of other impacts may be displayed. When an impact measure exceeds a threshold, an alert may be issued, the player information may be highlighted, and a large impact information tile 2608 may be displayed. The large impact information tile 2608 may include impact information 2612, impact location information 2614, a button to acknowledge the impact 2616, and/or a button to obtain more player details. If clicked, the impact information tile may expand to display a detailed summary of the impact as described herein in connection with FIG. 27. The button to acknowledge the impact 2616 may be used to, for example, trigger the administration of an injury assessment instrument (e.g., the Sport Concussion Assessment Tool ("SCAT2")).

Figure 27:
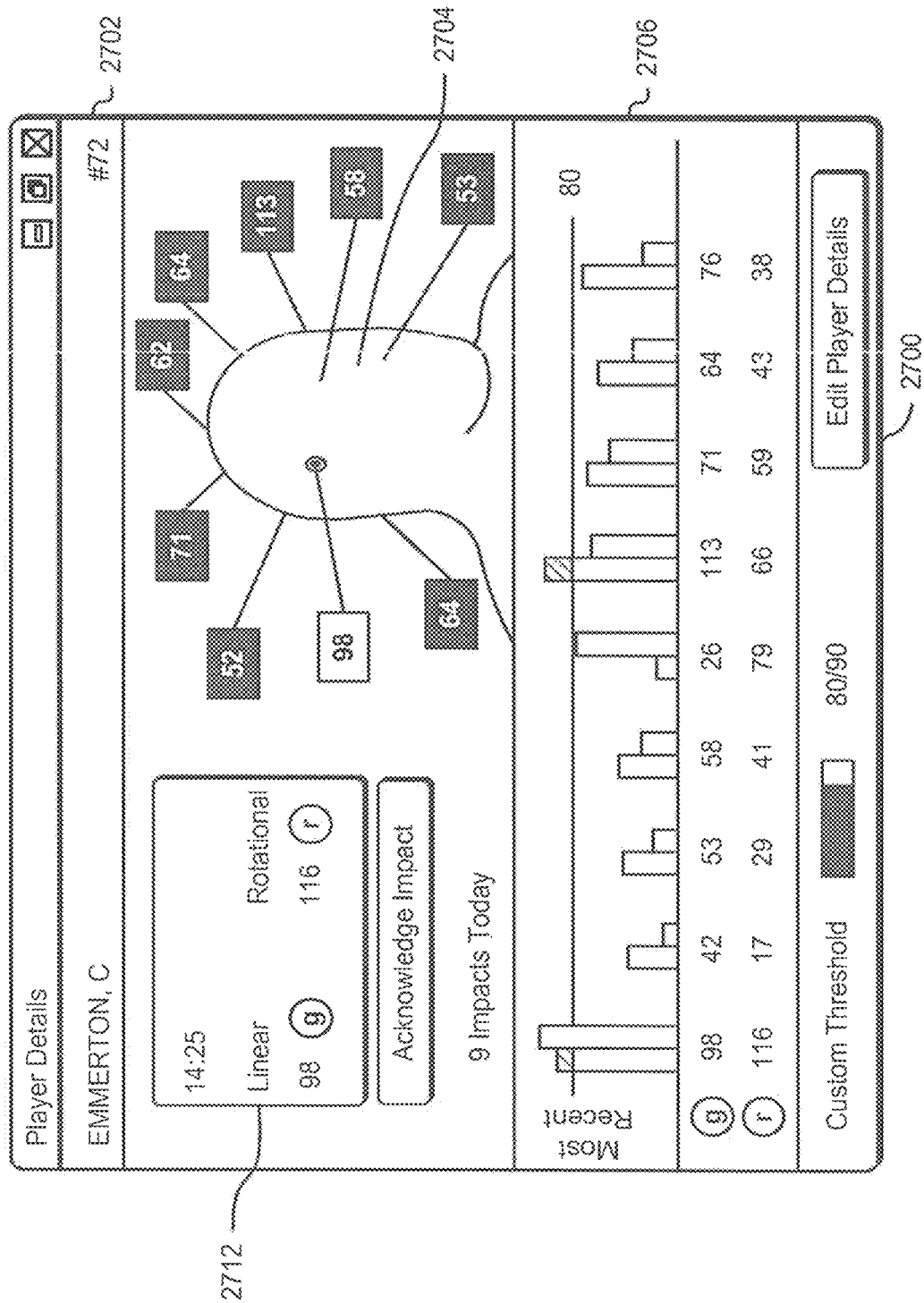

FIG. 27 illustrates an example user interface 2700 for displaying a detailed summary of an impact event associated with a personal impact monitoring system as described herein in connection with FIG. 1 and in accordance with an embodiment. In the example user interface 2700, details about a player 2702 are displayed along with detailed information about the location of all impacts 2704 for that player and/or details about a specific impact 2712. As described herein, a personal impact monitoring system may be configured to set global alarm thresholds that are applied to all participants unless overridden by a personal threshold based on participant history. For each impact measure of interest (e.g., maximum linear acceleration magnitude, or HIC score), one or more thresholds may be defined for each player, either by default or by personalization 2706. A lower threshold may define a level below which impacts are recorded but not considered notable and/or are not displayed in any greater detail. A higher threshold may define a level above which impacts generate an alert for further action, and detailed impact information may be displayed. Impacts that fall between the two thresholds may be displayed as a simple summary of impact information.

Figure 28:
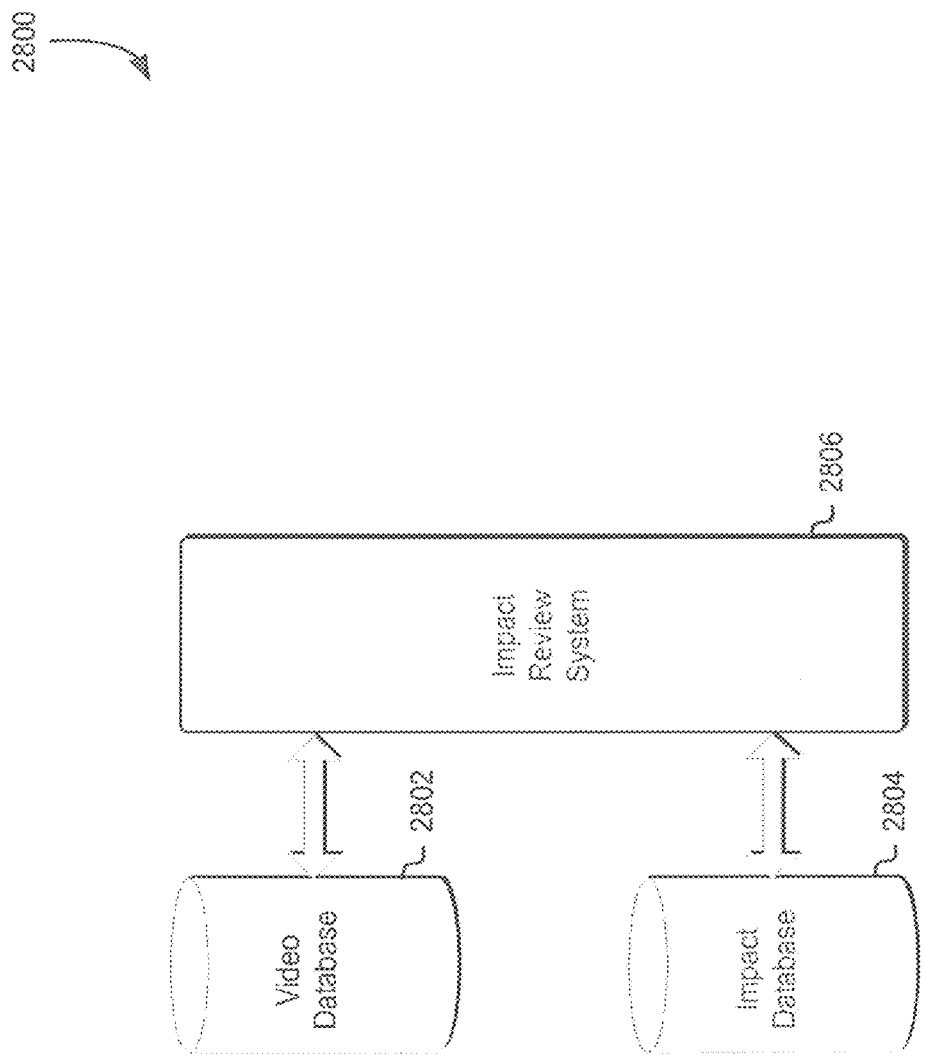
FIG. 28 illustrates an environment where impact data may be reviewed in accordance with an embodiment.

FIG. 28 illustrates an example environment 2800 where impact data may be reviewed from a personal impact monitoring system as described herein in connection with FIG. 1 in accordance with an embodiment. An impact review system 2806 may correlate impact events from an impact database 2804 using, for example, a motion picture representation of impact context (e.g., a video recording of game play or practice) from a video database 2802 and also using impact information generated by an impact monitoring system as described herein. The impact review system 2806 may correlate the display of the motion picture with the display of impact information so as to provide context to the impact information.

The impact review system 2806 may display the impact characteristics prior to the context of the impact, so that the potential for injury may be understood before viewing the actions involved. The impact review system 2806 may allow slow-motion viewing and/or may allow the ability to view the context in both forward and backward directions. To enhance usability of the impact review system 2806, it may include tools for rapid navigation from impact to impact and from player by player.

In an embodiment, the impact review system 2806 is comprised of multiple components: a computing device, display device, data storage, user input device, review software, and means for the components to communicate with each other. The review software may generate displays and provide controls for viewing within the review software application itself, or by creating content that is viewable by and controllable within a general-purpose viewer application such as a web browser. As described in the following paragraphs, the review system receives impact information and context information from external sources, though it is understood that such sources could be combined, or incorporated into the impact review system itself. Furthermore, all of the components except for the review software may be realized as combinations of general-purpose computers and accessory devices.

In an embodiment of the review system, the individual components may be combined into a single physical unit, e.g., a personal computer. In another embodiment of the review system the components may be distributed, with review software and storage hosted on a remote computer (e.g., a network accessible or cloud based system), but the display device and user input device are combined locally (e.g., in a personal computer, tablet computer, or mobile device). It is understood that the various components of the system may be advantageously combined in different configurations for different use environments. Furthermore, certain components may be duplicated or supplemented to improve performance (e.g., both local and remote physical units may include computing devices).

The impact review system 2806 may be configured to display impact information in the context of impact occurrence. To do so, impact review software may have access to both impact and contextual information, the contextual information typically comprising a motion picture of the impact. This may be achieved by accessing data on external systems. Both impact and context information may be accessed either by copying the information from an external system to the review software system's storage device, or by directly accessing the data as stored in the external device (e.g., by accessing its database). Data from external sources, whether impact or context information, may have proprietary data formats. Therefore, the review software system may provide a customized data import/access facility for each unique data source to be supported.

In an embodiment, both impact information and context information may be provided by the same external system. For example, a video camera may be incorporated into an impact-sensing device to capture both impact information and context simultaneously. Alternatively the review system may provide context by displaying an animation of impact motion waveforms provided by an impact monitoring system (e.g., by displaying a visual representation of a head that may be animated to mimic the motions characterized by the waveforms).

In another embodiment, impact information and context information may be provided by different external systems (e.g., a personal impact monitor system and video camera). In this embodiment, the impact information and context information may be time-synchronized in order to provide the correct context for each impact. In such an embodiment, both systems must provide a time reference.

Personal impact monitoring systems may typically capture discrete events. If the impact information is to be displayed in conjunction with context information obtained from a separate source, then each impact record must provide metadata specifying the date and time of the impact. If context information may be provided by a second system configured to capture discrete events then that second system may also be configured to provide metadata that specifies the date and time of each context event.

In an embodiment, the context (e.g., video recordings) may be provided as a continuous recording rather than discrete events. In this case, the time reference may be provided as the start time of the recording. Some systems may encode the start time as part of a data file name, for example "clip-yyyy-mm-dd_hhmmss.ext" where "yyyy" is the year, "mm" is the month, "dd" is the day, "hh" is hours in 24-hour time, and "ext" is the file extension given by the video recorder. More preferably, the start time of the recording may be made available as metadata contained in the recording file.

When impact and context information are provided by separate external sources it is possible that the time references of the systems are not in perfect agreement. Therefore, the impact review software must provide a means to specify and apply a time correction to at least one of the data sources. In an embodiment, the time correction may be entered manually (e.g., by typing a time offset into a data entry box on the display device). In another embodiment, the impact review system may provide assistance by, for example, playing the context motion picture with an overlay or sidebar of the impact information and providing a button that can be clicked at the moment the impact is observed on the motion picture, the time offset being automatically calculated and applied by the review system software.

To understand the context of an impact, it may be necessary to observe not only the impact, but also several seconds of the contextual motion picture prior to and following the impact. Therefore the impact review system may obtain the time of impact from the impact information record, subtract a predetermined preview time (e.g., 5 seconds), and position the motion picture to begin playback at the computed time. Similarly, playback may be terminated after the preview time, impact time, and a predetermined post-view time have elapsed.

To facilitate rapid review, it may be desirable that the impact review system be configured to rapidly navigate from one impact to the next. A navigation control may be provided such that when review of one impact is completed the user may activate the control in order to advance to the next impact. Such navigation may be a natural consequence when both impact and context are provided as discrete events. When the contextual motion picture is provided as a continuous recording, however, it may be necessary to skip intervening portions of the recording that are not associated with impacts. This may be accomplished by obtaining the impact information record for the next impact, subtracting a predetermined preview time from the time of impact, and positioning the motion picture to begin playback at the computed time.

It may also be desirable to review only selected impacts. This may be accomplished by selecting impacts according to information contained in the impact information records. The selectable criteria may depend on the capabilities of the personal impact monitor system, and may include player name or number, impact severity, player position, impact direction, and/or other such criteria. After a selection is made, the impact navigation control may operate on selected impacts, skipping over those that are not selected.

The impact information available for display may depend upon the capabilities of the impact monitoring system. In an embodiment, the impact information is comprised solely of the occurrence of an impact and identification of the player receiving the impact. In another embodiment, the impact information also includes a measure of impact severity and an indication of the direction and location of the impact.

In reviewing impacts, a first step of review may be to preview impact information such as severity and direction of impact so that the potential consequences may be appreciated and discussed prior to observing the context. A second step of review may be to observe the context of the impact by viewing a portion of the motion picture that begins prior to the occurrence of the impact and terminates after, so as to observe the actions that contributed to the impact. Viewing controls to allow slow motion, normal motion, fast motion, reverse play, and forward play may be provided. The impact information may be displayed as an overlay or sidebar to the motion picture. An optional final step of review may be to post-view the impact information for a summary discussion.

In an embodiment, the step of previewing or post-viewing the impact may be accomplished by displaying the impact information as an overlay or sidebar to a portion of the contextual motion picture that precedes or follows (respectively) the portion viewed during the second step. The three steps may be executed successively and without interruption, or the motion picture may be paused at the end of each step. If paused, the transition to the next step may be automatically initiated after a predetermined time and/or a navigation control may be provided to initiate a transition to the next step and optionally to the previous step.

In another embodiment, the step of previewing or post-viewing the impact may be accomplished by displaying the impact information in a primarily static image that may also incorporate visual elements to be manipulated under user control (e.g., a three-dimensional rendering of a human head indicating impact location and direction that may be rotated by moving a computer mouse). The transition to the next step may be automatically initiated after a predetermined time and/or a navigation control may be provided to initiate a transition to the next step and optionally to the previous step.

Because users of the impact review system may be variously informed regarding techniques to prevent head injury, an expert system may be incorporated into the impact review system. For example, an expert system may be created by collecting a large database of impact information and context data, each characterized by the impact information available from the personal impact monitor system. An expert or panel of experts may review each context in order to formulate coaching advice appropriate to the impact and the advice may be stored with the impact information record. As new impacts are received, their impact information may be compared to the database of impacts for similarity, and the advice for the most similar impact may be displayed. As may be contemplated, the use of an expert system is an illustrative example of machine learning techniques that may be applied to provide impact review analysis and other such machine learning techniques may be considered as within the scope of the present disclosure.

In some embodiments, the remote notification device such as the remote notification device 214 described herein in connection with FIG. 2 may be configured (e.g., with a push button) to locally log activations (i.e., activation notifications may be "fire-and-forget" during a game and reconciliation of the notifications that are sent and received may be performed post-game). The post-game review may include identifying the notifications and can act as supplement to the game film used in an impact review system. Such notifications may be used in a "coachable moments" system, where coaches may review activations and assess the film, and may then determine what type of behavior might be avoided. This functionality may provide useful context for assessing where impacts may occur, and the type of hits that may be associated with such impacts.

The following U.S. applications and patents are incorporated by reference herein, and the systems and methods described in these applications may be incorporated into any of the systems, components, or methods herein: U.S. patent application Ser. No. 13/117,223, U.S. Pat. Nos. 8,113,206, 8,113,206, 7,299,804, 6,820,623, 6,691,710, 6,588,430, 6,510,853, 6,508,251, 6,505,628, 6,505,627, 6,505,626, 6,675,806, 6,675,807, 6,491,036, 6,553,996, 6,581,604, 6,626,180, 6,598,605, 6,539,943, 6,415,794, 6,257,239, 6,237,601, 6,200,133, 6,012,919, 5,865,619, 5,879,155, 5,718,575, 6,371,758, 5,836,761, 5,584,687, 5,385,155, 5,365,946, PCT Pub. No. WO 2009/0155223, PCT Pub. No. WO2009/0155224, U.S. Pat. App. Pub. No. 2004/250817, and PCT Pub. No. WO 2009/0012243.

Figure 29:
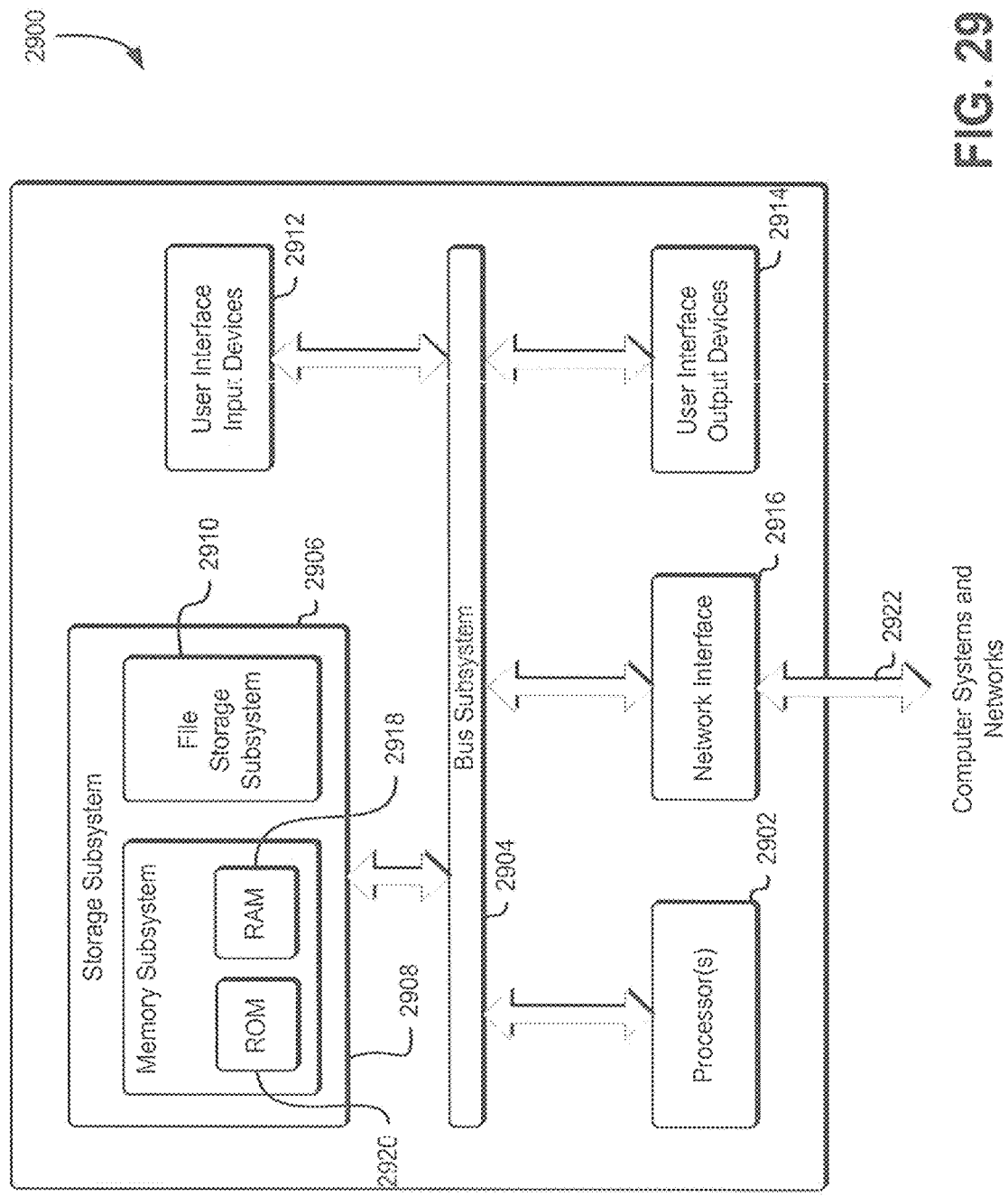
FIG. 29 illustrates a computer system that can be used to implement various aspects of the present disclosure.

FIG. 29 is a simplified block diagram of a computer system 2900 that may be used to practice an embodiment of the present invention. In various embodiments, one or more instances of the computer system 2900 may be used to implement any of the systems illustrated and described above. For example, one or more instances of the computer system 2900 may be used to implement processes for analyzing impact data according to the present disclosure. As shown in FIG. 29, the computer system 2900 may include one or more processors 2902 that may be configured to communicate with and are operatively coupled to a number of peripheral subsystems via a bus subsystem 2904. These peripheral subsystems may include a storage subsystem 2906, comprising a memory subsystem 2908 and a file storage subsystem 2910, one or more user interface input devices 2912, user interface output devices 2914, and a network interface subsystem 2916.

The bus subsystem 2904 may provide a mechanism for enabling the various components and subsystems of computer system 2900 to communicate with each other as intended. Although the bus subsystem 2904 is shown schematically as a single bus, alternative embodiments of the bus subsystem may utilize multiple busses.

The network interface subsystem 2916 may provide an interface 2922 to other computer systems and networks. The network interface subsystem 2916 may serve as an interface for receiving data from and transmitting data to other systems from the computer system 2900. For example, the network interface subsystem 2916 may enable a user computer system device to connect to the computer system 2900 via the Internet and/or other network, such as a mobile network, and facilitate communications using the network(s) and to communicate impact data.

The user interface input devices 2912 may include a keyboard, pointing devices such as a mouse, trackball, touchpad, or graphics tablet, a scanner, a barcode scanner, a touch screen incorporated into the display, audio input devices such as voice recognition systems, microphones, and other types of input devices. Further, in some embodiments, input devices may include devices usable to obtain information from other devices, such as PIMs. Input devices may include, for instance, magnetic or other card readers, one or more USB interfaces, near field communications (NFC) devices/interfaces and other devices/interfaces usable to obtain data (e.g., impact data) from other devices. In general, use of the term "input device" is intended to include all possible types of devices and mechanisms for inputting information to the computer system 2900.

The user interface output devices 2914 may include a display subsystem, a printer, non-visual displays (e.g., audio and/or tactile output devices), or other such display devices. Generally, the user interface output devices 2914 may invoke one or more of any of the five senses of a user. For example, the display subsystem may be a cathode ray tube (CRT), a flat-panel device, such as a liquid crystal display (LCD), light emitting diode (LED) display, or a projection or other display device. In general, use of the term "output device" is intended to include all possible types of devices and mechanisms for outputting information from the computer system 2900. The user interface output devices 2914 may be used, for example, to generate and/or present user interfaces to facilitate user interaction with applications performing processes described herein and variations therein, when such interaction may be appropriate. While a computer system 2900 with user interface output devices is used for the purpose of illustration, it should be noted that the computer system 2900 may operate without an output device, such as when the computer system 2900 is operated in a server rack and, during typical operation, an output device is not needed.

The storage subsystem 2906 may provide a computer-readable storage medium for storing the programming and data constructs that provide the functionality of the present invention. Software (programs, code modules, instructions) that, when executed by one or more processors 2902, may provide the functionality of the present invention, may be stored in storage subsystem 2906. The storage subsystem 2906 may also provide a repository for storing data used in accordance with the present invention. The storage subsystem 2906 may comprise memory subsystem 2908 and disk or file storage subsystem 2910. The storage subsystem may include database storage for impact data or analysis results, file storage for impact data or analysis results and/or other storage functionality.

The memory subsystem 2908 may include a number of memory devices including, for example, random access memory (RAM) 2918 for storage of instructions and data during program execution and read-only memory (ROM) 2920 in which fixed instructions may be stored. The file storage subsystem 2910 may provide a non-transitory persistent (non-volatile) storage for program and data files, and may include a hard disk drive, a floppy disk drive along with associated removable media, a compact disk read-only memory (CD-ROM) drive, a digital versatile disk (DVD), an optical drive, removable media cartridges, and other like storage media.

The computer system 2900 may be of various types including a personal computer, a portable computer, a workstation, a network computer, a mainframe, a kiosk, a server, or any other data processing system. Due to the ever-changing nature of computers and networks, the description of computer system 2900 depicted in FIG. 29 is intended only as a specific example for purposes of illustrating the preferred embodiment of the computer system. Many other configurations having more or fewer components than the system depicted in FIG. 29 are possible.

Embodiments of the disclosure can be described in view of the following clauses:

1. A system for monitoring impacts to one or more participants in a contact sport, comprising:
   one or more personal impact monitors, the one or more personal impact monitors attached to the one or more participants;
   a monitoring station receiver located in a location proximal to the contact sport, the location selected based at least in part on the monitoring station receiver being configured to receive one or more impact events from the one or more personal impact monitors; and
   a monitoring station, the monitoring station configured to implement one or more services to analyze the one or more impact events, wherein the one or more services are configured to:
   receive the one or more impact events from the one or more personal impact monitors using the monitoring station receiver;
   analyze the one or more impact events to select one or more harmful impact events of the one or more impact events, the one or more harmful impact events selected based at least in part on a location of the personal impact monitor;
   add one or more of the one or more harmful impact events to a set of harmful impact events;
   perform one or more statistical analyses of at least a subset of the set of harmful impact events; and
   provide an impact event analysis, the impact event analysis based at least in part on the one or more statistical analyses.

2. The system of clause 1, wherein the one or more services are further configured to perform a kinematic analysis of the one or more impact events, the kinematic analysis comprising:
   modeling a skull as a kinematic rigid body;
   calibrating a set of data from the personal impact monitor based at least in part on the kinematic rigid body;

identifying points of interest on the kinematic rigid body based at least in part on the calibrated set of data;

performing a kinematic translation of the one or more impact events to the kinematic rigid body based at least in part on the points of interest; and performing an analysis of the one or more impact events based at least in part on the kinematic translation.

3. The system of clauses 1 or 2, wherein the kinematic rigid body is based at least in part on one or more morphological measurements of the one or more participants.

4. The system of clauses 1 to 3, wherein the one or more services are further configured to perform an outlier analysis of the one or more impact events, the outlier analysis comprising:

determining one or more statistical measurements of the one or more impact events; and identifying one or more harmful impact events of the set of harmful impact events that differ from the one or more statistical measurements by more than a threshold value.

5. The system of clauses 1 to 4, further comprising one or more near-field data display devices configured to receive impact events from the one or more personal impact monitors when a near-field data display device of the one or more near-field data display devices is placed within a communications range associated with a short-range communication channel associated with one or more of the one or more personal impact monitors.

6. The system of clauses 1 to 5 wherein the one or more personal impact monitors are further configured to measure one or more of: body temperature, heart rate, respiration rate, a location associated with the one or more personal impact monitors, or an altitude associated with the one or more personal impact monitors.

7. A computer-implemented method for monitoring impacts to one or more participants in an activity, comprising:

receiving, using a monitoring station receiver connected to a monitoring station, one or more impact events from one or more personal impact monitors associated with one or more of the one or more participants, each impact event of the one or more impact events specifying a set of impact event parameters;

storing one or more of the one or more impact events in a data storage location connected to the monitoring station;

selecting a set of impact events from the data storage location based in part on at least a subset of the set of impact event parameters; and providing one or more impact analyses based at least in part on the set of impact events.

8. The computer-implemented method of clause 7, wherein the activity is a contact sport.

9. The computer-implemented method of clauses 7 or 8, wherein the personal impact monitor is incorporated into a mouth guard.

10. The computer-implemented method of clauses 7 to 9, wherein the monitoring station is configured to send, to a remote notification device, one or more impact event notifications of the one or more impact events.

11. The computer-implemented method of clauses 7 to 10, wherein the monitoring station includes a personal impact monitor docking station, the personal impact monitor docking station configured to store the one or more personal impact monitors, the personal impact monitor docking station further configured to charge the one or more personal impact monitors.

12. The computer-implemented method of clauses 7 to 11, wherein the personal impact monitor docking station is further configured to sanitize the one or more personal impact monitors by performing one or more of: directing an ultraviolet light onto the one or more personal impact monitors, heating the one or more personal impact monitors, or chemically sanitizing the one or more personal impact monitors.

13. The computer-implemented method of clauses 7 to 12, wherein the personal impact monitor docking station is further configured to:

store one or more of the one or more impact events using a storage device attached to the personal impact monitor docking station; and transfer the one or more of the one or more impact events from the storage device to the data storage location.

14. A tangible non-transitory computer-readable storage medium having stored thereon executable instructions that, when executed by one or more processors of a computer system, cause the computer system to at least:

receive an impact event from a personal impact monitor associated with a participant in an activity;

determine whether the impact event is harmful to the participant based at least in part one or more impact event parameters associated with the impact event;

add the impact event to one or more sets of impact events based at least in part on whether the impact event is harmful;

perform one or more statistical analyses on the one or more sets of impact events; and provide an impact event analysis, the impact event analysis based at least in part on the one or more statistical analyses.

15. The tangible non-transitory computer-readable storage medium of clause 14, wherein the activity is a contact sport.

16. The tangible non-transitory computer-readable storage medium of clauses 14 or 15, wherein the impact event is received from a personal impact monitor.

17. The tangible non-transitory computer-readable storage medium of clauses 14 to 16, wherein the impact event by a monitoring station receiver.

18. The tangible non-transitory computer-readable storage medium of clauses 14 to 17, wherein the monitoring station receiver is located in a location proximal to the activity, the location selected based at least in part on the monitoring station receiver being configured to receive one or more impact events.

19. The tangible non-transitory computer-readable storage medium of clauses 14 to 18, wherein the executable instructions that cause the computer to provide the impact event analysis further include instructions that cause the computer to display the impact event using a display connected to the computer.

20. The tangible non-transitory computer-readable storage medium of clauses 14 to 19, wherein the executable instructions that cause the computer to provide the impact event analysis further include instructions that cause the computer to correlate one or more impact events of the one or more sets of impact events with a visual recording of the activity based at least in part on the impact event parameters.

The specification and drawings are, accordingly, to be regarded in an illustrative rather than a restrictive sense. It will, however, be evident that various modifications and changes may be made thereunto without departing from the broader spirit and scope of the invention as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including" and "containing" are to be construed as open-ended terms (i.e., meaning "including, but not limited to,") unless otherwise noted. The term "connected," when unmodified and referring to physical connections, is to be construed as partly or wholly contained within, attached to or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. The use of the term "set" (e.g., "a set of items") or "subset," unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

Conjunctive language, such as phrases of the form "at least one of A, B, and C," or "at least one of A, B and C," unless specifically stated otherwise or otherwise clearly contradicted by context, is otherwise understood with the context as used in general to present that an item, term, etc., may be either A or B or C, or any nonempty subset of the set of A and B and C. For instance, in the illustrative example of a set having three members, the conjunctive phrases "at least one of A, B, and C" and "at least one of A, B and C" refer to any of the following sets: {A}, {B}, {C}, {A, B}, {A, C}, {B, C}, {A, B, C}. Thus, such conjunctive language is not generally intended to imply that certain embodiments require at least one of A, at least one of B and at least one of C each to be present.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory (referred to herein as a "non-transitory computer-readable storage medium"), may be tangible (referred to herein as a "tangible computer-readable storage medium"), or may be both tangible and non-transitory (referred to herein as a "tangible non-transitory computer-readable storage medium").

The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Embodiments of this disclosure are described herein, including the best mode known to the inventors for carrying out the invention. Variations of those embodiments may become apparent to those of ordinary skill in the art upon reading the foregoing description. The inventors expect skilled artisans to employ such variations as appropriate and the inventors intend for embodiments of the present disclosure to be practiced otherwise than as specifically described herein. Accordingly, the scope of the present disclosure includes all modifications and equivalents of the subject matter recited in the claims appended hereto as permitted by applicable law. Moreover, any combination of the above-described elements in all possible variations thereof is encompassed by the scope of the present disclosure unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A system for monitoring impacts to one or more participants in a contact sport, comprising:
    a mouth guard embedded with one or more impact sensors comprising accelerometers, wherein the mouth guard is wearable by the one or more participants;
    a processor configured to:
        aggregate impact data received from the one or more impact sensors to determine a total amount of impacts for the one or more participants;
        use a web application to display the aggregated impact data for the one or more participants, wherein the web application is customizable, by a user, to display the amount of impacts, linear accelerations, angular accelerations, and location of impacts on a rendering of a human head illustrated as a heat map for each of the one or more participants; and
        generate an impact measurement for each of the one or more participants using data from the one or more impact sensors and provide an alert to the user on the web application when the impact measurement exceeds a threshold;
    a charging case configured to recharge batteries associated with the mouth guard and to sanitize the mouth guard with ultraviolet (UV) light; and
    a portable case configured with wheels to store the mouth guard and a plurality of additional mouth guards.

2. The system of claim 1, wherein the one or more impact sensors further comprises one or more:
    magnetic compasses;
    gyroscopes; and
    piezo tubes.

3. The system of claim 1, wherein the aggregated impact data includes a magnitude of the impacts, over time, for the one or more participants.

4. The system of claim 1, wherein the aggregated impact data received from one or more impact sensors comprises impact data with respect to the head of the one or more participants.

5. The system of claim 4, wherein the aggregated impact data includes:
- a location of impact;
- severity of impact; and
- a quantity of impacts with respect to the head of the one or more participants.

6. The system of claim 1, wherein the processor is further configured to:
- receive video data obtained during the contact sport; and
- use the web application to display the video data for the user to review impacts for each of the one or more participants.

\* \* \* \* \*